US011241167B2

(12) United States Patent
Vu et al.

(10) Patent No.: US 11,241,167 B2
(45) Date of Patent: Feb. 8, 2022

(54) APPARATUS AND METHODS FOR CONTINUOUS AND FINE-GRAINED BREATHING VOLUME MONITORING

(71) Applicant: THE REGENTS OF THE UNIVERSITY OF COLORADO, A BODY CORPORATE, Denver, CO (US)

(72) Inventors: Tam Vu, Denver, CO (US); Phuc V. Nguyen, Denver, CO (US); Ann C. Halbower, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 501 days.

(21) Appl. No.: 15/679,282

(22) Filed: Aug. 17, 2017

(65) Prior Publication Data
US 2018/0049669 A1  Feb. 22, 2018

Related U.S. Application Data

(60) Provisional application No. 62/376,190, filed on Aug. 17, 2016.

(51) Int. Cl.
| | |
|---|---|
| *A61B 5/091* | (2006.01) |
| *A61B 5/05* | (2021.01) |
| *A61B 5/08* | (2006.01) |
| *A61B 5/113* | (2006.01) |
| *A61B 5/0507* | (2021.01) |
| *A61B 5/00* | (2006.01) |
| *A61B 5/11* | (2006.01) |

(52) U.S. Cl.
CPC .......... *A61B 5/0816* (2013.01); *A61B 5/0507* (2013.01); *A61B 5/091* (2013.01); *A61B 5/113* (2013.01); *A61B 5/4818* (2013.01); *A61B 5/05* (2013.01); *A61B 5/1127* (2013.01); *A61B 5/1128* (2013.01)

(58) Field of Classification Search
CPC ......... A61B 5/113–1135; A61B 5/7285–7292; A61B 5/05–0538
See application file for complete search history.

(56) References Cited

U.S. PATENT DOCUMENTS 4,503,552 A * 3/1985 Miyahara ............. A61B 6/4429
378/196
10,426,399 B1 * 10/2019 Kayyali ............... A61B 5/0077
(Continued)

OTHER PUBLICATIONS

Harte et al. "Chest wall motion analysis in healthy volunteers and adults with cystic fibrosis using a novel Kinect-based motion tracking system." Med Biol Eng Comput. Nov. 2016;54(11):1631-1640. (Year: 2016).*

*Primary Examiner* — Meredith Weare

(57) ABSTRACT

The present invention provides an apparatus for the measurement and monitoring of the breathing volume of a subject. In certain embodiments, the invention further provides a method of using the apparatus to diagnose a subject as suffering from a respiratory disorder. In other embodiments, the apparatus and method can be used to monitor the breathing volume of a subject, while compensating for random body movement of the subject during the monitoring period.

30 Claims, 35 Drawing Sheets
(34 of 35 Drawing Sheet(s) Filed in Color)

(56) References Cited

U.S. PATENT DOCUMENTS

| | | | | |
|---|---|---|---|---|
| 2010/0292568 | A1* | 11/2010 | Droitcour | A61B 5/05 600/425 |
| 2012/0022348 | A1* | 1/2012 | Droitcour | A61B 5/0816 600/323 |
| 2012/0179005 | A1* | 7/2012 | McCool | A61B 5/1116 600/301 |
| 2013/0135137 | A1* | 5/2013 | Mulder | A61B 5/0507 342/28 |
| 2013/0324876 | A1* | 12/2013 | Bernal | A61B 5/091 600/538 |
| 2013/0338525 | A1* | 12/2013 | Allen | A61B 5/1135 600/534 |
| 2014/0163343 | A1* | 6/2014 | Heneghan | A61B 5/0507 600/324 |
| 2015/0141858 | A1* | 5/2015 | Razavi | A61B 5/1107 600/513 |
| 2016/0338599 | A1* | 11/2016 | DeBusschere | A61B 5/0261 |
| 2017/0336018 | A1* | 11/2017 | Xie | F16M 11/18 |
| 2018/0081030 | A1* | 3/2018 | McMahon | A61B 5/0507 |
| 2019/0021607 | A9* | 1/2019 | Heneghan | A61B 5/0507 |

* cited by examiner

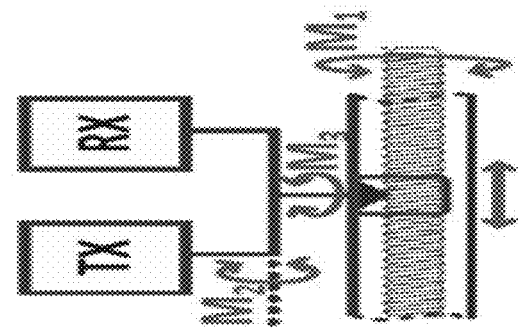
FIG. 1D
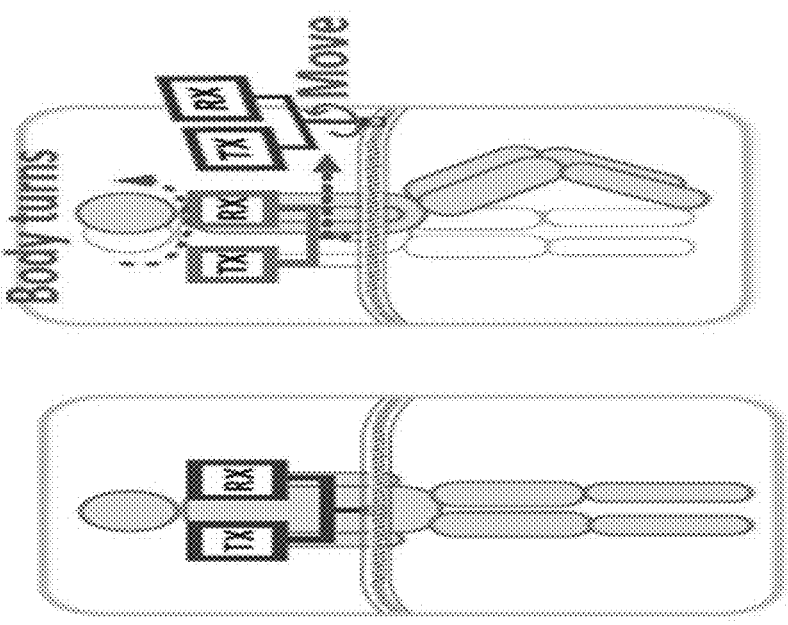
FIG. 1C
FIG. 1B
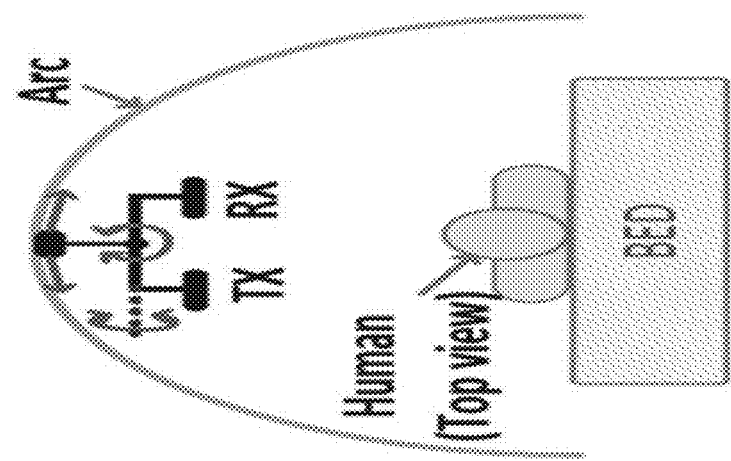
FIG. 1A

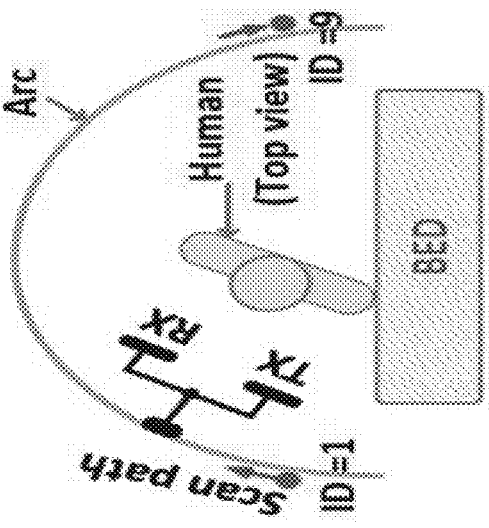
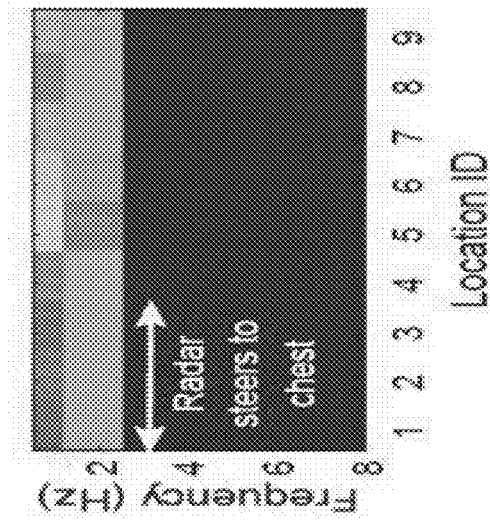
FIG. 7A
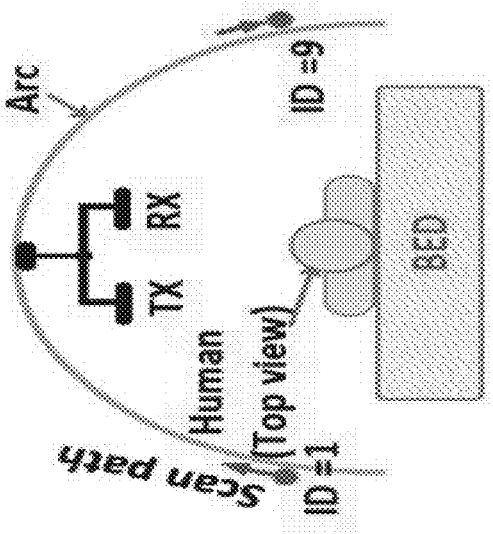
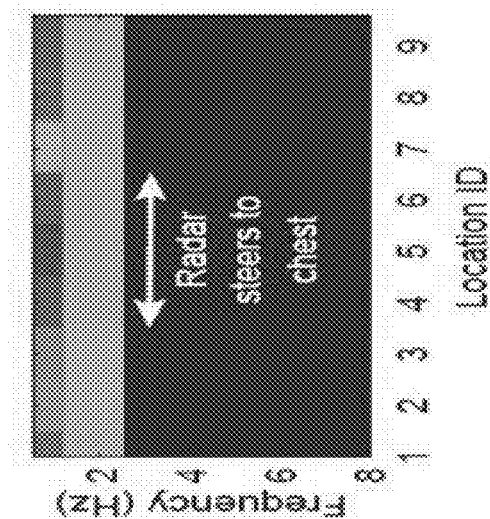
FIG. 7B
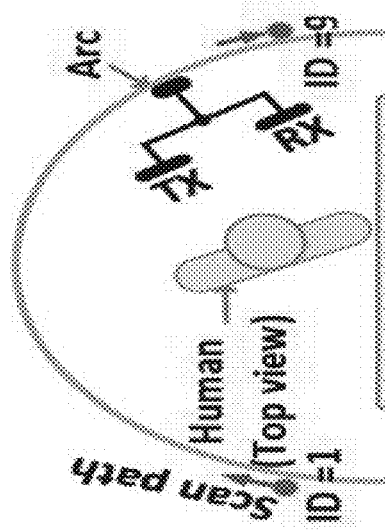
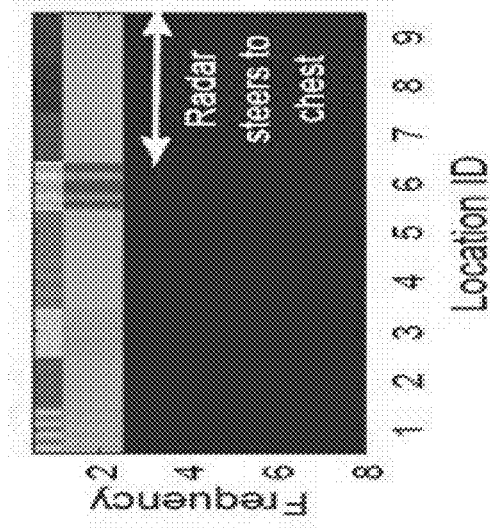
FIG. 7C

FIG. 16A
Volumetric Displacement Models
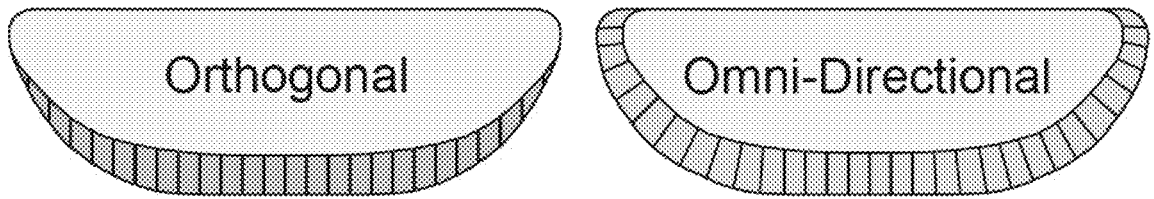
FIG. 16B
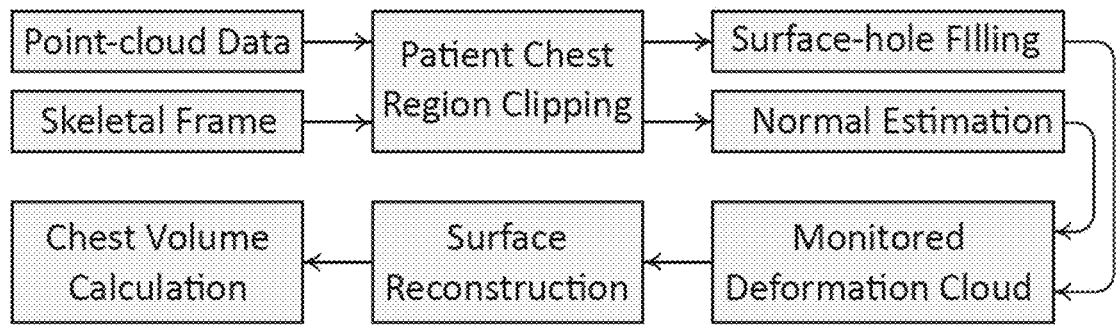
FIG. 17A
FIG. 17B
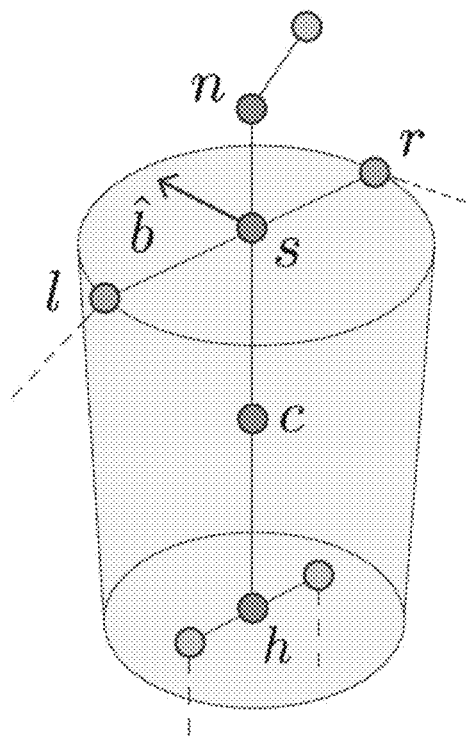
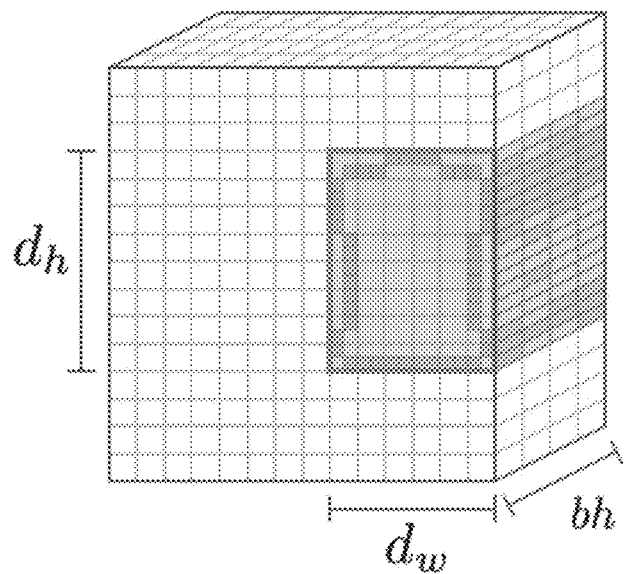

FIG. 19A FIG. 19B
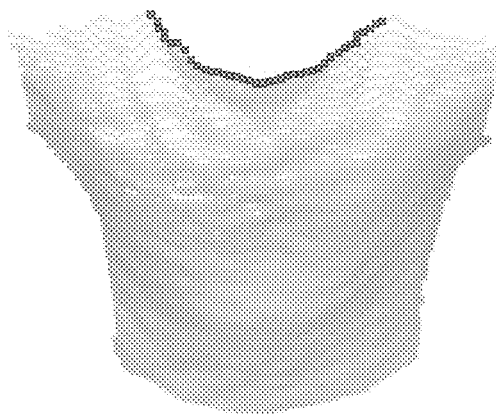 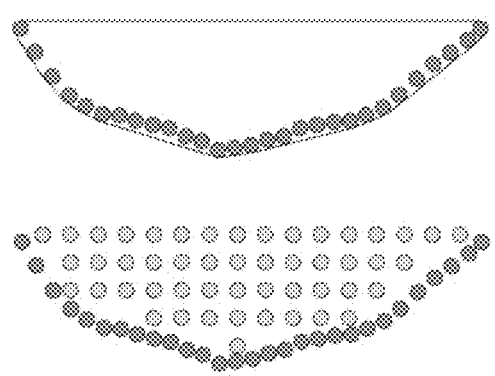
FIG. 19C FIG. 19D FIG. 19E
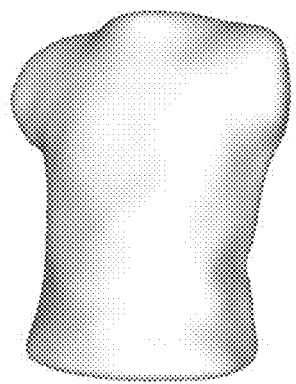 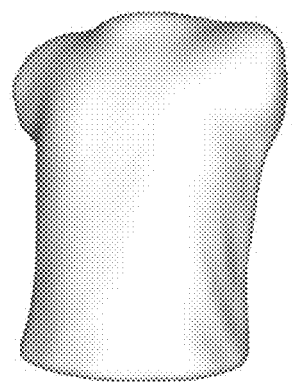 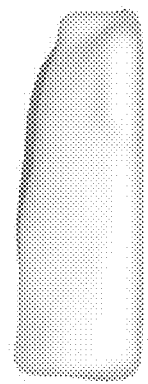
FIG. 20
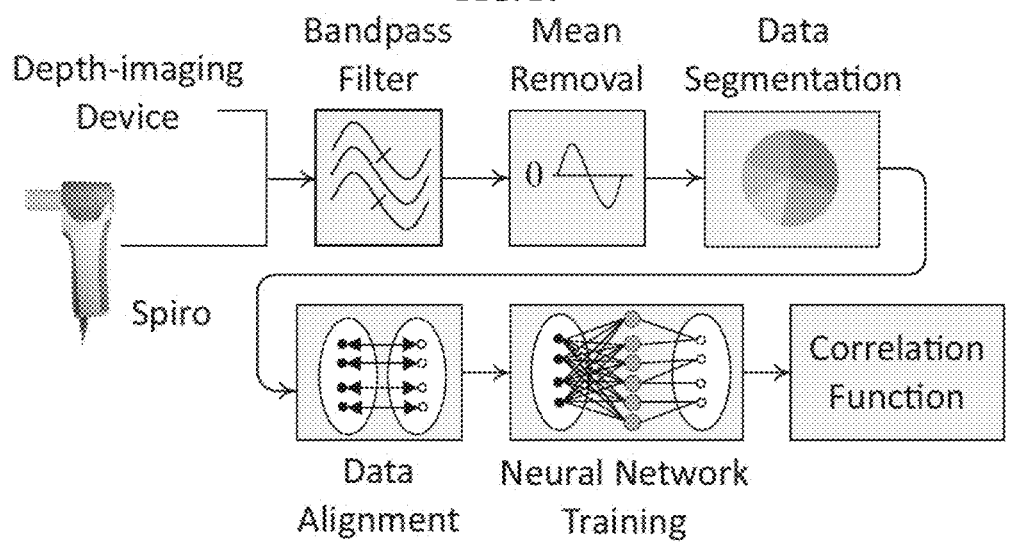

FIG. 25
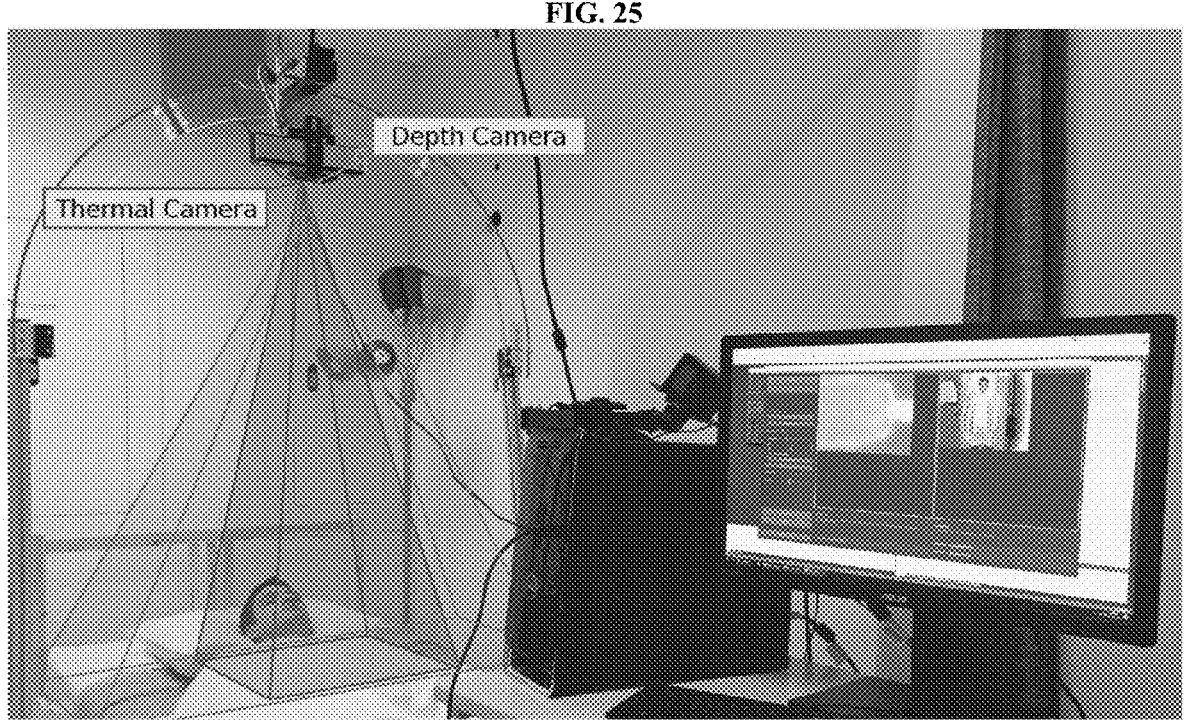
FIG. 26A  FIG. 26B  FIG. 26C  FIG. 26D
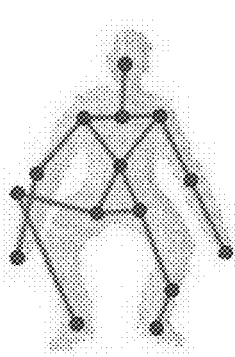 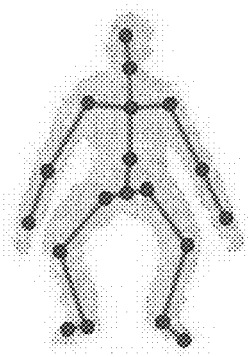 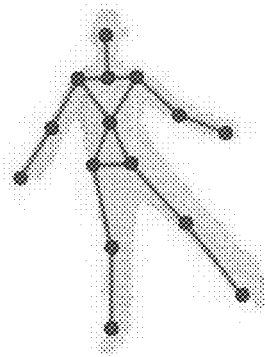 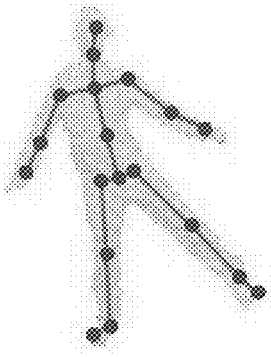

(a)

(b)

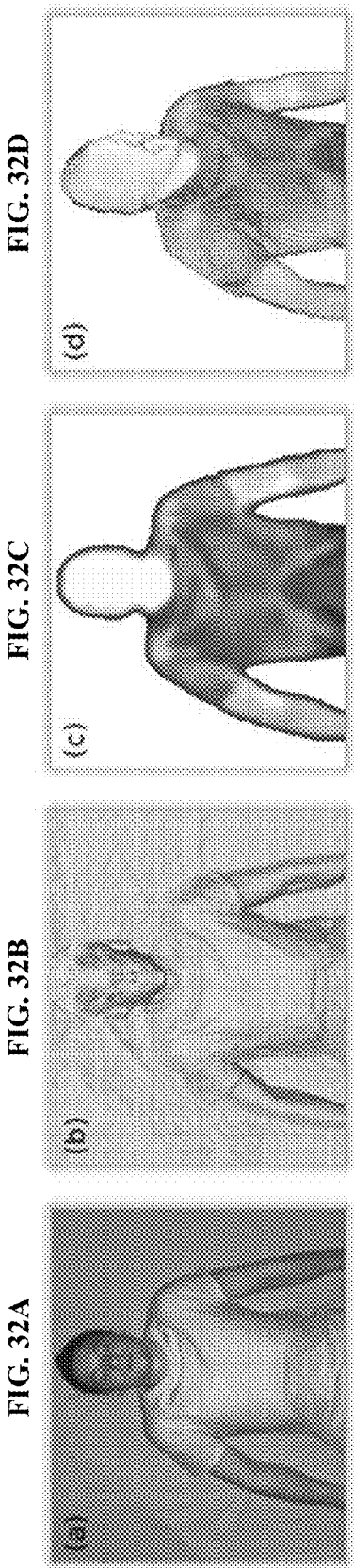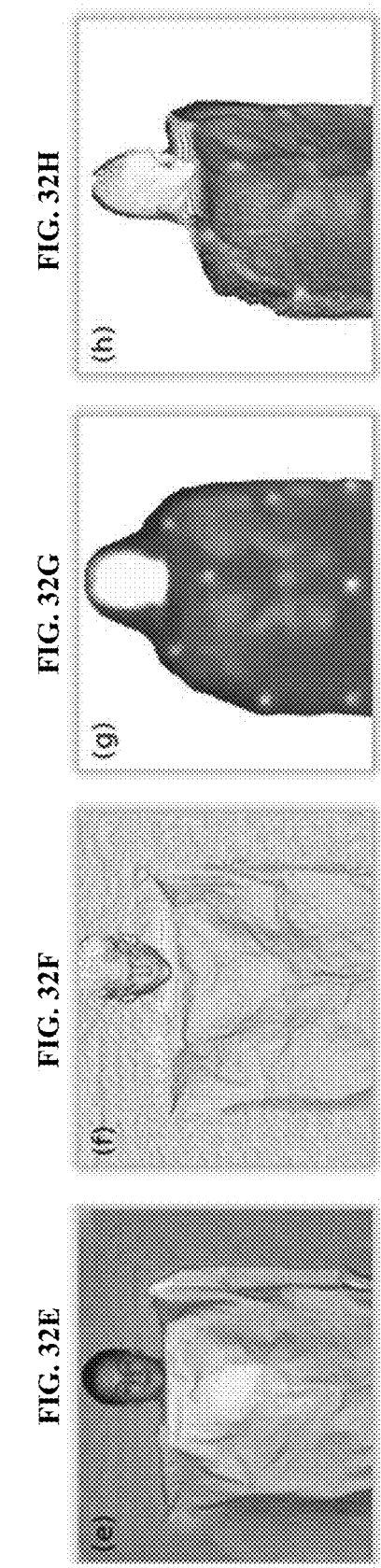
FIG. 32A  FIG. 32B  FIG. 32C  FIG. 32D
FIG. 32E  FIG. 32F  FIG. 32G  FIG. 32H FIG. 36A
FIG. 36B
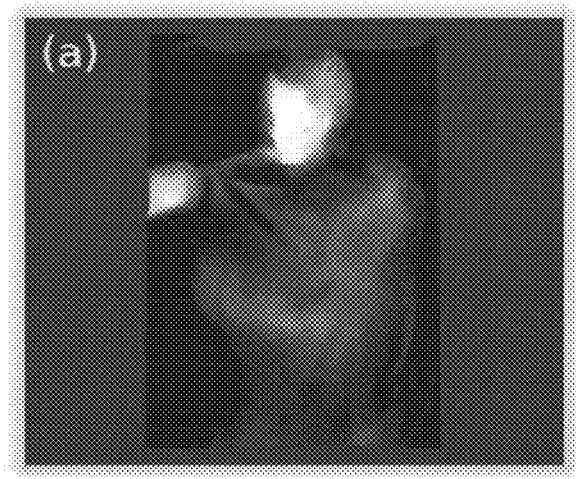
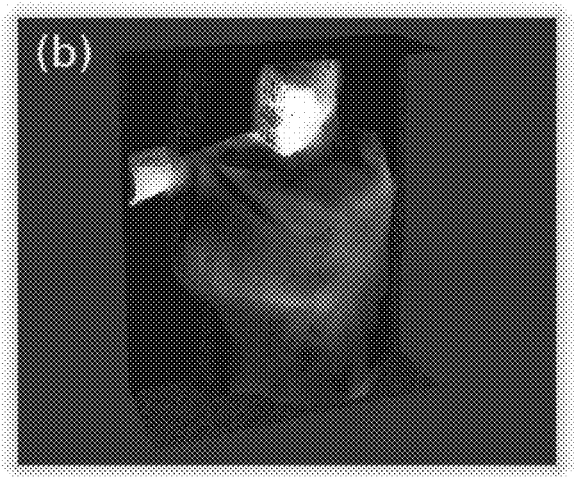
FIG. 36C
FIG. 36D
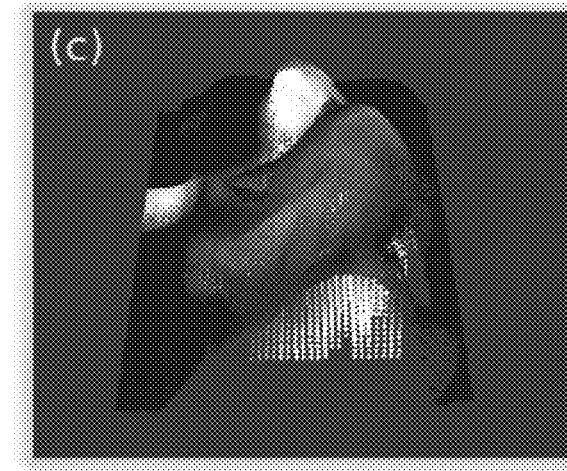
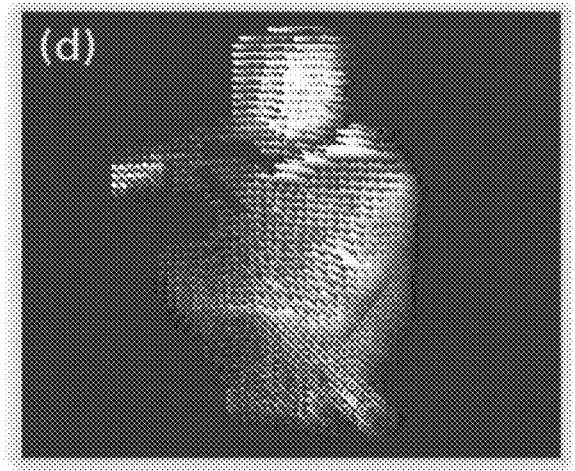

APPARATUS AND METHODS FOR CONTINUOUS AND FINE-GRAINED BREATHING VOLUME MONITORING

CROSS-REFERENCE TO RELATED APPLICATIONS

This application claims priority under 35 U.S.C. § 119(e) to U.S. Provisional Patent Application No. 62/376,190, filed Aug. 17, 2016, the entire disclosure of which is incorporated herein by reference.

BACKGROUND OF THE INVENTION

Continuous respiratory rate and volume monitoring play an important role in health care. While an abnormality in breathing rate is a good indication of respiratory diseases such as interstitial lung disease (faster than average) or drug overdose (slower than average), fine-grained breathing volume information adds valuable information about the physiology of disease. Common obstructive airway diseases such as asthma and chronic obstructive pulmonary disease (COPD), for example, are characterized by the decreased flow rate measure at different breathing volumes. A constant loss of lung volume in these diseases indicates not only acute changes in the disease stability, but also lung remodeling and other irreversible states of diseases. Further, patients with lower airway diseases such as cystic fibrosis or tuberculosis can be diagnosed as frequent sudden drops in breathing volume are detected. Therefore, accurate and fine-grained breathing volume measurements could offer rapid and effective diagnostic clues to the development of disease progression.

Often, measuring and monitoring lung volume is obtrusive and difficult, especially while a patient is sleeping. Many patients with respiratory diseases show their symptoms only for a short period and at random times. In addition, standard available methods of measuring breathing volume are not amenable to more special needs patients such as newborn infants or pregnant women. In fact, breathing volume of prematurely-born, or preterm, babies needs to be closely and continuously monitored. A decrease of the babies' breathing flow and volume must be promptly detected well before it causes oxygen desaturation, so that doctors can provide an effective neonatal ventilation intervention.

Further, sleep-disordered breathing is observed in pregnant women who did not have sleep apnea prior to pregnancy, and apnea leads to abnormal pregnancy outcomes. In these cases, many develop apnea only for a short period of time. Hence, monitoring them non-invasively over a longer term to detect lung volume changes is critical.

Further, long-term monitoring of breathing volume during sleep detects sleep-related breathing disorders common in 5% of children and 10-40% of the adult population. Fine-grained and continuous breathing volume information helps classifying different types of hypopnea (partial airflow obstruction common in children) during sleep to better define the abnormality and direct proper treatment strategies where obstructive hypopnea is treated differently than central apnea. For such health care practices, the detection of disease and the observation of disease progression or remission is viable only with an accurate and fine-grained breathing volume monitoring technique over an extended period of time.

Current practice for long-term breathing volume monitoring is obtrusive: airflow are measured from the nose and mouth qualitatively or at best semi-quantitatively with pressure manometers or impedance chest belt. Certain methods that rely on radio wave signal reflection measurement methods are available but work only if the patient remains static and unobstructed. Thus, they are not applicable for long-term monitoring where subject movement is unavoidable. Moreover, it can estimate breathing volume only once in every breathing cycle.

There is a need in the art for unobtrusive and accurate methods and devices for measuring and monitoring breathing volume in patients, especially while they are sleeping. There is also a need in the art for measuring and monitoring breathing volume in patients that do not remain still during the measurement period. The present invention satisfies these unmet needs.

BRIEF SUMMARY OF THE INVENTION

In one aspect, the invention provides an apparatus for measuring and monitoring breathing volume of a subject. In certain embodiments, the device comprises a volume estimator comprising a directional radio wave emitter and a directional radio wave receiver, wherein the emitter and the receiver are capable of being positioned such that the emitter emits a continuous radio wave to at least one position of the subject's chest and the receiver monitors the radio wave that is reflected by the at least one position of the subject's chest. In other embodiments, the device comprises a navigator device, which is capable of repositioning the emitter and/or receiver of the volume estimator upon detecting body movement from the subject.

In certain embodiments, the radio wave emitter emits a single tone continuous radio wave. In other embodiments, the radio wave emitter emits a single tone continuous radio wave at about 2.4 GHz. In yet other embodiments, the radio wave receiver collects and outputs data at a sampling rate of about 1 kHz to about 100 kHz.

In certain embodiments, the apparatus detects large- and small-scale body movement and radar occlusion in the subject.

In certain embodiments, the volume estimator is mounted on a mechanical motion control system. In other embodiments, the navigator device controls the mechanical motion control system in real-time. In yet other embodiments, the mechanical motion control system is capable of rotating the radio wave emitter and radio wave detector with 360° of freedom on three axes. In yet other embodiments, the mechanical motion control system is mounted on a track. In yet other embodiments, the mechanical motion control system is capable of motion across the chest of the subject. In yet other embodiments, the mechanical motion control system is capable of motion along the length of the subject. In yet other embodiments, the mechanical motion control system is mounted on a bed or another horizontal platform on which a subject lies.

In certain embodiments, the apparatus further comprises a spirometer, which is capable of measuring the subject's breathing volume.

The invention further provides a method of measuring and monitoring the breathing volume of a subject. In certain embodiments, the method comprises (a) directing a continuous radio wave from a radio wave emitter at least one position on the subject's chest. In other embodiments, the method comprises (b) monitoring radio waves reflected by the at least one position of the subject's chest using a radio wave receiver. In yet other embodiments, the method comprises (c) using any monitored phase and/or signal strength changes in the reflected radio waves to measure changes in volume of the subject's chest.

In certain embodiments, the method comprises repeating steps (a)-(c) at least once for one or more positions on the subject's chest while the subject is connected to a spirometer, and correlating any monitored phase and/or signal strength changes in the reflected radio waves with the subject's breathing volume. In other embodiments, the method further comprises monitoring any changes in the subject's posture or position and relocating the radio wave emitter and radio wave receiver so that the continuous radio wave from a radio wave emitter is directed at at least one position on the subject's chest. In yet other embodiments a change in the subject's posture or position is detected when the radio wave receiver no longer receives interfering signals from the subject's heartbeat or respiration. In yet other embodiments, the radio wave emitter and radio wave receiver move to positions such that the radio wave receiver once again monitors radio waves reflected by the at least one position of the subject's chest.

In certain embodiments, the reflected radio wave measurements are collected for at least one position of the subject's chest. In other embodiments, any interfering signals from the subject are suppressed from the measuring of changes in volume of the subject's chest. In yet other embodiments, the interfering signals are caused by at least one selected from the group consisting of body movement, vibration due to the respiration of the subject and vibration due to the heartbeat of the subject.

In certain embodiments, the subject is sleeping. In certain embodiments the subject is a mammal. In other embodiments, the subject is a human.

In certain embodiments, a medical professional uses the measuring of the breathing volume of the subject to diagnose the subject as having or not a respiratory disease or disorder. In other embodiments, the respiratory disease or disorder is one or more selected from the group consisting of hypopnea, apnea, sleep apnea, snoring, insomnia, obstructive sleep apnea, central sleep apnea, child sleep apnea, infant sleep apnea, pregnancy induced sleep apnea, and sleep related groaning.

The invention further provides a kit comprising the apparatus of the invention and instructions for the operation of the apparatus. In certain embodiments, the kit comprises a computer for processing the data collected by the apparatus.

The invention further provides a computer implemented method of demodulating fine-grained breathing volume from received signals. In certain embodiments, the method comprises gathering a radio signal input from radio waves deflected off of the chest of a breathing subject. In other embodiments, the method comprises filtering out environmental noise in the radio signal input using a bandpass filter. In yet other embodiments, the method comprises defining a zero crossing point from the filtered data, corresponding to the subject's chest position halfway between inhalation and exhalation. In yet other embodiments, the method comprises applying a non-linear correlation function to the zero crossing point measurements. In yet other embodiments, the method comprises inferring breathing volume based on the non-linear correlation function.

The invention further provides a computer implemented method of training the neural network for movement-to-volume mapping. In certain embodiments, the method comprises having a subject breath into a spirometer. In other embodiments, the method comprises collecting breathing volume data from the spirometer over a period of time while simultaneously gathering radio signal data from radio waves deflected off of the chest of the breathing subject. In yet other embodiments, the method comprises defining a zero crossing point in the breathing volume data and the radio signal data and aligning the breathing volume data and the radio signal data using the zero crossing points. In yet other embodiments, the method comprises segmenting the aligned data. In yet other embodiments, the method comprises applying the segments to a Bayesian back-propagation neural network training to obtain a non-linear correlation function representing the relationship between the two data sets.

The invention further provides a computer implemented method of estimating posture of a subject lying on a surface. In certain embodiments, the method comprises gathering a radio signal input from radio waves deflected off of the chest of a breathing subject by scanning at a number of points across the surface on which the subject is lying. In other embodiments, the method comprises filtering out excess signal noise while keeping the signal at a frequency sufficient to pick up the subject's vital signs. In yet other embodiments, the method comprises determining the power distribution of the reflected signal during the scan. In yet other embodiments, the method comprises determining the location of the maximum power of the reflected signal which indicates the posture of the subject.

The invention further provides a computer implemented method of estimating chest position of a subject in real-time. In certain embodiments, the method comprises mapping the subject's chest while the subject is still by gathering a radio signal input from radio waves deflected off of the chest of the breathing subject by scanning at a number of different areas across the chest of the subject and then extracting the radio signal data into 16 features per area. In other embodiments, the method comprises collecting real-time radio signal reflection data at different areas across the chest of the subject and then extracting the real-time signal data into 16 features per area as the subject moves. In yet other embodiments, the method comprises correlating the real-time data with the mapping data to estimate the subject's chest position.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description of specific embodiments of the invention will be better understood when read in conjunction with the appended drawings. For the purpose of illustrating the invention, there are shown in the drawings specific embodiments. It should be understood, however, that the invention is not limited to the precise arrangements and instrumentalities of the embodiments shown in the drawings.

FIGS. 1A-1D depict a non-limiting illustration of an apparatus of the invention. FIGS. 1A-1B are diagrams of an apparatus in which a radar beams to the human subject's chest area to observe respiratory and heart beat activity. FIG. 1C is a diagram depicting the apparatus in motion. If the subject moves their body position or posture, the apparatus detects the movement, moves to a new location and redirects the radio beam to maintain proper orientation, targeting the chest area. FIG. 1D is a diagram of the radar navigator apparatus showing that the apparatus has full roll, pitch and yaw control with 360° of freedom using three motors ($M_1$, $M_2$ and $M_3$) to control the antennas' position and beaming directions.

FIG. 6A depicts vibration sources that affect the signal detected by the invention. FIG. 6B identifies the different areas of the chest that are tagged by the apparatus.

FIGS. 7A-7C show the diagrams of the scanning process when the user is sleep at different postures. The bottom figures show the energy of the signal at vital frequency band after scanning process corresponding to human sleep posture.

FIG. 12A is a graph of the breathing volume measurements of a respiratory disorder-free adult male subject. FIG. 12B is a graph of the breathing volume measurements of an adult female subject who suffers from mild snoring. FIG. 12C is a graph of the breathing volume measurements of a male child subject who suffers from mild hypopnea. The flat top breathing cycles in FIGS. 12B-12C denote a decrease in volume that can be used to diagnose breathing disorders by a clinical doctor.

FIG. 16A is a diagram illustrating a comparison (top sectional view) of existing chest displacement models and the proposed omni-directional deformation model. An omni-directional model (right) provides a closer approximation of the natural chest displacements within the patient's chest during the respiration process when compared to an orthogonal model (left). FIG. 16B is a scheme showing an overview of the proposed approach to reconstructing the patient's chest surface in real-time. Each of the identified steps must be recalculated for each frame during the monitoring process. This provides an active representation of the patient as they are monitored and the resulting surface deformations closely illustrate the patient's breathing state.

FIG. 17A is a diagram of clipped skeletal structures provided by the Kinect-2 with the present associated clipping cylinder. FIG. 17B is the depth-image bit history within the clipped region is utilized for removing depth measurement fluctuations belonging to the patient's chest surface.

FIG. 19A is an image of neck-edge points determined by a radial search from the neck joint position. FIG. 19B is a diagram showing the application of the planar hole fill algorithm within the calculated convex hull providing a uniformly closed clip region. FIGS. 19C-19D are images of chest reconstructions for two independent states: (FIG. 19C) inhale state and (FIG. 19D) exhale state. While wearing a normal shirt, the deformation patters of the patient's chest are still visible. FIG. 19E is an image showing the highlighted cross-sectional difference between the inhale and exhale states.

FIG. 20 is a scheme outlining the procedure of the training process to obtain non-linear correlation function between mesh volume estimated by camera and actual breathing volume collected by ground-truth device (spirometer).

FIG. 25 is an experimental setup for detecting occluded skeletal joints that define a patient's posture with occlusions from standard bedding. The image shows the proposed thermal-depth fusion skeletal estimation prototype that generates and reconstruct the 3D thermal distribution of the patient's occluded posture.

FIGS. 26A-26D are a set of images of skeletal posture estimations from recent techniques from the Microsoft Kinect, Primesense OpenNI (a, c), and improvements (b, d) reported by M. Ye et al., (IEEE ICCV, 2011, pp. 731-738.) that utilize depth-imaging to accurately identify joint positions in non-occluded applications. These methods have been further refined and extended with the introduction of newer depth-imaging devices such as the Microsoft Kinect2.

FIG. 27A illustrates an ideal non-occluded thermal image but illustrates non-uniform thermal distribution of a patient's thermal signature. FIG. 27B provides an illustration of heat marks left by a patient's arm movements. FIG. 27C illustrates thermal ambiguities of the patient during motion. FIG. 27D illustrates the patient's residual heat left when the patient has been removed.

FIG. 28A illustrates a discrete approximation of the patient's volume. FIG. 28B provides an illustration of the mapping between a voxel representation (black dots) of this volumetric data and the ground-truth skeletal estimate of the posture (illustrated as a set of joints and associated bones).

FIGS. 32A-32H are images of thermal surface point-cloud acquisition. The sequence of images illustrate the data collected from both the Microsoft Kinect2 and Flir C2 thermal devices to obtain thermal and surface point-cloud data. FIGS. 32A-32D illustrate the collection of the infrared, depth, thermal, and thermal surface respectively for a non-obscured view of the patient. FIGS. 32E-32H illustrate this data sequence for the same supine skeletal posture with an occlusion material present. Surface details provided by depth imaging (FIG. 32F) fail to provide a reliable means of estimating skeletal joints. Identifying hand joint positions in FIGS. 32E and 32F is extremely difficult. Using the proposed ground-truth estimation, it can be asserted known joint positions through occluding materials.

FIG. 34A illustrates the hierarchy root and the propagation directions and FIG. 34B illustrates the limitation of the propagation by the surrounding pointcloud and associated thermal intensities of the depth points.

FIGS. 36A-36D are images showing volumetric a thermal model process overview. FIG. 36A depicts the raw thermal cloud. FIG. 36B depicts the enclosed region of this cloud. FIG. 36C shows the generated internal thermal distribution of the patient. FIG. 36D provides the result of both the reconstruction and the thermal propagation through the enclosed volume. The thermal distribution in FIG. 36D was then provided to the training algorithm with an associated skeletal estimation.

FIG. 37A represents the discrete TEGI map of the sphere surface that contains the thermal contribution of two points. FIG. 37B illustrates the TEGI in 3D space with the two contributing points. FIG. 37C provides a rendering of the TEGIs within the sphere hierarchy used to show the thermal propagation from the surface scan.

DETAILED DESCRIPTION OF THE INVENTION

Figures 2A, 2B:
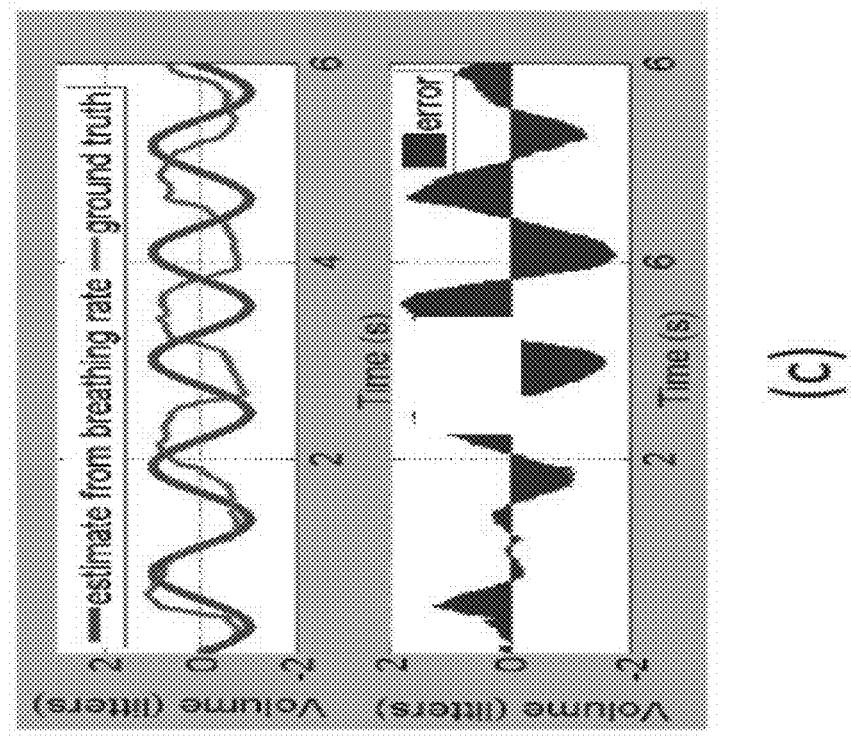
FIGS. 2A-2C illustrate the non-uniformity of a human chest in contrast with a uniform surface, such as that of a cylinder. This non-uniformity poses an obstacle to approximating breathing volume. Given the same volume change, all points on the cylinder will move with the same distance. In contrast, when a normal person inhales or exhales a certain volume, the xiphoid process area moves with a smaller amplitude compared to the movement of the right chest or left chest area.

In certain aspects, the invention provides an apparatus that allows for measuring and monitoring the breathing volume of a subject from afar over a period of time. In certain embodiments, the apparatus comprises a volume estimator device that measures the breathing volume of the subject through the use of radio waves.

In other aspects, the invention provides a method of measuring and monitoring the breathing volume of a subject from afar over a period of time. In certain embodiments, the methods of the invention can be used to diagnose a respiratory disease or disorder in the subject.

In still other aspects, the invention provides a kit comprising an apparatus of the invention.

In certain non-limiting embodiments, the system of the invention relies on a phase-motion demodulation algorithm that reconstructs minute chest and abdominal movements by analyzing the subtle phase changes that the movements cause to the continuous wave signal sent by a 2.4 GHz directional radio. These movements are used to calculate breathing volume, where the mapping relationship is obtained via a short neural-network training process. To cope with body movement, the system tracks the large-scale movements and posture changes of the person, and moves its transmitting antenna accordingly to a proper location in order to maintain its beam to specific areas on the frontal part of the person's body. It also incorporates interpolation mechanisms to account for possible inaccuracy of the posture detection technique and the minor movement of the person's body. The system of the invention has been shown, through a user study, to be able to accurately and continuously monitor user's breathing volume with a median accuracy from 90% to 95.4% even in the presence of body movement. In certain embodiments, the monitoring granularity and accuracy allows for diagnosis uses by a clinical doctor.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described. As used herein, each of the following terms has the meaning associated with it in this section.

Generally, the nomenclature and procedures used herein are those well-known and commonly employed in the art.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

An "algorithm" is a set of finite logical instructions or a method that can be expressed in a finite amount of time and space and in a well-defined formal language for calculating a function. An algorithm usually has an initial state and an initial input that, after the execution of a set of instructions and/or calculations, yields an output. An algorithm can be carried out as part of a computer program, or can be carried out in the absence of a computer.

"Apnea" or "apnoea" refers to the suspension of external breathing. During apnea, there is no movement of the muscles of inhalation and volume of the lungs remains unchanged. "Sleep apnea" is a sleeping disorder characterized by pauses in breathing or instances of shallow breathing during sleep.

As used herein, the term "breathing volume" means the amount of air travelling through the breathing airway into the lung during inspiration and out of the lung during expiration.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

"Hypopnea" or "hypopnoea" is a disorder that involves episodes of overly shallow breathing or an abnormally low respiratory rate. During sleep, hypopnea is classed as a sleeping disorder. It may cause a disruption in breathing that causes a drop in blood oxygen level, leading to a number of adverse effects.

As used herein, the phrase "radar occlusion" refers to the situation where the radio frequency beam is at least partially blocked by a human body part (or another object in the examination area) and thus cannot reach the area of interest on the human chest.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Breathing Volume Measuring Apparatus

The present invention relates to an apparatus for the measurement and monitoring of the breathing volume of a subject from afar. In certain embodiments, the device comprises a volume estimator, a navigator device, and optionally a trainer device. In certain embodiments, the volume estimator comprises a radio wave emitter and a radio wave receiver. In other embodiments, the volume estimator further comprises a camera or any other recording device. In certain embodiments, the navigator device comprises a posture detector and a navigation controller. In certain embodiments, the trainer device comprises a spirometer.

In certain embodiments, the radio wave emitter emits single tone continuous radio waves. In other embodiments, the radio wave emitter emits a single tone continuous radio waves at about 2.4 GHz. However, one skilled in the art will understand that the radio wave emitter of the invention can utilize single tone continuous radio waves of a wide range of frequencies. In yet other embodiments, the radio wave receiver collects and outputs data at a sampling rate ranging from about 1 kHz to about 100 kHz. In yet other embodiments, the radio wave emitter has a beam width of about 20 degrees. In yet other embodiments, the sampling rate of the radio wave receiver is selected from a range of rates, depending on the specification of the receiver and the capacity of the storage computer.

In certain embodiments, the volume estimator comprises a camera that records visible light (about 400 to about 700 nm) and/or the infrared light (about 700 nm to about 1 mm). In other embodiments, the camera is a depth-imaging camera.

In certain embodiments the posture detector comprises a radar transmitter, a radar receiver, three motors, and a computer.

In certain embodiments, the volume estimator, which comprises the radio wave emitter and the radio wave receiver, is mounted on a mechanical motion control system. In certain embodiments, the mechanical motion control system is controlled by a computer in real-time based on feedback from the navigator device. In other embodiments, the mechanical motion control system is capable of rotating the radio wave emitter and radio wave detector in a full 360° arc vertically and horizontally.

In certain embodiments, the mechanical motion control system is mounted on a track system. In certain embodiments, the mechanical control system is capable of lateral motion on the track system, across the chest of the subject from shoulder to shoulder. In certain embodiments, the mechanical motion control system is capable of horizontal motion on the track system, across the length of the subject from head to toe. In certain embodiments, the mechanical motion control system is mounted on a bed or similar horizontal platform on which a subject can lay horizontally.

In certain embodiments, the trainer device further comprises a camera and a microphone. In other embodiments, the camera is a camera capable of recording in the visible light range and/or the infrared light range.

Methods

The present invention further relates to methods of measuring and monitoring the breathing volume of a subject. The method comprises directing a continuous radio wave from a radio wave emitter at the chest of a subject, detecting the radio waves reflected off of the chest of the subject over time using a radio wave receiver, collecting the radio wave measurement data collected by the radio wave receiver and applying a mathematical formula to convert the measured change in frequency of the collected radio signals into a measurement of the change in volume of the subject's chest.

In certain embodiments, the method further comprises obtaining a breathing volume measurement using a spirometer and correlating the radio wave measurements with the volume measured using the spirometer. The spirometer records the breathing volume of the subject for a period of time at the beginning of the method and a computer correlates the measurements obtained by the radio wave detector with the volume measured by the spirometer. This serves to calibrate the radio wave detector measurements. After a period of time, the spirometer is removed and the breathing volume measurements are then obtained from the radio wave detector which has been calibrated.

In certain embodiments, the method further comprises monitoring any changes in the subject's posture or position and moving the radio wave emitter and radio wave receiver accordingly in order to keep the continuous radio wave directed at the subject's chest. In other embodiments, the change in the subject's posture or position is detected when the radio wave receiver no longer receives interfering signals from the subject's heartbeat or respiration. In other embodiments, if the subject has changed its posture or position, the radio wave emitter and radio wave receiver move to a position wherein the radio wave receiver begins receiving interfering signals from the subject's heartbeat or respiration.

When the posture change is detected during sleep, the system begins a scanning process to detect human posture. The computer sends a command to the sliding motor to carry the radar from one side to another side on the rail above of the bed surface. During this time, the transmitter sends out a wireless signal, in a non-limiting example at 2.4 GHz, while the receiver captures the reflected off component of the signal. The data collection process is done when the radar reaches the opposite side of the bed. The computer then runs an algorithm with the collected wireless samples and infers the human posture using an algorithm. The computer then sends another command to the three motors to move and navigate the radar transmitter to a new orientation and location that is orthogonal to the plane of the subject's chest.

In certain embodiments, the reflected radio wave measurements are detected at a number of localized points on the chest of the subject. In other embodiments, the reflected radio wave measurements are detected at any of nine localized points on the chest of the subject. By measuring at a number of localized points, it allows for measurements to be taken at alternative points if certain points on the chest are obstructed.

In certain embodiments, the method further comprises detecting interfering signals from the subject and applying an algorithm to compensate for these signals. In certain embodiments, the interfering signals may be caused by a source selected from the group consisting of movement of the body of the subject, vibration due to the respiration of the subject, vibration due to the heartbeat of the subject.

In certain embodiments, the method further comprises detecting changes in breathing volume of the chest of the subject using a depth-imaging camera. In certain embodiments, the depth-imaging camera allows for imaging of a subject's chest using infrared imaging. In certain embodiments, the tidal volume of the chest of the subject can be tracked using an omni-directional deformation model. In other embodiments, a breathing volume measurement is obtained using a spirometer and the change in breathing volume of the subject's chest using the depth-imaging camera is correlated with the breathing volume measurements recorded by the spirometer. In other embodiments, the change in breathing volume of the subject's chest determined using the depth-imaging camera is correlated with the measurements obtained with the radio wave detector.

In certain embodiments, the subject is sleeping. In certain embodiments, the subject is a mammal. In other embodiments, the subject is a human.

The present invention further provides a method of diagnosing a respiratory disease or disorder wherein a medical professional applies one of the above described methods to measure and monitor the breathing volume of a subject in order to make a diagnosis. In certain embodiments, the respiratory disease or disorder is one or more selected from the group consisting of hypopnea, apnea, sleep apnea, snoring, insomnia, obstructive sleep apnea, central sleep apnea, child sleep apnea, infant sleep apnea, pregnancy induced sleep apnea and sleep related groaning.

Kits

The present invention further provides a kit comprising the apparatus of the invention and instructions for the operation of the apparatus. In certain embodiments, the kit further comprises a computer for processing the data collected by the apparatus.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in experimental conditions with art-recognized alternatives and using no more than routine experimentation, are within the scope of the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials and Methods: Formulas and Algorithms Formula (1):

$$T(t) = \cos(\omega t) \tag{1}$$

t is time; T(t) is the outgoing signal at time t; $\omega$ is the frequency of the signal Formula (2)

$$R(t) = \cos\left(\omega t - \frac{4\pi d_0}{\lambda} - \frac{4\pi m(t)}{\lambda}\right) \tag{2}$$

t is time; R(t) is the received signal at time t; $d_0$ is the distance between the radar and the subject's chest; m(t) is the chest movement function representing the chest position at time t; $\omega$ is the frequency of the signal; $\lambda$ is the wavelength of the signal Formula (3)

$$B(t) = \cos\left(\frac{4\pi d_0}{\lambda} + \frac{4\pi m(t)}{\lambda}\right) + \cos\left[\left(2\omega t - \frac{4\pi d_0}{\lambda} - \frac{4\pi m(t)}{\lambda}\right)\right] \tag{3}$$

t is time; B(t) is the output signal at time t, which is the multiplication product of T(t) and R(t); $d_0$ is the distance between the radar and the subject's chest; m(t) is the chest movement function representing the chest position at time t; w is the frequency of the signal; $\lambda$ is the wavelength of the signal Formula (4)

$$F(t) = \cos\left(\frac{4\pi d_0}{\lambda} + \frac{4\pi m(t)}{\lambda}\right) \tag{4}$$

t is time; F(t) is the filtered output signal at time t; $d_0$ is the distance between the radar and the subject's chest; m(t) is the chest movement function representing the chest position at time t; $\lambda$ is the wavelength of the signal $$\Delta m \approx \frac{\lambda}{4\pi}\left(\arctan\left(\frac{F_Q(k)}{F_I(k)}\right) \cdot \arctan\left(\frac{F_Q(k-1)}{F_I(k-1)}\right)\right) \tag{5}$$

Formula (5):

D m is chest movement between two consecutive samples; F(k) and F(k−1) are F(t) at time k and k−1 respectively; I and Q represent the I and Q channels of F(t); 2 is the wavelength of the signal

---

Algorithm 1: Basic Volume Estimation Algorithm

---

Input: $F_I(k)$ and $F_Q(k)$ /* Received samples */
  S, areaID, L, $N_c$(areaID) /* which are number of samples, chest area ID, moving window size, and trained neural network for areaID, respectively/
Output: Estimated breathing volume vector V*[1 : S]
1 F'$_I$ ← DC filtered of $F_I$; and F'$_Q$ ← DC filtered of $F_Q$ 2 CZ[1 : n] ← Find cross zero indexes of arctan $\left(\frac{F'Q}{F'I}[1:S]\right)$, 3 for j =1 to n − 1 do 4 V [CZ(j) : CZ(j+1)] ← $N_c$ (areaID, arctan $\left(\frac{F'Q}{F'I}\right)$
[CZ(j) : CZ(j+1)])

5 V* [1 : S] ← V [CZ(1) : CZ(n)]

---

Algorithm 1 is used to infer breathing volume from received wireless signal when there is no body movement detected:

Step 1: The computer gathers the input data $F_I$ and $F_Q$, and filters the environment noise as well as removes DC offset. A bandpass filter is often used to serve this purpose.

Step 2: The cross zero indexes is defined from the filtered data to identify where the signal pass the median, which corresponds to the fact that the chest movement passes the middle point between inhale and exhale.

Step 3 to step 5: The filtered cross zero data is then used to infer breathing volume though a non-linear correlation function ($N_c$) between chest movement and breathing volume obtained during training process. Note that during scanning the computer produced a non-linear correlation function between chest movement and breathing volume. With this non-linear correlation function, each movement from inhale to exhale and vice versa is inferred to a certain amount of breathing volume.

---

Algorithm 2: Training for Movement-to-Volume Neural Network

---

Input: $F_I(k)$ and $F_Q(k)$ /* Received samples */
    gridSize /* Number of chest areas */
    N /* Total number of samples collected per area */
Output: Trained neural network $N_c$ [i] for all areas with i ∈ [1, gridSize]
1 for each area do
2   $V_G$ [1 : N] ← Volume measured by spirometer for area i
3   $f_L$ ← 0.2Hz; $f_H$ ← 1.8Hz; /*Cut-off frequencies */
    $F'_I$ ← DC filtered of $F_I$; and $F'_Q$ ← DC filtered of $F_Q$ 4
$$F^*[1:N] \leftarrow \text{Band pass filter of}\left(\arctan\left(\frac{F'Q}{F'I}\right)[1:N]\right)$$

5   Align $F^*$ with $V_G$ using peaks and cross zero points
6   Resampling $F^*$ to match with $V_G$
7   $[CZ_{F^*}[1:n']]$ ← Find cross zero indexes $F^*$
8   Segment $< F^*, V_G >$ pairs using cross zero indexes
9   Obtain $N_c$ (areaID) /* trained network for all pairs using Bayesian back-propagation neural network */
10  Navigate the antennas to the next area
11  return $N_c$

---

Algorithm 2 is used to infer the non-linear correlation function ($N_c$) between chest movement and breathing volume:

Step 1: The following step is repeated over different area on the human chest. The number of areas depends on subject chest size.

Step 2: The system collects data from the spirometer. At the mean time, the radar collects data at radar receiver and filtered them as in Step 2 to Step 4.

Step 5: The data from spirometer and radar are aligned to each other.

Step 6: The data from radar is then resampled to that of the same as spirometer.

Step 7: The zero crossing of the data from spirometer and radar are then obtained. The data are then segmented by those zero crossing points.

Step 8: The segments from radar data and spirometer are then mapped to pairs.

Step 9: Those segments are put to a Bayesian back-propagation neural network training to obtain the non-linear correlation function representing the relationship of those two data.

---

Algorithm 3: Posture Estimation

---

Input :
    $f_S$: /* Sampling rate */
    $F_I(k)$ and $F_Q(k)$ /* Received samples */

---

Algorithm 3: Posture Estimation

---

Output: moving radar to new location
  1. $f_L \leftarrow \sqrt{F_I^2(k)+F_Q^2(k)}$
  2. $f_L$ ← 0.2Hz; $f_H$ ← 1.8Hz;
  3. E[1:n] ← Calculate power distribution of the signal during scanning (window size = 5s)
  4. ∃E[k] ← Kadan Algorithm (E[1,n])
  5. Mapping k to location of antenna on the arc
  6. Move data to new location.

---

Algorithm 3: A computer implemented method of estimating posture of a subject:

Step 0: Move radar from one side to another side along the bed while radar transmitter sends out wireless signal at 2.4 GHz and receiver captures the reflected component.

Step 1: Collect received signal strength of the wireless signal.

Step 2: Filter out the noise. Keep the signal at vital sign frequency (from 0.2 to 1.8 Hz).

Step 3: Calculate the power distribution of the signal during scanning (window size=5 secs).

Step 4: Using Kadane Algorithm to find the maximum power of the signal during scanning.

Step 5: Move to the new location where maximum power of vital signal reflected signal is observed.

---

Algorithm 4: Point Localization

---

Input: $F_Q'$, $F_I'$ /* Received Signal */
    TF(F[1:16] → $F_n$[1:16])
Output
1. $f_L$ ← 0.2Hz; $f_H$ ← 1.8Hz;
2. $F_I'$ ← DC filtered of $F_I$; and $F_Q'$ ← DC filtered of $F_Q$ 3.
$$F^* \leftarrow \text{Band pass filter of}\left(\arctan\left(\frac{F_Q'}{F_I'}\right)[1:N]\right)$$

4. F[1:16] ← Feature extraction($F^*$)

-continued

Algorithm 4: Point Localization

5. TF = Normalize F[1:16]
6. Area's ID ← k-NN Classify (F[1:16], TF)

Algorithm 4: A computer implemented method of estimating chest position of a subject:

Training: Before the sleep study, the radar beams to different areas on the human chest. The transmitter sends out wireless signal and the receiver captures the reflected component. The signals captured at different areas are then extracted into 16 features/each area.

Real-time monitoring: During the sleep study, when the radar beam to a human chest, the received signal is also extracted into 16 features in real time. Those new features are compared with the ones obtained during training to find a match. This process will provide the ID of the chest where the radar is beaming to Algorithm 5: WiSpiro Breathing Volume Estimation Input: $data_{RD}$ ← data from radar
output:
filterRD ← Band pass filter ($data_{RD}$), $f_L$ = 0.2Hz, $f_H$ = 1.8Hz.
Detecting human activities change based on filterRD
 1. If no body movement is detected then
 2.   Run Algorithm 1
 3. If large body movement is detected then
    Run Algorithm 3
 4. If small body is detected then
 5.   Run Algorithm 4

The missing data is filled up by spline interpolation technique. The key idea is to generate the new data point based on the data of neighbors' area.

Algorithm 6: Chest Mesh Volume Extraction

Input: $D_s(t)$ - n-Sampled Depth-image
   S(t) - Patient Skeletal State
Output: $V_m(t)$ - Iso-surface Mesh Volume
Foreach $p_{ij} \in D_s(t)$ do
   if $p_{ij} \in c$ then
      C(t) ← $p_{ij}$
   End
B(t) ← PlanarProjection ($\hat{b}$, α, C)
N(t) ← ConvexPlanarProjection (neck_joint, $E_c(t)$)
W(t) ← ConvexPlanarProjection (waist_joint, $E_c(t)$)
P(t) ← ∪ C(t) ∪ B(t) ∪ N(t) ∪ W(t)
S(t) ← Iso-Surface Extraction (P(t))
$V_m(t)$ ← SignedTetrahedralVolume (S(t))
Return $V_m(t)$ Algorithm 7: Infrared training algorithm Input: $V_m(t)$
   $V_s(t)$ /* Spirometer */
Output: $F_c$ - correlation function of $V_m(t)$ and $V_s(t)$
If bMonitoring then
   Filter $V_m(t)$ (Band-pass filter with cut-off frequencies)
   Mean removal $V_m(t)$
   Align starting point of $V_m(t)$ and $V_s(t)$
   Segment $V_m(t)$ and $V_s(t)$ into n equal segments
   Resample $V_s(t)$
   Align $V_m(t)$ and $V_s(t)$ Obtain a non-linear correlation function $F_c$ of $V_m(t)$ using neural network.
End
Return $F_c$ Example 1: Apparatus Overview As demonstrated herein, a prototype of the device of the invention was built, and its potential was demonstrated through a user study where it accurately and continuously monitored a user's breathing volume with a median accuracy of 90% even in the present of body movement. The results also showed that the granularity of the estimation was useful for sleep study analysis. Certain aspects of the invention are as follows:

Theoretical and practical design of a breathing volume estimator. A model for the effects of chest movement and posture change on radar signals was developed in terms of phase and signal strength. A calibration technique inspired by neural network back propagation training model was adopted to calculate breathing volume from the chest movement.

A set of algorithm was developed to address challenges caused by body and body part movement. Posture detection and point localization techniques were developed to guide the antenna movement and orientation when movement occurred. To improve the correctness of inferring breathing volume from chest movement, an interpolation technique was introduced to integrate with the point localization output that helps correcting the estimation results.

Implementation and evaluation show the feasibility, performance, and potential of the system. Five algorithms including chest movement reconstruction, posture estimation, point localization, and volume interpolation were implemented on the prototype. Experiment were conducted on 5 users for 300 minutes. The results showed high estimation accuracy after integrating of the above-mentioned optimization techniques.

In certain embodiments, the device of the invention is able to unobtrusively and autonomously estimate the breathing volume with fine granularity at sub-breathing cycle level even with the presence of random body movements. The device and methods of the invention address certain issues, such as the nature of breathing activities and non-uniformed shape of human chest areas, body movement, and the nature of radio signals.

Non-Uniform Movement of Body Areas During Breathing.

Figure 2C:
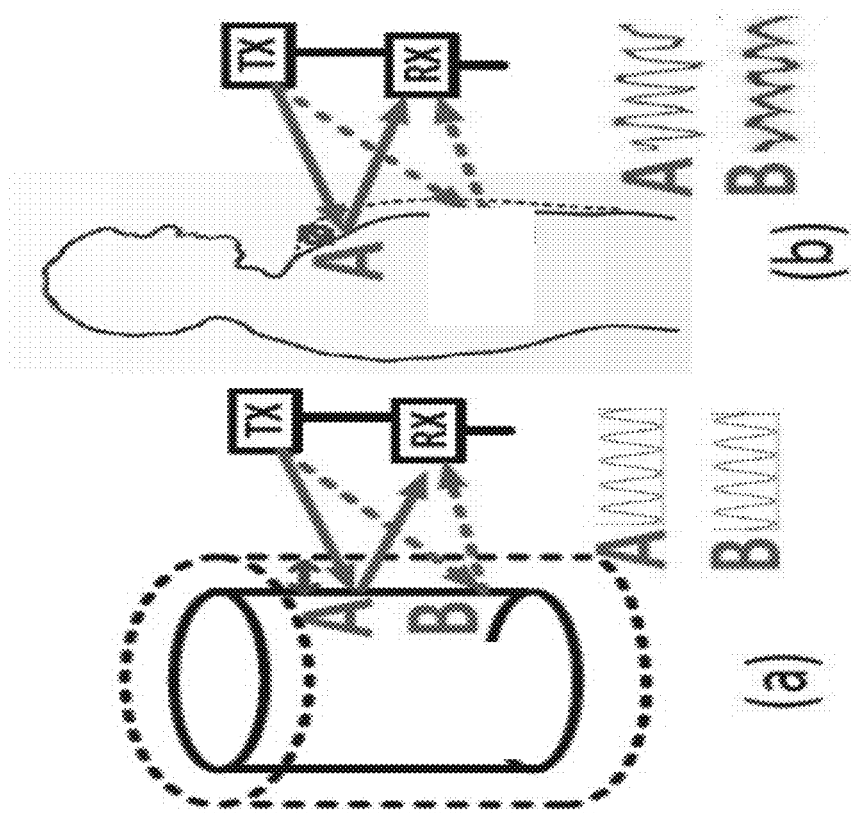

Due to the non-uniform physical shape of human rib cage and upper body, the movement of different areas on human chest caused by respiratory activities are also non-uniform. FIGS. 2A-2C illustrate the non-uniformity of a human chest in contrast with a uniform surface of a cylinder. Given the same volume change, all points on the cylinder move with the same distance. On the other hand, when a normal person inhales or exhales a certain volume, the xiphoid process area moves with a smaller amplitude compared to the movement of the right chest or left chest area. This implies that the relationship between chest movement and breathing volume is non-uniform across different chest areas. Because of this property, even a minor non-respiratory movement of the body could make the antennas point to a wrong location that could cause significant volume estimation error. In certain embodiments, at any given time, a device of the invention distinguishes the area that it is beaming to in order to estimate breathing volume with high accuracy. In other embodiments, highly directional radar transceivers are used, and a posture detection algorithm is used to detect the cross section vector of human chest movement. Further, an autonomous motion control system that directs the antennas towards a fixed anchor area (e.g. heart area) is used to monitor human chest movement.

Possible Blockage of Radio Signals.

During sleep, a subject might change her posture or move her body part to react to common environmental events such as random loud sound, change of temperature, humidity, and light condition, and so forth. These posture changes or body part's movements (e.g., arms) might block the anchor area (e.g., heart area) from the light-of-sight of the antennas. In certain embodiments, a device of the invention finds an alternative area that can be seen clearly by radar. It then infers the breathing volume based on the movements captured on that area and the relationship between that movement and breathing volume learned in the one-time training process at the beginning.

Non-Linear Relationship Between Chest Movement and Breathing Volume.

In certain embodiments, breathing volume can be obtained from the rate by assuming that the breathing volume has a form of V=A sin ωt, where V is the breathing volume, A is the amplitude that could be obtained by calibration, and ω=2πf (f is the breathing rate). However, this model misses the inhaled and exhaled patterns of breathing activities. As demonstrated herein, an experiment was conducted to evaluate the possibility of this approach. The results showed that the actual breathing volume does not follow a perfect sinusoidal form in each cycle. However, the imperfect curve is of interest to medical practitioners because it reflects the subject's breathing patterns. The respiration volume information is included in the very minor phase shift of the reflected signal. This is in sharp contrast with respiration rate, which only needs to extrapolate peak frequency of the respiration curve. To address this problem, a model was used to map a device's received signal pattern to chest movement, and then map the movement to fine-grained breathing volume value according to a neural network model trained for different chest positions.

Figure 3:
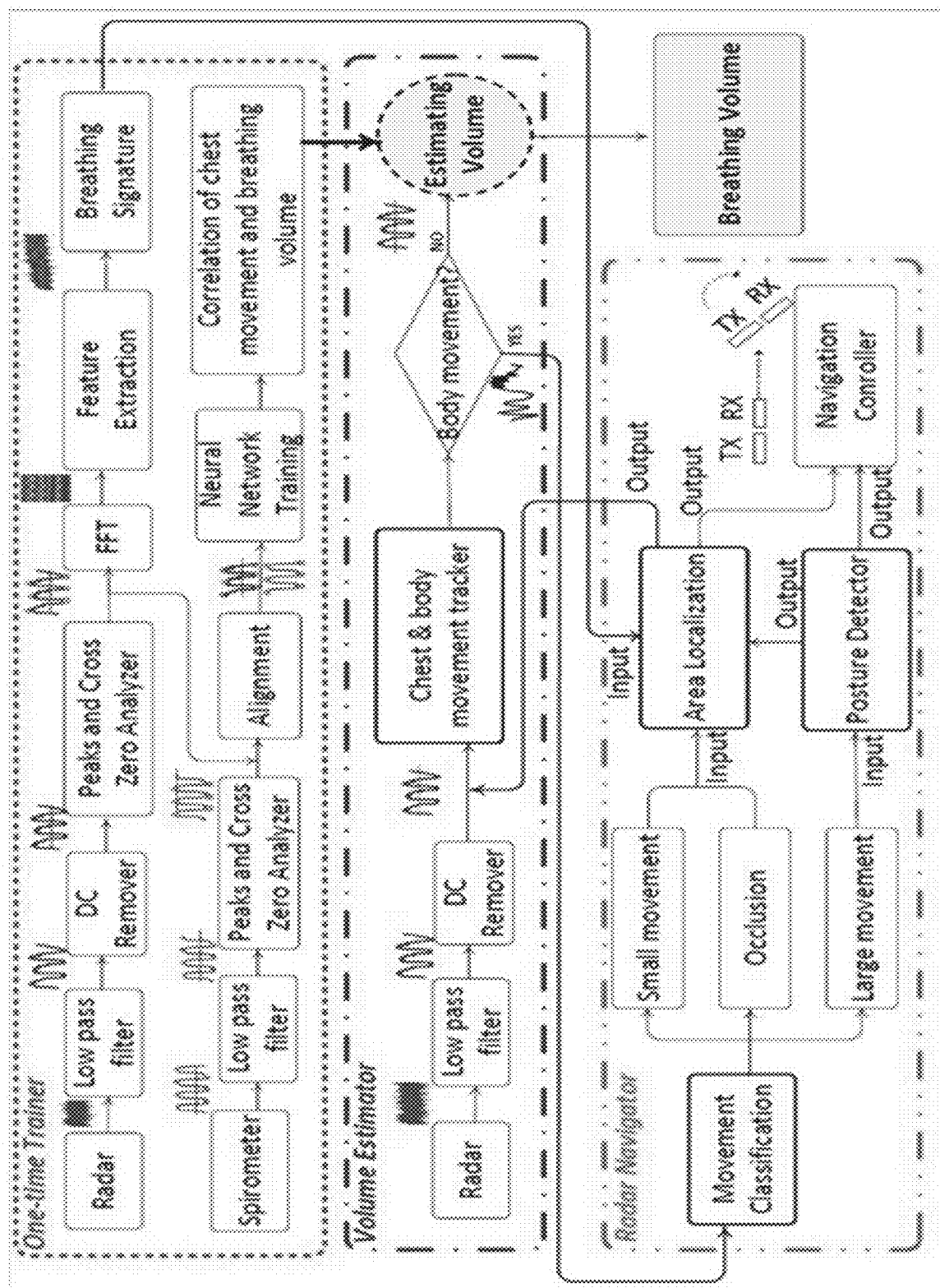
FIG. 3 illustrates an architectural overview of the apparatus.

As depicted in FIG. 3, the apparatus includes three main components: a volume estimator, a navigator device and a trainer device.

Volume Estimator:

The apparatus utilizes a decoding technique that extracts a subject's frontal movement due to breathing, heart beat and random body movement from reflected radio signals. The apparatus continuously tracks the minute frontal body movement by analyzing the phase-shift and the signal strength of the signal captured by the receiving radar. This movement information is then combined with prior knowledge, obtained through the trainer device, to estimate fine-grained breathing volume.

Navigator Device:

The apparatus relies on a radar navigator to track the random movement of the subject that could come from movement of the limbs, shoulders, other body parts or the entire body during sleep. Using the phase-shift and signal strength information gathered by the volume estimator as inputs, the navigator detects large and small scale body movement. The navigator estimates the sleeping posture of the subject and moves the antenna accordingly to redirect the radio beam to the subject's chest upon detecting body movement. Furthermore, it executes an area localization algorithm to identify the area on the chest to which the radio beam is pointing. This area information allows the navigator to not only fine-tune its antenna orientation to beam to the subject's heart area, but also informs the volume estimator which training data should be used for calculating the volume; the same breathing behavior can cause different areas to move differently. The navigator also detects occlusions, e.g. if the a segment of the chest area is obstructed by an arm. In such case, the navigator redirects the volume estimator to an alternative area of the chest to continue the monitoring process.

Trainer Device:

In one aspect, a training step is required to establish the correlation between human chest movement and breathing volume, because this correlation depends on chest size, age, breathing patterns, and so on. Using a neural network, the trainer establishes a relationship between body movement and beaming area with breathing volume as measured by a spirometer. Given an instance of chest movement at a known area on human chest as an input, the output of the function is a corresponding breathing volume. In another aspect, the system needs to know exactly where it is pointing, so that it uses the correct correlation function for estimating breathing volume from the chest movement. For that, the trainer provides characteristics of the reflected signal when the volume estimator focuses on different areas on the subject's chest. These characteristics are mapped into features. By comparing the features of the signal with those of the signals from trained areas, the system can infer the location at which radar is pointing.

Example 2: Theoretical Analysis of Movement Reconstruction

A apparatus transmitter of the invention continuously emits a single tone signal with frequency ω, and uses a directional antenna to beam the signal towards the subject's chest. When hitting the subject's chest, part of the signal is eventually captured by a directional receiver radio. The single-tone continuous wave T(t) is formulated as:

$$T(t) = \cos(\omega t) \tag{1}$$

Let $d_0$ be the distance between radar and human chest, m(t) be the chest movement function representing the chest position at time t, then $d(t)=d_0+m(t)$ is the effective distance between the radar and human chest at any given chest position at time t. The received signal, namely R(t), can be written as:

$$R(t) = \cos\left[\omega\left(t - \frac{2d(t)}{c}\right)\right] = \cos\left[\omega\left(\frac{2d_0 + 2m\left(t - \frac{d(t)}{c}\right)}{c}\right)\right]$$

In the above equation, $$\frac{d(t)}{c}$$

is negligible since d(t) is 10 orders of magnitude smaller than the speed of light c. Therefore $$m\left(t - \frac{2d(t)}{c}\right) \approx m(t)$$

and, R(t) can be written as:

$$R(t) = \cos\left[\omega\left(t - \frac{2d_0}{c} - \frac{2m(t)}{c}\right)\right] \quad (2)$$

$$R(t) = \cos\left(\omega t - \frac{4\pi d_0}{\lambda} - \frac{4\pi m(t)}{\lambda}\right)$$

As shown in Eq. (2), the received signal R(t) includes a high frequency component (i.e., at transmitted frequency ω) and a low frequency component caused by chest movement m(t). In certain embodiments, the low frequency component, which is pertinent to volume estimation, is extrapolated. The radar mixes its received signal R(t) with the originally transmitted one T(t) using a simple mixer. In an ideal mixer, the output signal, called B(t), is the multiplication of T(t) with R(t) which are the two inputs to the mixer. T(t) is fetched into the mixer via its local oscillator (LO) port. Different frequency components of the output signal from the mixer is calculated as:

$$B(t) = \cos\left(\frac{4\pi d_0}{\lambda} + \frac{4\pi m(t)}{\lambda}\right) + \cos\left[\left(2\omega t - \frac{4\pi d_0}{\lambda} - \frac{4\pi m(t)}{\lambda}\right)\right] \quad (3)$$

Now that the two signal are separated after passing through the mixer, the low frequency component can be retrieved by a simple low pass filter. The filtered signal, called F(t), is written as following:

$$F(t) = \cos\left(\frac{4\pi d_0}{\lambda} + \frac{4\pi m(t)}{\lambda}\right) \quad (4)$$

The apparatus estimates breathing volume only when the subject does not move. If a body movement is detected, the radar navigator takes control to adjust the antennas to beam to a correct position before restarting the breathing volume estimation process. When the body is static, the distance between the antennas and the subject's frontal areas $d_o$ remains fixed. Therefore, from Eq. (4), phase change between consecutive samples, F(k) and F(k−1), represents only chest movement due to vital signals including breathing and heart rate.

$$\arctan(F(k)) - \arctan(F(k-1)) \approx \frac{4\pi(m(k) - m(k-1))}{\lambda}$$

Let Δm be the chest movement between consecutive samples, then Δm=(m(k)−m(k−1)). If $F_c(t)$ and $F_Q(t)$ are the I and Q channels of F(t), respectively, then the above equation can be rewritten as:

$$\frac{4\pi \Delta m}{\lambda} \approx \arctan\left(\frac{F_Q(k)}{F_I(k)}\right) - \arctan\left(\frac{F_Q(k-1)}{F_I(k-1)}\right) \iff \Delta m \approx \frac{\lambda}{4\pi}\left(\arctan\left(\frac{F_Q(k)}{F_I(k)}\right) - \arctan\left(\frac{F_Q(k-1)}{F_I(k-1)}\right)\right) \quad (5)$$

Eq. (5) shows how chest movement is calculated from samples of received signal. The movement estimation is independent of $d_0$, which is base distance from chest to antenna.

Example 3: Volume Estimation Algorithm

Based on the prior analysis, an algorithm was designed to robustly demodulate fine-grained breathing volume from received signals. Several challenges need to be addressed in this process. In one aspect, the respiratory chest movement between two consecutive reflected signal samples is very small and is buried in minor phase change. In another aspect, it is difficult to detect phase changes given the various types of noise in the system which are introduced by reflection from background objects, multipath components, and signal leakage due to TX, RX hardware imperfection. In yet another aspect, the nonuniform movement of different body areas during breathing makes the correlation between area movement vs. breathing volume to be dependent on the area location. To overcome the above challenges, the regularity and quasi-periodic nature of chest area movement were exploited. In particular, an area is highly likely to move along the same direction, either inward (exhaling) or outward (inhaling), for a number of sampling cycles before the direction is changed. In certain embodiments, one cannot alter his or her breathing from inhale to exhale in one sampling cycle and then back. Moreover, the movement direction only changes when the subject changes from inhale to exhale, i.e., finishing one half of a breathing cycle. Thus, chest area movements within one half of a breathing cycle are identified and grouped for breathing volume estimation, for which per-sample breathing volume is inferred.

In addition, the noises are either reflected off rather stationary sources or from hardware leakage, and thus have either relatively low frequencies or frequencies following Gaussian distribution. Therefore, these noise can be removed with proper filtering mechanisms such as DC and bandpass filters. Further, a one-time neural-network-based training process is designed to mine the relationship between breathing volume and chest movement for each chest area. These area specific relationships are later used for volume estimation. Algorithm 1 summarizes the basic volume estimator which integrates these solution principles.

Signal Preprocessing.

The signal sequence received by the receiver has S samples which are in I and Q channels and acquired as described in Example 2. The series of $F_I(k)$ and $F_Q(k)$, k ∈[1:S] contains DC components caused by hardware leakage and quasi-stationary background which are removed by a moving-average DC filter. The filtered signal sequence, $F'_I(k)$ and $$F'_Q(k), \text{ are } F'_{I,Q}(t) = F'_{I,Q}(k) - \frac{1}{L}\sum_{i=0}^{L} |F'_{I,Q}(k-i)|,$$

in which L is the moving window size and k∈[1:S].

Half-Cycle Segmentation.

The filtered samples are then divided into n segments where n is the number of times that the phase of the signal, arctan ($F'_Q/F'_I$), crosses zero. By doing so, samples of the same breathing activity, either inhale or exhale, are grouped into the same segment. It also accommodates group with different size which mean breathing activity with different paces, such as a long inhale or short exhale.

Per-Segment Volume Estimation.

This step is to calculate the volume of each half-cycle segment. One important input of this step is the neural network that contains the relationship between a movement of a specific chest area and its corresponding breathing volume values. This network conducts the one-time training process that is presented in Example 4. Another key input is the ID of the chest location at which the antennas are beaming.

Example 4: Training the Neural Network for Movement-to-Volume Mapping

The apparatus is built on a physiological premise of the harmonic movement between the chest and lung expansion during breathing. That is, when the lung expanses due to inhaling, the chest is also expanding. Likewise, the chest is collapsing during exhale. This phenomenon is part of the training algorithm. This training process quantifies the relationship between chest movement and breathing volume of individual. It also takes into account the nonuniformity of the movement on different chest areas given the same breathing activity.

Figure 4:
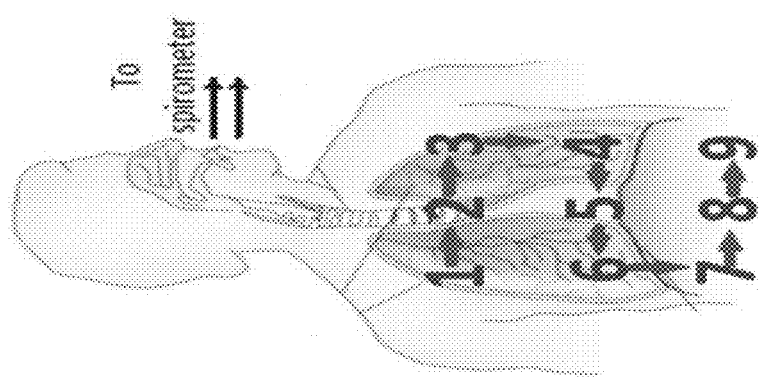
FIG. 4 is a diagram depicting the chest of a subject and the nine (9) areas that it can be divided into for analysis by an illustrative apparatus of the invention.

The movement-to-volume training is needed once, or at least once, or only once, for each subject. During this process, a subject is asked to lie down and breath normally into a spirometer. The breathing volume $V_G$ of the person is recorded. The patient's chest is spatially divided into sub-areas. Depending on the chest size and the beam width of the transmitting antenna, the number of areas, gridSize, is determined so that the antenna can beam to each area individually without overlapping to the others. Illustrated in FIG. 4, a chest is divided into 9 areas each of which is scanned sequentially by the antennas. For each area, $F_I$ and $F_Q$ signals are collected, along with the corresponding $V_G$. The training process is formalized in Alg. 2.

Example 5: Achievable Accuracy of Volume Estimator

A simple scenario was set up to verify the achievable accuracy of the technique and to identify possible optimization. The subject under test lied down on a bed and breathed normally for a period of 3 minutes, while his breathing volume was being monitored and estimated by both the apparatus of the invention and a spirometer (ground truth). At the beginning of the experiment, the person performs a 9-minutes long training, following the procedure in Example 4.

Figure 5:
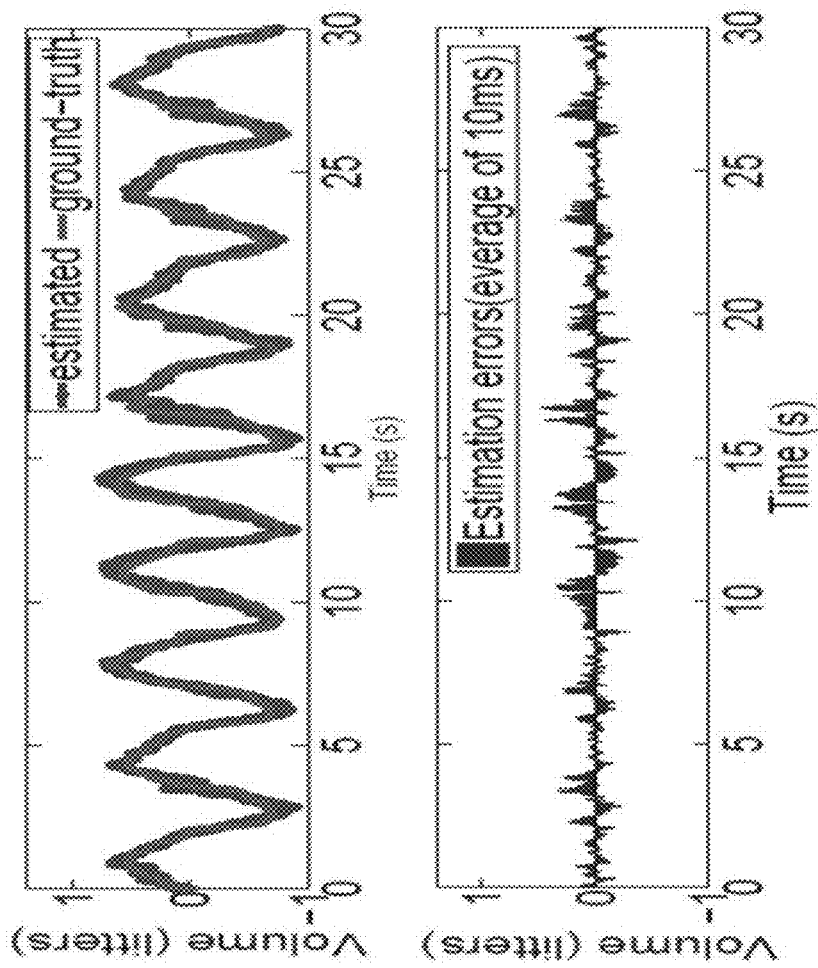
FIG. 5 is a set of graphs depicting the breathing volume estimated by the basic algorithm of the invention for a stationary person as well as the estimation error over a period of time.

FIG. 5 plots the estimated volume time series. The apparatus demonstrated a small mean error of 0.021 litters, maximum error 0.052 litters, and standard deviation 0.111 litters across the testing period.

Example 6: Posture Estimation

Figure 8A:
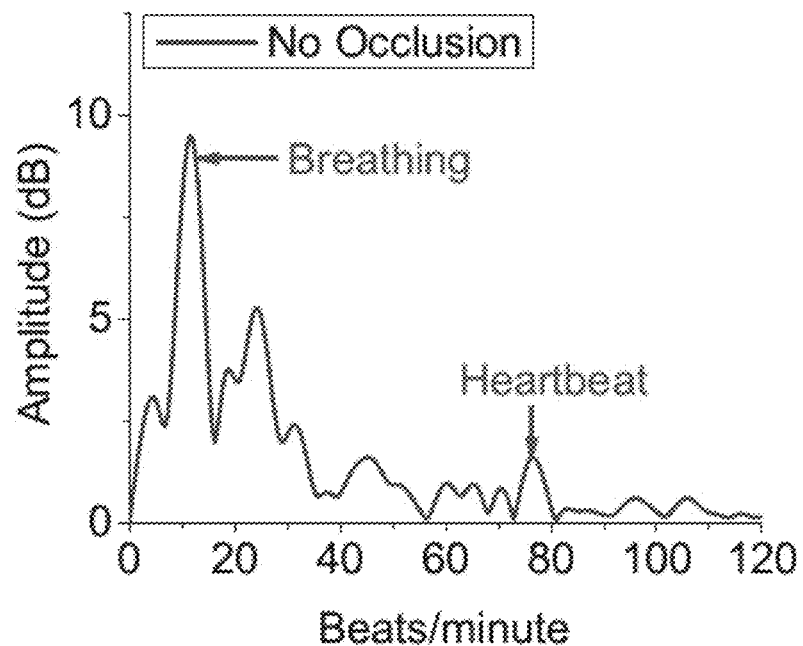
FIGS. 8A-8B are graphs illustrating an example of the received signal when the radar beams to the subject's heart area with and without occlusion created by human body components (such as arms).
Figure 8B:
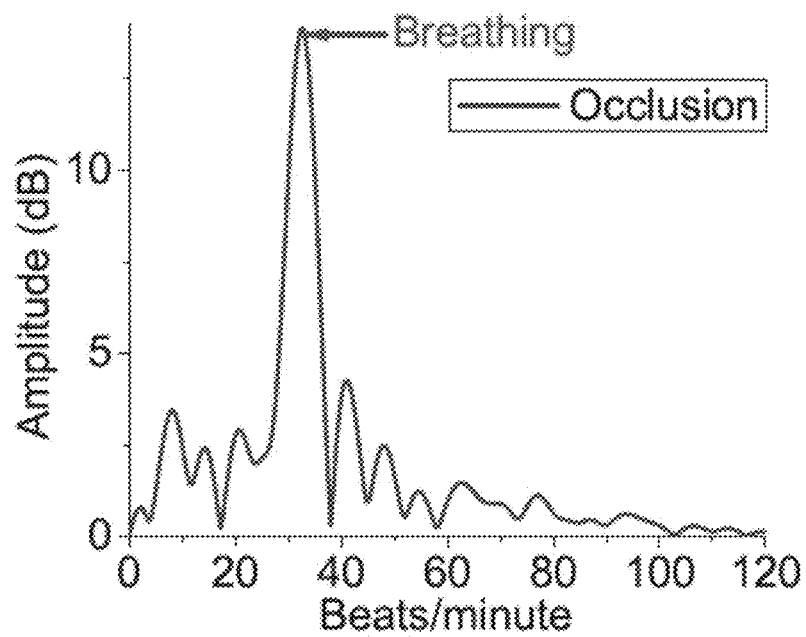

The respiration and heartbeat information are detectable when the radar beams to user's front chest. Meanwhile, those vital signs are difficult to capture when the radar beams to user's back. Exploiting those facts, a scanning algorithm was developed which mechanically brings the radar across the bed surface to scan and search for a position that senses vital signs. During the scanning, the radar transceivers are continuously running and pointing orthogonal to the bed. FIG. 8 shows the human posture, location of the radar and the corresponding power distribution of the measured vital signal. The posture detection algorithm relies on two main features: (1) the vital signal (heartbeat and respiration) reflected strongest when the radar is orthogonal to the human chest as (2) The reflected signal from human body at vital sign frequency band is caused from LOS position.

Understanding these fact, by applying Kadane's algorithm on the collected RSS, a subset of signal that content a maximum vital-sign reflected component was identified. This algorithm bring down the resolution of detecting the angle between human back and the bed surface down to 5°. Details implementation is shown in Algorithm 3. This step allows for the radar to point to the frontal chest of the patient.

Next, the radar is made to search for and beam to the heart location. Heart location is selected because the corresponding signal fluctuation contains both respiration and heartbeat information. However, it is nontrivial to automatically direct the radar from current location to the heart location. The required moving distance differs for different postures. For example, moving the radar from location 5 to 3 (FIG. 6B) requires the radar to move its beam by 5 cm when the user is lying flat on bed (orthogonal to radar beam), but it requires only 4 cm when user body forms a 40 degree angle with the bed. In response, a device of the invention estimates the angle between the user's back and the surface to calculate the effective movement its beam would make on the chest surface given a fixed amount of movement on the radar. The radar is then directed to different areas while capturing the signal at each moving step and stops at the location. Further, it identifies the heard area by finding the location that has the received signal that best matched with that of the heart location.

Using an algorithm, the navigator can determine the angle of the subject's body and instruct the volume estimator to move to point B in order to regain an optimal angle for measuring the subject's chest.

Example 7: Point Localization

Figure 6A:
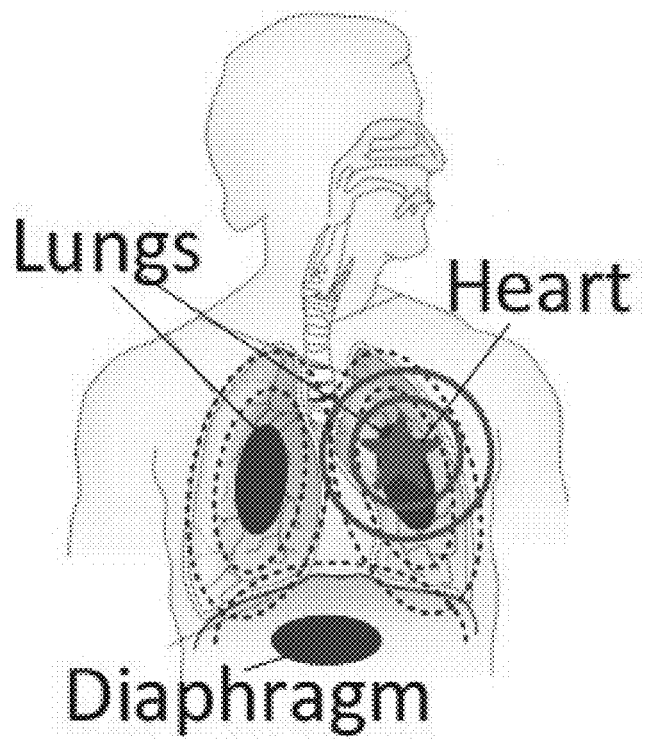
FIGS. 6A-6B depict the chest area of a subject.

The apparatus of the invention is capable of recognizing the exact chest location that the radar is beaming at. As seen in FIG. 6A, human chest movement comprises 3 main sources: lungs, diaphragm and heartbeat. Different areas move differently according to the distance to vibration sources, and the structure of muscles. The chest is divided into nine areas as in FIG. 6B, named as P1, P2, ..., P9, respectively. This division depends on the radar beamwidth, its distance to chest, and the chest size. With a narrower beamwidth, the number of areas can be increased. On the other hand, the number of areas are decreased if the system monitors young subjects with small chest (e.g. a baby). The key idea is to make sure the beam width is small enough to isolate the signal reflected from different areas. Moreover, as only a discrete set of areas have been trained, an interpolation technique is designed to fill up the data for untrained areas.

A machine learning technique was used to realize area recognition. Specifically, the radar beams a signal continuously, observes the signal features, and then match with those trained offline to identify the current area.

Example 8: Testbed, Apparatus Set Up, Software and Implementation

Figure 9A:
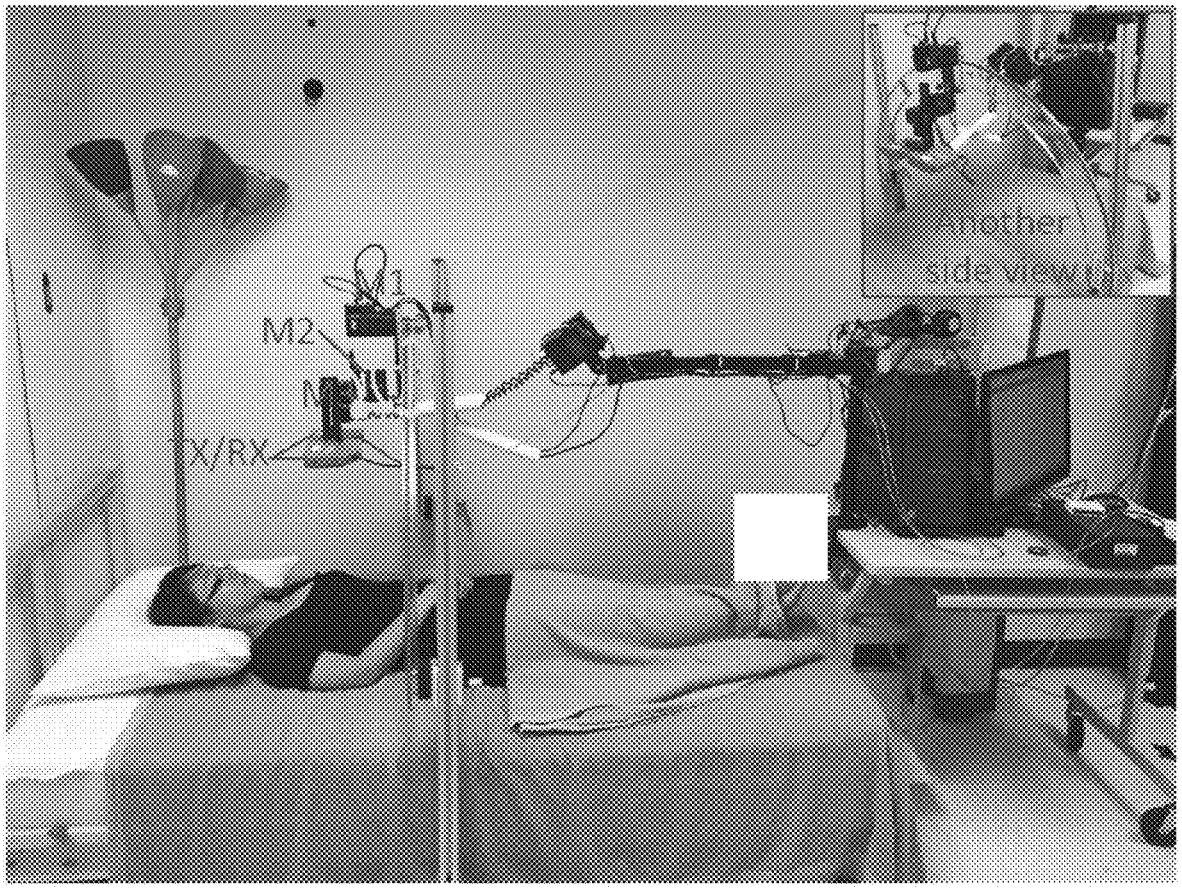
FIGS. 9A-9C are photographs of the invention apparatus set up. A radar beams to human's heart area to observe the respiratory and heart beat activities. If a body movement or posture change is detected during sleep, the radar is then moved to a new location and redirects its radio beam to maintain its orientation pointing to the heart area. The radar navigator could roll, pitch, and yaw with 360 degree of freedom using three motors M1, M2, and M3 to control antennas' position and their beaming directions.
Figure 9B:
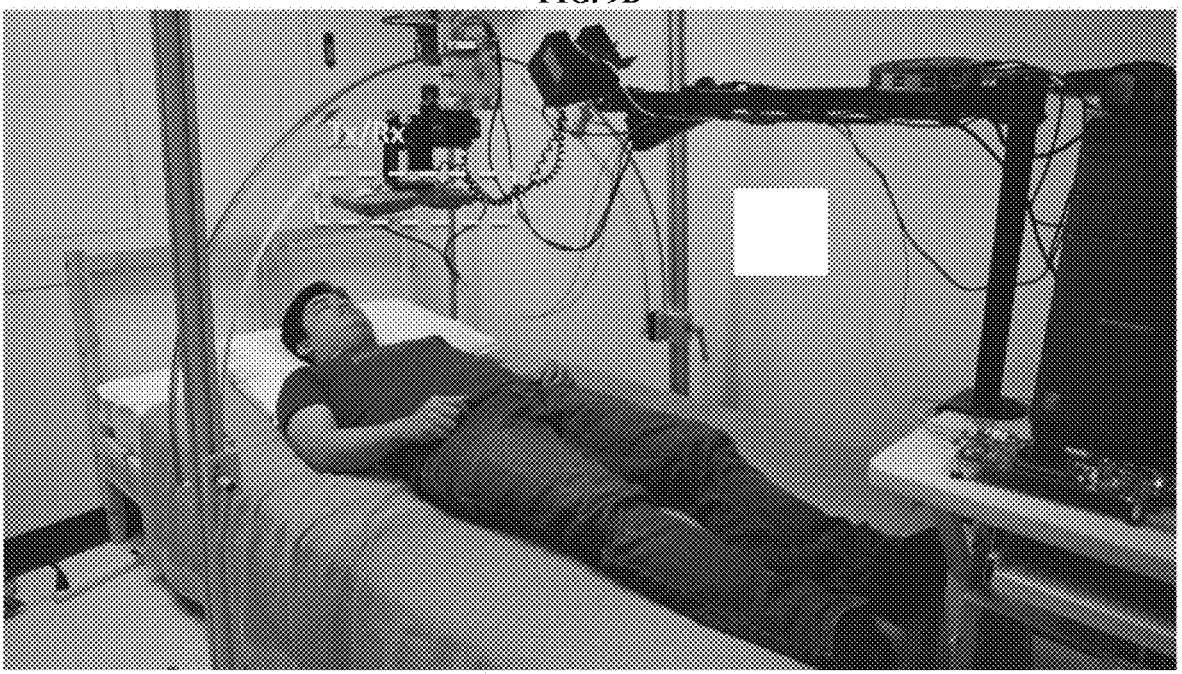
Figure 9C:
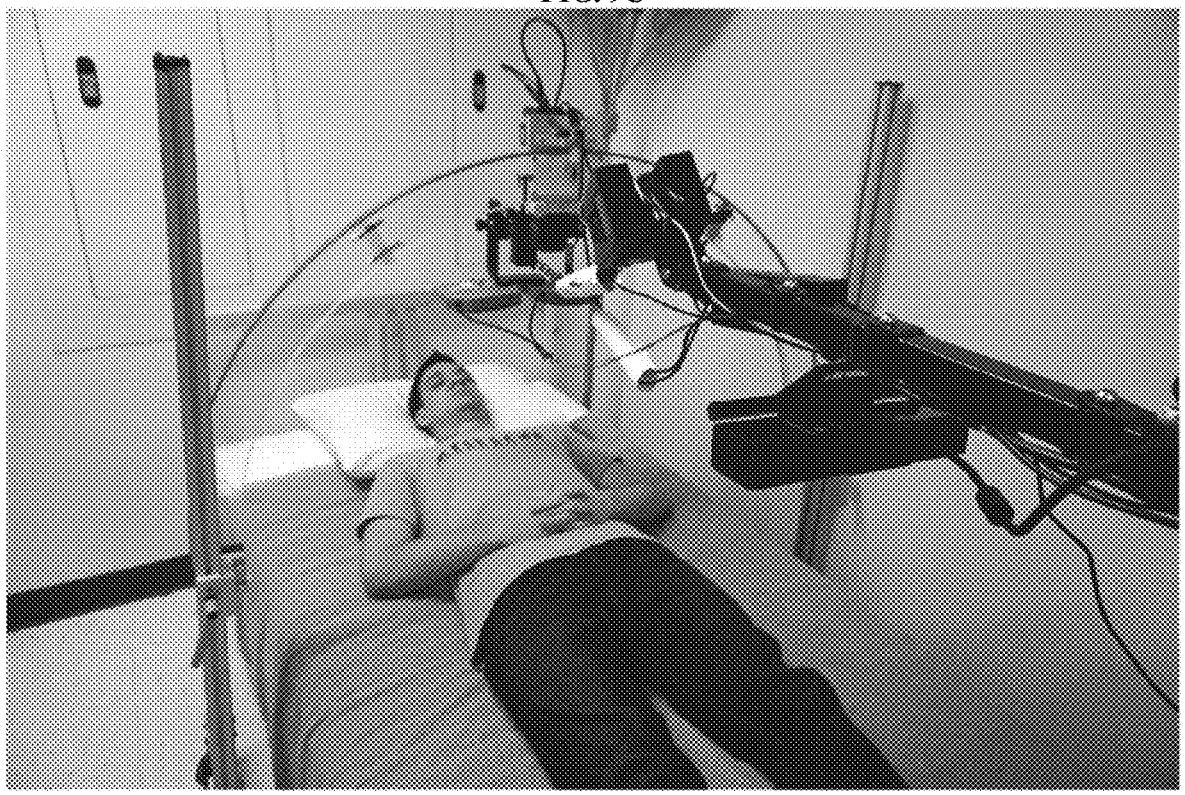

As depicted in FIGS. 9A-9C, the hardware setup is composed of two main components: a radio transceiver and a radar navigator. The radio transceiver hardware is developed from a Software Defined Radio board (WARP kit v3). A transmitter sends single tone continuous wave at 2.4 GHz by the script written in Matlab software. A receiver captures reflected AC-coupled signals, convert to base band, and output discrete I/Q samples with 100 kHz baseband sampling rate. The received I/Q signals are transferred to a PC through Ethernet cable, to which the present algorithms in Sec. 4 and 6 are applied. The radio antennas are mounted on a mechanical motion control system from Applied Motion sliding and rotating which are steered by a PC host in real-time. The antennas are connected to WARP kit v3 board through SMA connection. The control system supports 360 pan, tilt, and the slide movement is controlled by an automated script. To navigate the radar to proper location and orientation, the motion control system is driven by the present radar navigator algorithms (Sec. 6) which are implemented on the PC host. The whole system is mounted across and on top of a twin-size bed on which all experiments are conducted.

A program was implemented in Matlab to perform the training algorithms and volume estimation algorithm described in Examples 6 and 7. The radar controller software was developed and run in Matlab to realize posture estimation, point localization and associated training algorithms, and also make decisions on moving and steering antennas to proper location. A software was developed using C++ to simultaneously trigger multiple hardware pieces at once to minimize the execution effort of the system and minimize the starting time discrepancy across the devices.

Example 9: Live Subject Experiments

Participants:
To evaluate the performance of the apparatus, the breathing volume of 6 subjects was measured using the apparatus and methods of the invention. During the experiments, a subject slept on the apparatus testbed wearing their normal clothes, sometimes covered by a thin blanket.

Control Measurements:
A spirometer was used to evaluate the apparatus's volume estimation accuracy. A camera was also used to record the participants' sleep behaviors and noises, in conjunction with a laser pointer to track the volume estimator's antenna direction.

Training:
The training process was carried out for 9 minutes for each subject. The subject was instructed to breath normally to a spirometer while the volume estimator radar navigated and collected data at the desired points across the subject's chest.

Testing:
After the training process was completed, each subject was instructed to sleep normally for about 60 minutes while apparatus operated. The control spirometer was left attached to the subject's mouth to collect control measurements for the duration of the experiment.

Figure 10:
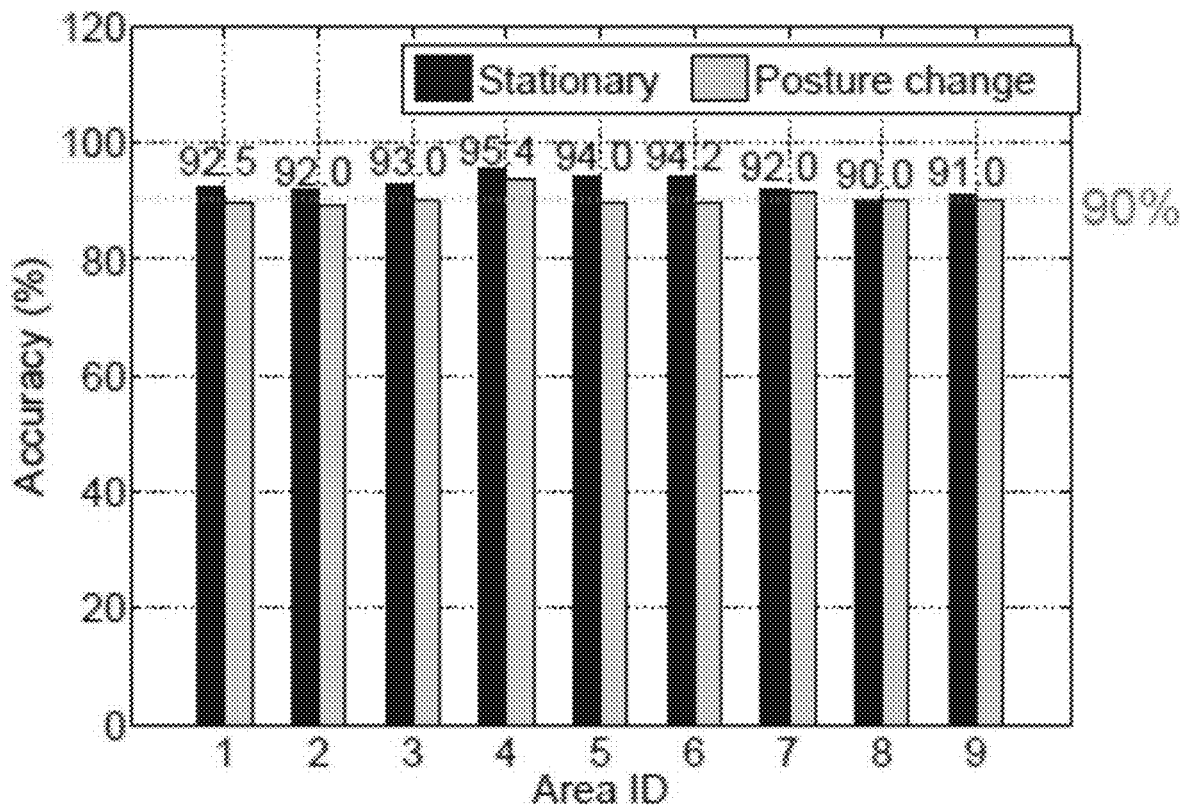
FIG. 10 is a graph reporting the mean accuracy of volume estimation by an illustrative apparatus of the invention while the subject is stationary and while the patient is changing postures during the test. The mean accuracy is reported for each of the nine areas outlined in FIG. 6B.

Results:
As reported in FIG. 10, the apparatus was found to estimate breathing volume with 90% to 95.4% accuracy within an average window of 10 ms. As reported in FIG. 11, it was found that accuracy was highest when the volume estimator was aimed at areas of the chest (numerically labeled in FIG. 6B) on the upper part of the chest and around the heart area (areas 3-6). The impact of body and limb motion was found to be small due to the automatic repositioning directed by the navigator device.

Medical Diagnosis Potential:
The breathing volume measurement data from three subjects, (one male juvenile with minor hypopnea, one adult male with no known breathing disorder and one female adult with a mild snoring pattern) was collected. The breathing volume data, reported in FIGS. 12A-12C, was assessed by a sleep expert clinical doctor who directs and operates a clinical sleep analysis lab in a state hospital.

From the fine-grained breathing information, the doctor was able to map the breathing volume pattern to each person without prior knowledge about the mapping. Once the symptom is confirmed, the doctor was able to provide further analysis of breathing and sleeping issues from the volume information, part of which is presented in FIG. 12. The doctor commented in regards to the data in FIG. 12B, "with a known snoring female, the signal shows a small inspiratory flow limitation but very little effect on her tidal volume. This is a marker of mild flow limitation that is commonly seen in premenopausal woman. It is likely a non-REM sleep because of the regular rate. The normal volume variability which can normally be seen through $CO_2$ and $O_2$."

Figure 12C:
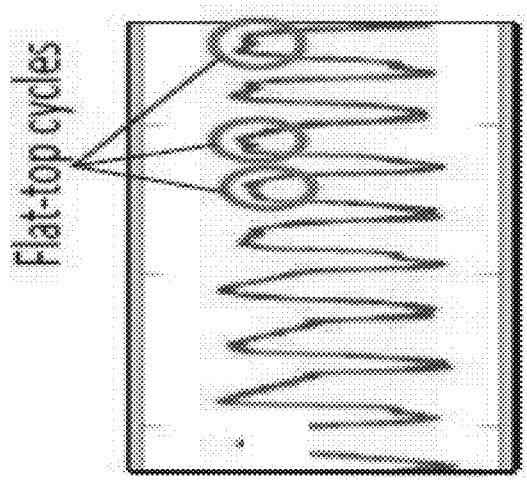
FIGS. 12A-12C depict graphs comparing the estimated and true breathing volume measurements for three participants with and without breathing and sleep disorders.

In regards to the data in FIG. 12C, "these three breathing cycles (marked in FIG. 12C) show a moderate inspiratory flow limitation that decreases the tidal volume of the breath. This could be clinically important because the child might not get enough $O_2$ due to the air flow limitation and decreased volume. This could lead to alteration of blood gas such as $CO_2$ and $O_2$. The moderate flow limitation during sleep is one form of hypopnea."

Figure 12B:
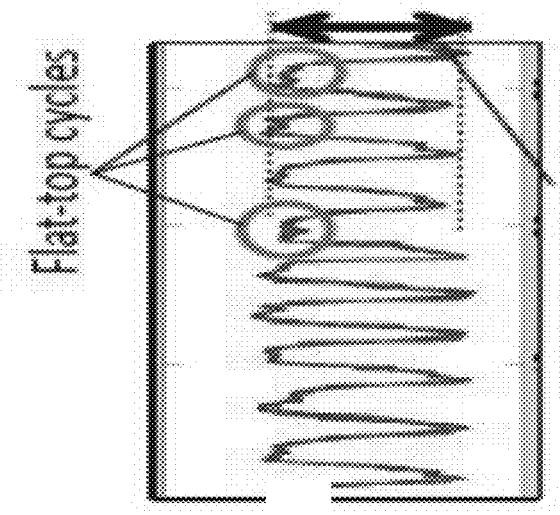
Figure 12A:
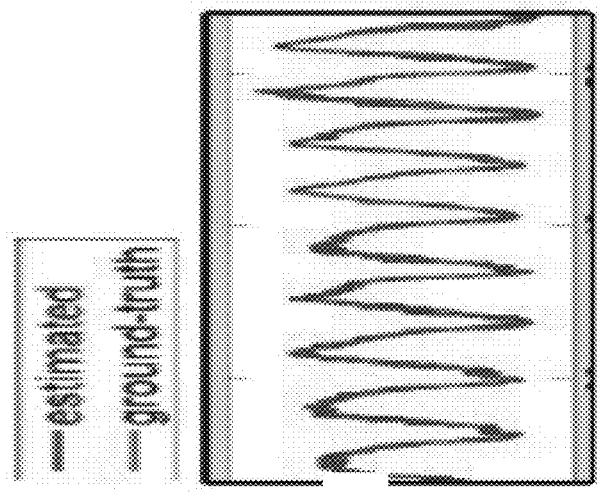

As stated by the clinical doctor, the flat top portions depicted in FIGS. 12B-12C are an indication of flow limitation and can be useful in making a clinical diagnosis. These data features cannot be captured with previously available radar based breathing rate methods.

Example 10: Point Localization Technique Accuracy

Figure 6B:
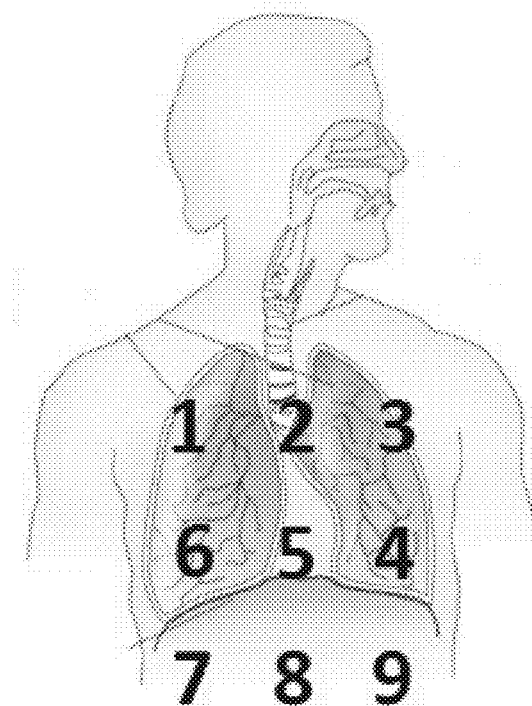
Figure 11:
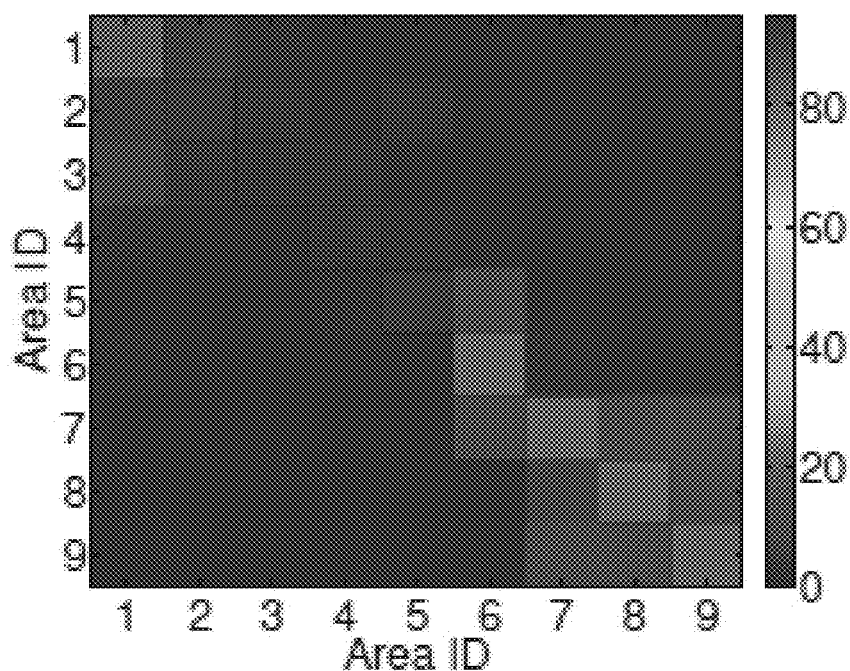
FIG. 11 is a heat map showing the accuracy distribution of the point localization technique.

After training the apparatus using the spirometer setup, the volume estimator antennas were aimed at different areas of the chest, as the areas are outlined in FIG. 6B. The antenna was aimed at each of the nine (9) areas fifteen (15) times each for all of the live subjects tested. The accuracy was then averaged across participants. The system then attempted to correctly identify which of the nine areas of the chest the antenna was pointed at. The accuracy of all of the tests was averaged and the results are reported in FIG. 14. The algorithm was able to determine the correct area of the chest with high accuracy, especially when pointed at the upper chest and heart area (areas 2-6) while accuracy drops near the abdominal area; there are more vital signal effects on the former set of areas. FIG. 11 shows the error distribution of the localization. When an error happens, it tends to be confused with an area with its neighborhood.

Example 11: Posture Detection Accuracy

Figure 13:
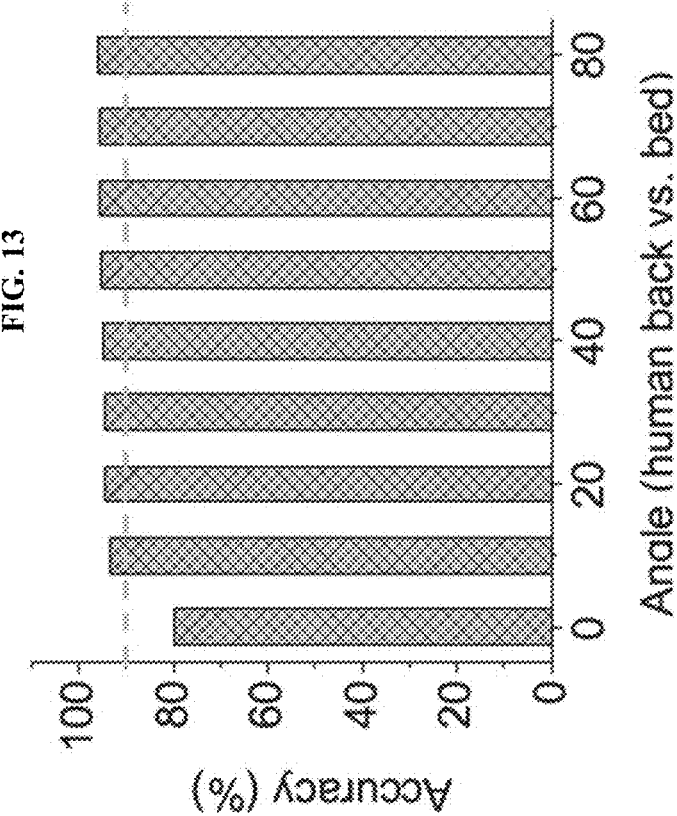
FIG. 13 is a graph of the estimation accuracy of the angle between the subject's back and the bed surface.
Figure 15A:
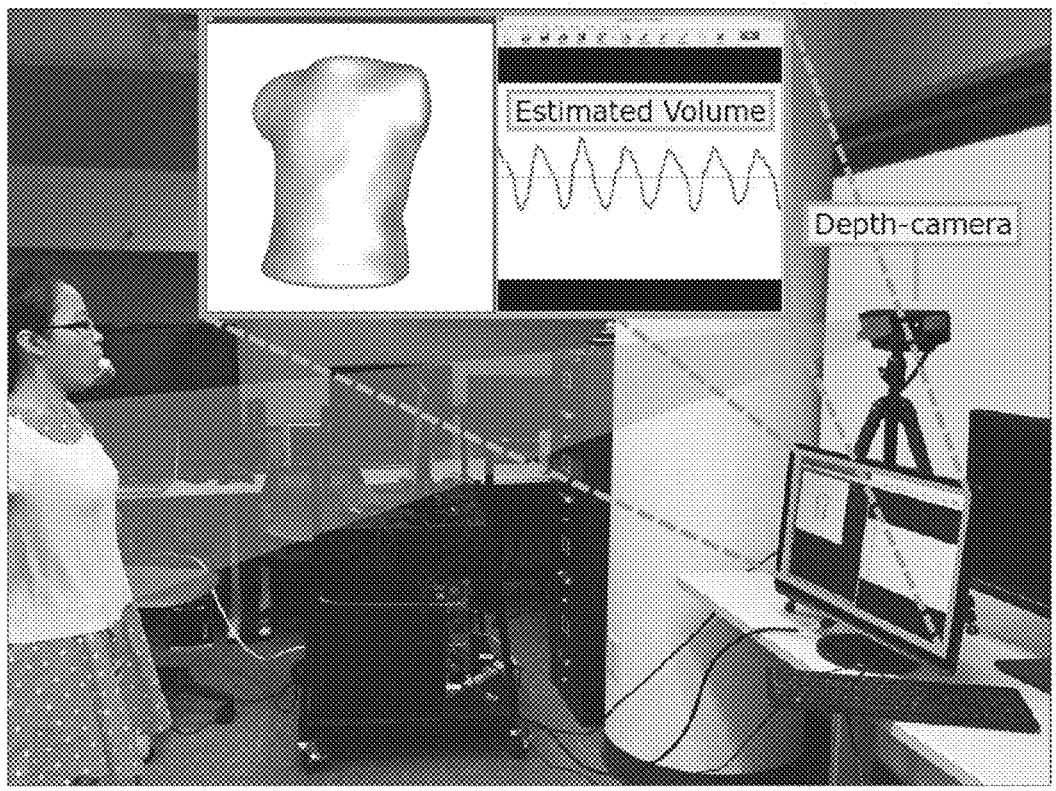
FIG. 15A is a picture of the proposed system environment for real-time surface-based tidal volume monitoring. A screen illustrating the real-time surface reconstruction and estimated tidal volume during the patient monitor training process is shown. This setup illustrates the non-invasive methodology proposed by the present vision-based tidal volume estimation technique.
Figure 15B:
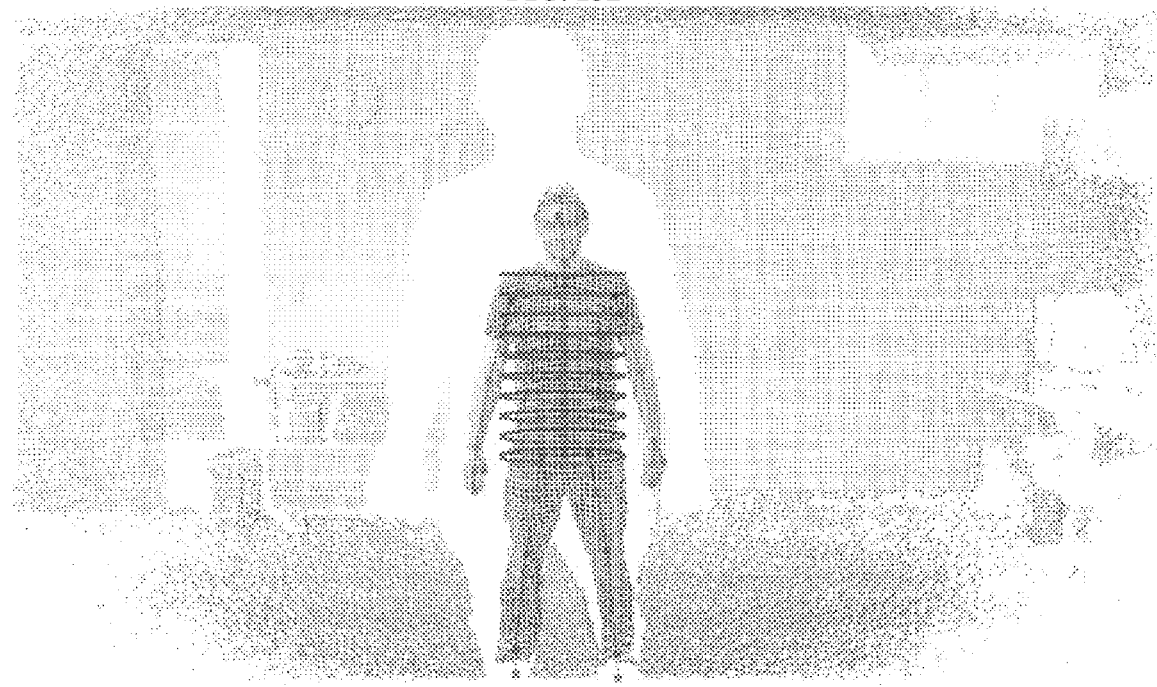
FIG. 15B is a color point-cloud acquired from the device with the both the skeletal and clipping cylinder super-imposed. Any vertical posture within the devices field-of-view (FOV) is valid with the system of the invention.

A subject was asked to lie on a bed with his/her body at an angle ranging from 10°-90° with respect to the bed. The performance of the posture detection algorithm is presented in FIG. 13. A participant is asked to lie his/her body w.r.t. the bed with an angle ranging from 0° to 90° with step of 5°. The estimation is repeated 20 times at each angle. The angle is considered to be correctly estimated if the result is within 5% from the ground truth. With the new technique of posture detection, the performance of the system is significantly improved.

Example 12: Real-Time Tidal Volume Estimation Using Iso-Surface Reconstruction

The accurate estimation of a patient's tidal volume using a vision-based technique is dependent upon both the model of respiratory deformation patterns and the correspondence relation used to provide a correlative link between this behavior and the actual tidal volume. The challenges presented in obtaining an accurate estimation result are derived from the correlation of the models from the true deformation behavior and the means of accurately obtaining the prerequisite correspondence for populating the models estimation basis. In the respiratory monitoring framework proposed, these challenges were addressed by introducing a two phase correspondence model from which the chest surface deformations, respiration rate, and tidal volume can be effectively extracted and estimated on a per individual basis. This estimation is initially obtained using direct 3D volume measurement and then improved using a per-patient trained correlation function.

To obtain these individualized respiratory characteristics, a methodology was developed for extracting a complete volumetric iso-surface that includes the deformation behavior of the patient's left thorax, right thorax, and abdominal region. A new deformation model was also introduced that provides a closer representation of a naturally expanding chest cavity to increase the accuracy of a patient's estimated tidal volume. This respiration model is then combined with a adaptive correspondence model that utilizes a Bayesian-based neural network to populate a regenerative tidal volume estimation.

A. Omni-Directional Deformation Model

The proposed respiratory model is fundamentally composed of the accurate reconstruction of a volumetric region enclosed by an iso-surface that describes both the deformation characteristics of a patient's chest and the change in volume of the patient's chest. The premise of the present omni-directional model is based on the accurate approximation of a solid volume by its characteristic function formed from a set of unordered, oriented points that allows to extract the iso-surface that describes these characteristics.

In this approach, the mobility of the patient was minimized during the monitoring process to employ this omni-directional chest deformation model to form a more accurate basis for the correlation between a patient's chest deformations and the corresponding tidal volume. This also allows to consider the chest deformations specific to the monitored patient within the present estimations providing a better model to infer the associated tidal volume. In this Example, the basis of the present model was described as compared with prior techniques and provide an derivation of how this model is applied to form a more accurate representation of the chest deformations observed during a patient's breathing cycle.

Prior techniques for modeling chest movement utilize orthogonal deformation models of a patient's chest surface to infer the correlation between the monitored chest movements and the corresponding tidal volume. These models are based on the orthogonal movement of the chest within a depth image as displacements. The change in these displacements is then utilized to form a correlative relation between the chest displacement and the estimation of the patient's tidal volume. The present method is motivated by the observation that this deformation model does not accurately represent the known physiological displacements of a human lung during the respiration process. The images in FIG. 16A 3 illustrate the difference between an orthogonal displacement model and the proposed omni-directional model.

An omni-directional deformation pattern provides a closer approximation of the true displacements imposed on a patient's chest surface as they breathe. This is formulated based on the observation that the displacement incurred while breathing effects the estimated tidal volume which is a function of the expansion of the left and right thorax (e.g. the chest is modeled as balloons rather than a set of uniform displacements). Using this observation, the aim is to increase the accuracy of the deformation model that is used to derive the correspondence between chest deformations and the estimated tidal volume.

The derivation of the present model is based on the established methodology of reconstructing solid model surfaces from unordered, orientated, point sets. The application of this method was then illustrated as a means to accurately estimating a patient's tidal volume based on the volumetric changes in the patient's chest model. In this formulation the patient's chest C(t) was denoted as a three-dimensional solid with volume V(t) contained within the closed boundary surface $S(t) \subset \mathbb{R}^3$. This is derived from the fact that the Divergence Theorem:

$$\iiint_{V(t)} \nabla \cdot \vec{F} \, dV = \oiint_{S(t)} \langle \vec{F}, \vec{n} \rangle dS$$

allows the volume integral of the solid chest region to be expressed as the surface integral which can be approximated using Monte-Carlo integration assuming discrete uniform surface sampling where $\vec{F}=(F_x; F_y; F_z): \mathbb{R}^3 \mathbb{R}^3$ and $\vec{n}_i$ is the estimated surface normal at point $\vec{p}_i$:

$$\iiint_{V(t)} \nabla \cdot \vec{F} \, dV \approx \frac{|C|}{N} \sum_{i=1}^{N} \langle \vec{F}(\vec{p}_i), \vec{n}_i \rangle$$

The aim of this technique is to reinterpret the characteristic function of this solid region as a set of volumetric integrals that can be computed as a summation over a set of surface samples. The characteristic function of the patient's chest region, denoted as $x_c(t)$ is a function that defines the solid volume $C(t) \subset \mathbb{R}$ by providing a function that evaluates to one within the boundary S(t) and zero otherwise. The discrete form of the characteristic equation expressed in terms of Fourier coefficients can be defined as:

$$\hat{x}_c(l, m, n) = \int_{p \in S(t)} e^{-i(lp_x + mp_y + np_z)} dp$$

Using the proposed application of the Divergence Theorem, it can be shown that due to expressing the Fourier coefficients as volume integrals, the evaluation of the Fourier coefficients of the characteristic function can be computed using the Monte-Carlo approximation:

$$\hat{x}_c(l, m, n) = \frac{1}{N} \sum_{i=1}^{N} \langle \vec{F}_{l,m,n}(\vec{p}_i), \vec{n}_j \rangle$$

such that the vector valued function: $\vec{F}_{l, m, n}: \mathbb{R}^3 \mathbb{R}^3$ adheres to the condition: $(\nabla \cdot \vec{F}_{l,m,n})(x, y, z) = e^{-i(lx+my-nz)}$ and the functions $\vec{F}_{l, m, n}$ whose divergences are equal to the complex exponentials. The inverse Fourier Transform of these coefficients is then computed through a convolution of the oriented samples through a voxel grid to extract the solids characteristic function.

From the accurate reconstruction of the surface S(t) that bounds this solid region through the Monte-Carlo approximation, the basis of the present omni-directional model provides a high resolution approximation of the deformations observed during the respiration process. Based on this approach, the aim is to provide a more accurate estimation of the patient's tidal volume due to the more accurate representation of the patient's chest deformations.

B. Chest Volume Extraction

Non-contact based methodologies inherently require a means of identifying the patient's position and orientation in space as a prerequisite to estimating the tidal volume that corresponds to the observed chest movements. Automating this process provides consistency in the region of interest monitored for surface changes and limits additional requirements imposed on the patient during the monitoring process. The automation of this process also eliminates the requirement of strictly limiting the patient's position to a pre-configured region of interest. Rather it was built on the premise that the skeletal data can be utilized for automating the process of identifying the patient's chest region and exploit this information to simplify the monitoring process.

Figure 14:
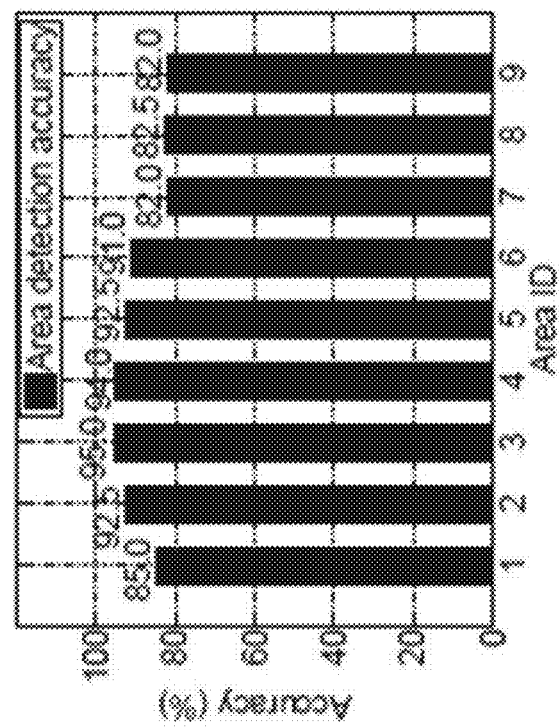
FIG. 14 is a graph reporting the chest area ID detection accuracy of the apparatus.

The process of identifying and extracting the patient's chest region to calculate the volume of the deformable surface that describes the respiration patterns of the patient is illustrated in FIG. 14.

The basic premise for reliably detecting the chest surface of the patient is derived from the acquisition of the sampled depth-image $D_s(t)$ (depth samples per-timestep) containing the patient and the raw skeletal data. Based on the forward orientation of the patient, assuming no occlusions, the skeletal information was considered as a basis for interpreting a chest subset c, denoted as $D_c(t)$, of the n-sampled depth image $D_s(t)$ as the chest region c of the patient at time t. The subset of pixels $p_{ij} \in D_c(t)$ that reside within the cylindrically clipping region c, defined by the patient's skeletal structure and position, contribute to the definition of the patient's chest region. From this point, the objective is to form a representation of the patient's entire chest region as an enclosed volume defined through a point-cloud containing oriented points that approximate the patient's chest deformation states as a function of time, referring to this surface approximation as the volumetric deformation-cloud P(t). The samples collected from the depth-image, converted into three dimensional coordinates, lack orientation vectors that approximate the curvature of the patient's chest. Therefore, in the present reconstruction process accurate estimates of these normal vectors must be generated.

Since timing is critical to the viability of this technique, a reliable algorithm based on standard stencil techniques to approximate the surface normals within an organized point-cloud was proposed. Since the depth-image chest region subset contains a significant portion of occluded surfaces, including clipped regions and the patient's back, a simple methodology for filling these occluded regions was proposed. This process is required to generate an enclosed volume to reconstruct a volumetric mesh of the patient's chest. In the process of approximating the surface of the occluded regions within the volumetric deformation-cloud, a planar projection technique was employed for mapping a patient's chest points as a fixed back surface and introduce a convex-hull based projection algorithm for filling the remaining clip holes (e.g. neck, waist, etc.). The aggregation of the chest, back, and generated clip-region points form the state of the volumetric deformation-cloud that is then used as the input to the iso-surface extraction algorithm. The overview of the proposed method is presented in Algorithm 6, where B(t), N(t), W(t) represent the set of back, neck, and waist points respectively, P(t) is the volumetric point cloud, and S(t) is the reconstructed chest surface mesh.

The generation of this deformation model over time describes the deformation characteristics of the patient's chest that provides a correlation to the associated tidal volume. From the voxel-based surface reconstruction process, the generated triangulated mesh that represents the patient's chest volume $V_m(t)$, is directly calculated using the signed tetrahedral volume algorithm.

Since the resulting surface reconstruction contains a significant volume (including tissue and bone), the volume initially recorded during the monitoring process was denoted as the base volume $V_0$. This value will then be subtracted off of all subsequent volume calculations to provide the discrete value dV for each time-step. Since this represents the form of the present deformation correlation to tidal volume, dV is equivalent to the patient's tidal volume. This method was extended through training to achieve a more accurate estimation.

Example 13: Chest Surface Acquisition

The acquisition of a depth-image from any infrared monitoring device incurs a natural variance in the depth measurements that are obtained within a single frame. In the instance of depth-imaging devices, the depth error associated with each pixel $p_{ij}$, is a function of the distance to the reflective surface being monitored as well as the surfaces material properties. Additionally, each pixel must be classified as part of the patient or as part of the background. The natural fluctuations within this process and depth measurement errors can degrade the accuracy of the present tidal estimation. Therefore, in this section the implementation of the cylindrical clipping region (FIG. 17A) and the associated pixel history tracking algorithm provided to minimize high-frequency pixel fluctuations were covered.

The clipping cylinder that identifies the patient's chest region is defined through an automated process based on the subsection of a conventional skeletal frame illustrated in FIG. 17A. Specifically, the base of the cylinder is positioned at the hip joint h, and extends to the neck joint n. The radius of this cylinder is defined by the average distance of both the left l and right r shoulder joints. The generalized construction of this cylindrical clipping volume provides a viable heuristic for identifying the patient's chest volume bound by the accuracy of the skeletal joint estimations.

To alleviate the natural fluctuation of the depth-image pixels that are determined to be part of the patient's body, but reside within the edges of the clipping region, a simple stability scheme based on pixel tracking history is provided. A visualization of this pixel-history is provided in FIG. 17B. If the tracking history of the pixel $p_{ij}$ is saturated (continuously tracked) for the entire bit history length (bh), then it will contribute to the definition of the generated deformation-cloud. This reduces the impact of fluctuating pixels as they are automatically culled from the background samples.

Example 14: Stencil-Based Normal Estimation

The process of reconstructing the surface of the scanned chest region requires every sample collected within the depth cloud to have an estimated orientation that approximates the curvature of the surface. Normal estimation for surface reconstruction is a well-studied research topic and several normal estimation techniques have been developed and successfully employed within the Point Cloud Library (PCL) with widespread use. These techniques include k-neighbor or radial search for estimating normals for unordered point clouds and integral image normal estimation based on ordered depth-images. However, in the process of clipping the patient's chest region from the acquired depth-cloud, these techniques are ill suited for two reasons: (1) the additional computational cost associated with an unordered point set occupies unnecessary frame-time when adjacency information is known and (2) integral image techniques provides highly consistent estimated normals for ordered point-sets, but is not applicable in the instance of calculating reliable normals for the points that compose the edge of the clipped chest region due to the border of its rectangular region. Due to the limiting factors of these recently developed normal estimation techniques in their application to the depth cloud within the patient's clipped chest region, an iterative stencil-based technique was employed to accurately estimate all surface normals, including edge points and corners with missing adjacent neighbors. This is accomplished using the standard technique of sampling neighbor points to obtain an averaged cross-product that estimates $\hat{n}_{ij}$ at point $p_{ij}$.

The implemented technique relies on a stencil-based neighbourhood selection algorithm that calculates the cross-product of the current point $p_{ij}$ with its surrounding neighbors. Based on size of the stencil, c concentric squares are formed around the point where: c≥3 and c % 2=1.

$$\hat{n}_{ij} = \sum_{i=1}^{c} \frac{\vec{p_i} \times \vec{p_j}}{|\vec{p_i} \times \vec{p_j}|}$$

Figure 18A:
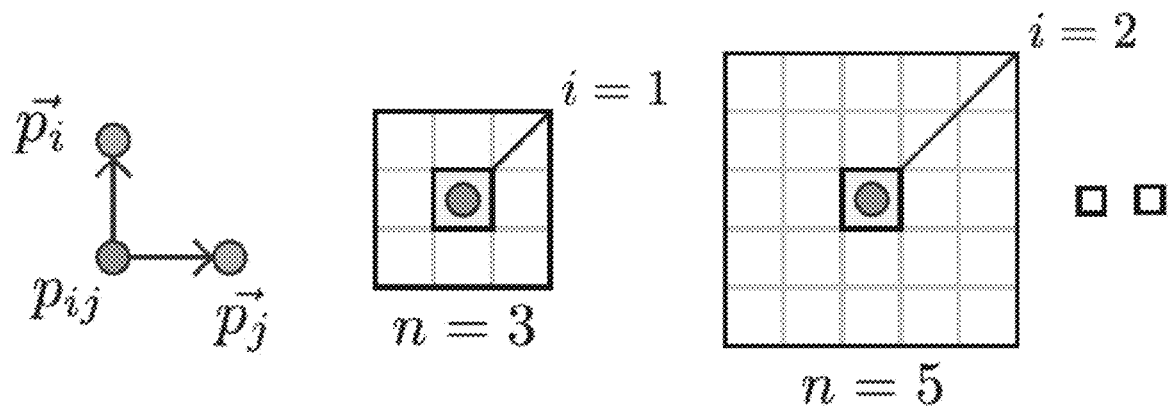
FIG. 18A is a stencil-based normal estimation for different stencil sizes n=3, 5, . . . to estimate the normal $\hat{n}_{ij}$ at point $p_{ij}$. As the stencil size is increased, the number of samples per point $p_{ij}$ increases to contribute the surrounding area to the normals orientation.
Figure 18B:
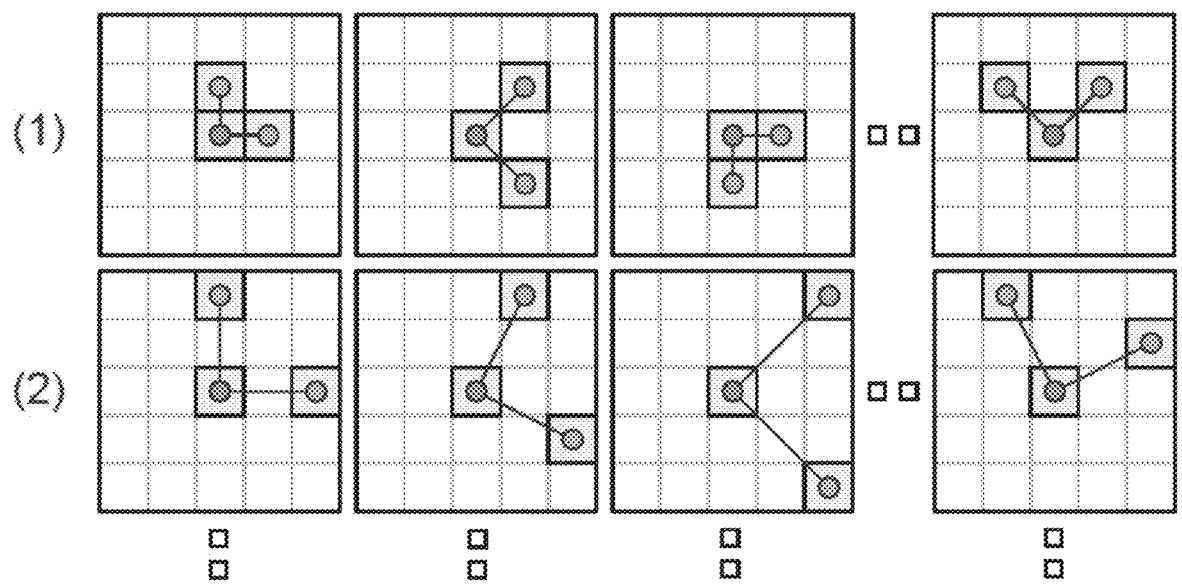
FIG. 18B is a stencil-based normal estimation with a stencil size: n=5 and the corresponding clock-wise crossproduct sampling indices for the central point at $p_{ij}$. Each row (i) illustrates iteration i of the algorithm for evaluating the cross-products at level i. All sampled cross-products from all levels are summed and then normalized to derive the estimated surface normal $\hat{n}_{ij}$.

This calculation is then repeated through iterative clockwise rotations to provide an averaged normal estimation. For each concentric square at level i, each of the possible cross-products are calculated. Edge cases are handled by the 2D generation of valid point indices within the depth-image. After i iterations, the current sum is normalized to obtain the estimated normal of the surface at (i; j). The total number of cross products performed for the given stencil size n is provided by: $\Sigma_{i=3}^{n} 2^i$ with a normalization. An illustration of this algorithm for n=5 is illustrated in FIG. 18B.

A consideration for this normal estimation technique is addressed by the use of the integral image technique for calculating smoothed normals without relying on large stencil sizes. Naturally, larger stencil sizes require a higher number of samples, thus degrading the execution time of this technique. However, when using small stencil sizes (e.g. 3, 5), the algorithm provides normals that approximate the results provided by the PCL unorganized point set algorithm while generating accurate edge normals. An illustration of the normals estimated using the stencil-based technique is shown in FIG. 19A.

Example 15: Hole Filling

To construct the surface of the patient's chest for calculating the corresponding tidal volume, the resulting surface mesh must form a water-tight model. To obtain this model, all occluded and clipped cross-sections must be filled with valid estimates of the surface curvature to form an enclosed volume. These regions are formed by the lack of any surface information about the patient's back and the clipped regions that are not visible to any depth scanning device (e.g. crosssections of the waist, neck, arms). This section describes the process of encapsulating the unbounded region defined by the clipped depth-cloud that defines the patient's chest surface.

A. Planar Hole Fill Algorithm

The clipped regions of the patient's chest provides four primary holes that must be properly filled to enclose the monitored chest volume. Based on the premise of planar grid projection a planar region can be easily filled within an n-sided polygon with a uniform grid of oriented points. This process is used once the edge points of the chest region have been identified and specific joints from the skeleton are used to identify the closest points to the clipped regions from the edge point sets. This is accomplished using the following algorithm: (1) Planar projection of chest edge points $C_p(t)$, (2) 2D Convex Hull on $C_p(t)$, (3) Grid Generation based on AABB of Convex Hull, (4) Point-in-polygon test for included grid points, (5) Generate uniform surface normals.

B. Clip-Region Surface Filling

During the process of identifying the chest region of the depth image using the skeletal information, the clipping region of the cylinder introduces newly opened regions that must be filled to construct the chest iso-surface. These regions include the neck, waist, and arms. For the larger clipped neck and waist regions, the characteristic function of the generated surface will be unbounded in these regions and for consistency one cannot allow an arbitrary interpolation scheme to dictate the surface closure in these regions.

Due to this, the planar hole filling algorithm is employed to populate these empty regions with uniformly spaced generated point samples. For each of the generated samples within these regions uniform normals that complement the surface direction required for constructing a iso-volume of the chest region were assumed. The image in FIG. 19B illustrates this process.

C. Back-Region Surface Filling

The remaining hole, caused by the occlusion of the patient, is the completely occluded back region. To ensure consistency of the unknown back surface, a simple back-fill algorithm was introduced to ensure that the naturally occluded region of the back is populated with an estimate of an appropriate surface. This is obtained by utilizing the orientation of the skeletal data (illustrated in FIG. 17A as $\hat{b}$) and projecting all of the existing chest surface points to a backward facing plane with offset from the spine α. The offset value of α only has to provide a consistent distance to the back plane and is defined as α=5:0 cm to simply define an average patient back depth. This is an inherently fast approach and provides a closely matched region of points that complement the curvature of the chest points, which aides in the reconstruction of the chest surface.

Example 16: Surface Reconstruction

The premise of the present technique is based on the accurate calculation of a total patient's chest volume based on the surface describing the left thorax, right thorax, and abdominal region during the respiration process. To achieve this an iso-surface reconstruction technique was utilized that allows to efficiently generate a bounded region as volumetric mesh that corresponds to an estimation of the patients tidal volume as the reconstructed model deforms over time. Accurately estimating the tidal volume and respiratory rate using the proposed omnidirectional surface technique requires a robust methodology for surface reconstruction based on a set of unordered, oriented surface points. Additionally the reconstructed surface must maintain the following properties: (1) the generated surface forms a manifold mesh, (2) the triangulation is water-tight, and (3) the ordering of every triangle within the surface is consistent. From the premise of extracting a surface from a set of unordered, oriented points, provides an effective means of generating a surface conforming triangulation through the use a variation of the Marching Cubes algorithm. These techniques are consolidated within the present model presented in Example 12 to ensure the construction of a water-tight, manifold mesh with consistent ordering.

In each individual frame recorded from the monitoring device, the surface of the chest is clipped and the corresponding surface normals are estimated and the remaining holes within the surface are closed using the present uniform projection technique. Each of these independently acquired oriented point sets are then consolidated into an individual unordered, oriented point cloud. This cloud is then used as the input to the surface generation algorithm. Succinctly, the surface generation process is as follows: (1) the oriented point sets are splatted into a voxel grid, (2) the voxel grid is convolved with an integration filter, an estimation of the characteristic function using Fast Fourier coefficients extracted using FFTW and (3) the extraction of the surface is achieved using a variant of the marching cubes algorithm with cubic interpolation. The images in FIGS. 19C-19D illustrate the surface reconstruction process for three individual states during a patient's respiration process.

From the water-tight manifold mesh that is generated through this process, the volume of this volumetric mesh can be simply calculated using the signed tetrahedral volume algorithm. As the resolution of the mesh is decreased, the sample rate increases, however this reduces the accuracy of this technique due to the loss of deformation behavior over the surface of the chest. Similarly, increasing the resolution provides diminishing returns with respect to the accuracy of the estimated tidal volume. Therefore, a voxel grid size that provides an accurate chest surface representation was selected.

Example 17: Enhanced Tidal Volume Estimation

In this section, an algorithm was designed to robustly demodulate fine-grained tidal-volume estimated from volume estimated by the depth-imaging device. Since the present method is built on a physiological premise of the harmonic movement between the omni-directional chest expansion and the associated tidal volume, this phenomenon was utilized as the leading principle for the present training algorithm.

A. Training Algorithm

The proposed training process quantifies the relationship between chest movement (mesh volume) and breathing volume of the patient and is only needed once for each patient. During this process, the patient is asked to stand within the device FOV and breathes normally into a spirometer (FIG. 11). The ground-truth breathing volume of the patient is recorded by spirometer $V_s(t)$. The main objective is to find a non-linear correlation function $F_c$ of $V_m(t)$ and $V_s(t)$.

Several challenges need to be addressed to properly extract the correlation function $F_c$. First, the deformations imposed during the patient's breathing cycle are minimal. Second, it is difficult to detect minute volume changes given the noise inherently introducing by body movements and the variation of chest surface caused by the patient's clothing. Finally, the non-uniform movement of the chest during breathing cycle makes the correlation between mesh vs. breathing volume to be dependent on proper experimental setup and the distance of the patient to the monitoring device.

To overcome the these challenges, the regularity and quasi-periodic nature of a patient's chest movements were exploited. In particular, the change in the mesh surface is highly likely to expand and collapse along the same directions illustrated in the present omni-directional model. Moreover, the movement direction only changes when the subject changes from inhale to exhale states. Thus, chest mesh deformations within one half of a breathing cycle were identified and grouped for breathing volume estimation for which per-sample breathing volume is inferred. In the monitoring of this process, it was identified that the depth-image noise has a Gaussian distribution. Therefore, noise can be removed by standard filtering mechanisms. Based on the characteristics of the required signal-processing, one introduces a filtered half-cycle segmentation volume estimation technique based on the 3D measured volume and the groundtruth provided by a spirometer provided as inputs to the proposed training method.

To reduce the noise impact from the 3D measured volume a bandpass filter based on a frequency of 0.23 Hz was introduced based on adult respiration rates. Therefore, this define the parameters of this filter with fLow=0.1 Hz, fHigh=1.0 Hz. A low-pass filter with cutoff frequency of 1.0 Hz was used to removal non-breathing interference. Due to the effect from the noise especially the distance change between the patient and the monitoring device, the mesh volume changes detected by the device will incur a non-zero mean as the baseline fluctuates unpredictably. To solve this problem, the key idea is to find the noise frequency and remove that frequency component. In the present system, Savitzky-Golay filter with window size of 5 seconds and order 3 was used to obtain reliable results utilized within the present results and evaluation.

The filtered samples are then divided into segments. The segmentation is based on the fact that the breathing activity makes both mesh volume and actual volume data pass the observed baseline repeatedly. After mean removal, the base line is a zero-mean line and the number of inhale and exhale is equal to the number of cross zero line of the captured data. The zero-cross point is then considered as relative referenced points to align both the spirometer and measured volume data to establish the correspondence between the two signals. This provides the basis input for the present training procedure. This presented in Algorithm 2. In the present method a simple bMonitoring was used that is considered as the start signal when the patient's skeleton is recognized. Once this flag is set, a 5 s delay was imposed for the patient to prepare for the monitoring process.

B. Neural-Network Mesh-to-Volume Correspondence

The Bayesian back-propagation learning algorithm is employed to obtain the correlation of the mesh volume changes over time with the corresponding ground-truth volume. The mesh volume $V_m(t)$ is passed through the system in the first layer of the neural network. Hidden layers are expected to generate non-linear correlation function so that the breathing volume produced from the last layer is as close to the ground truth volume, Vs(t), as possible. To reduce the error between the output volume and the ground truth, the weight of each layer must be determined. The Mackay and Neal (D. MacKay, vol. 4, no. 3, pp. 448-472, 1992; R. M. Neal, "Bayesian learning for neural networks," 1996.) weight algorithm was applied for the correlation function. Sigmoid function, i.e., tanh $$S(t) = \frac{1}{1+e^{-t}},$$

was used as the activation function, progressing the number of learning iterations to 1000, or the threshold limit of 0.005 liters.

Example 18: Experimental Validation of Tidal-Volume Estimation

The results presented are categorized into two sections: (1) technique evaluation and (2) performance of the present real-time system. This is due to the implementation of this technique and the potential limitations of the hardware employed in the present solution to achieve a real-time estimation. Based on the objective of the present approach, the performance of the present proposed methodology was optimized with respect to computation time and tidal volume estimation based on the limitations imposed by the Kinect-2 depth-image acquisition rate with sampling. Furthermore, it was illustrated that through the reduction in computational costs within the present approach, one is able to extract a highly accurate estimation of the patient's tidal volume at distance range of 1.25 m to 1.5 m.

A. Tidal-Volume Estimation

1) Setup:

An experiment over 4 graduate students (1 female, 3 males) was conducted to evaluate the performance of the proposed volume estimation algorithm. The participants are required to stand in front of the camera while using their month to breathe into a spirometer. The participants are not allowed to breathe through their nose to ensure the amount of air of inhaled and exhaled are correctly captured by the spirometer. The distance from user is varies from 1.25 m to 1.75 m. The delay from the time that the skeleton is detected until the data is collected is controllable by the implementation and 5 seconds is a suitable time limit. The participant may become tired and breathe abnormally or uncomfortably after 20 s, hence, the data collection process is broken down into individual trials (20 s each). This process is repeated 20 times.

2) Basic Volume Estimation:

The correspondence between the deformations observed in the patient's chest and the estimated tidal volume has been established based on the relationship between the calculated mesh volume and the spirometer ground-truth volume. Inferring the tidal volume of the patient based on the present approach allows to accurately correlate chest deformations with the patient's actual tidal volume. Table 1 provides an overview of the present experimental participants contributing to the present evaluated results.

TABLE 1

Volume Estimation Results Across Participants

| User | sex | age | h [cm] | w [kg] | cs [cm] | error[l] |
|---|---|---|---|---|---|---|
| P1 | female | 28 | 156 | 47 | 35 | 0.079 |
| P2 | male | 27 | 168 | 70 | 42 | 0.075 |
| P3 | male | 26 | 170 | 65 | 40 | 0.067 |
| P4 | male | 24 | 169 | 67 | 41 | 0.055 |

Figure 21:
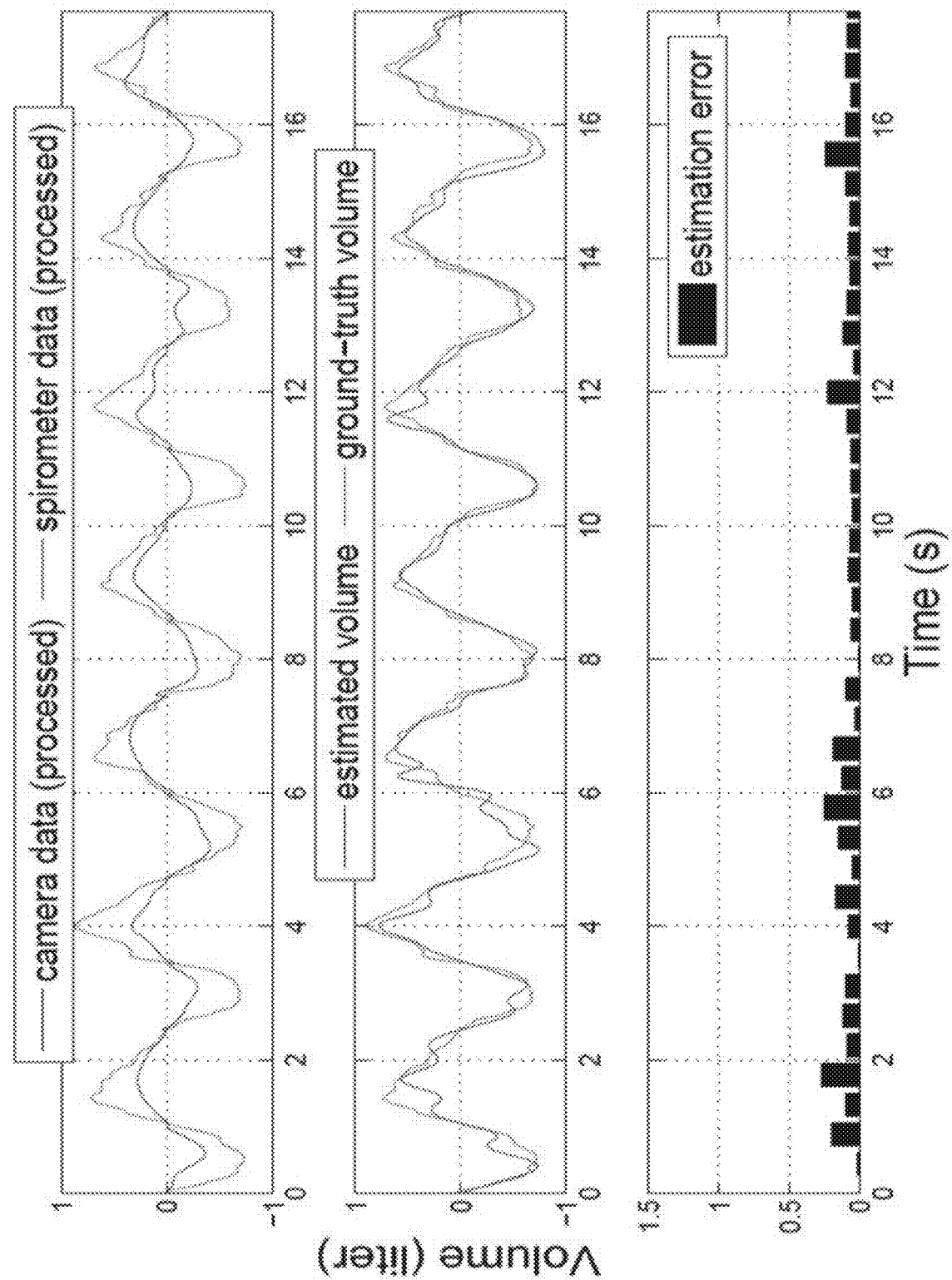
FIG. 21 is a set of graphs showing an example of the processed camera and spirometer correlations. The surface-based estimated tidal volume (top), training-based estimation result (center), and its associated estimation error (bottom).

The resulting data-sets are divided into two sets, one use for training, another one is used for evaluation. This presents the results of estimating the tidal volume using the present technique for four participants where h is the height, w is weight, cs is chest size, and error is the mean error (based on a 0.2 s window). Using the proposed approach 92.2% to 94.19% accuracy within the present tidal volume estimation was obtained with a corresponding 0.055 l to 0.079 l error. FIG. 21 provides a plot of a representative tidal volume estimation of P2.

Figure 22:
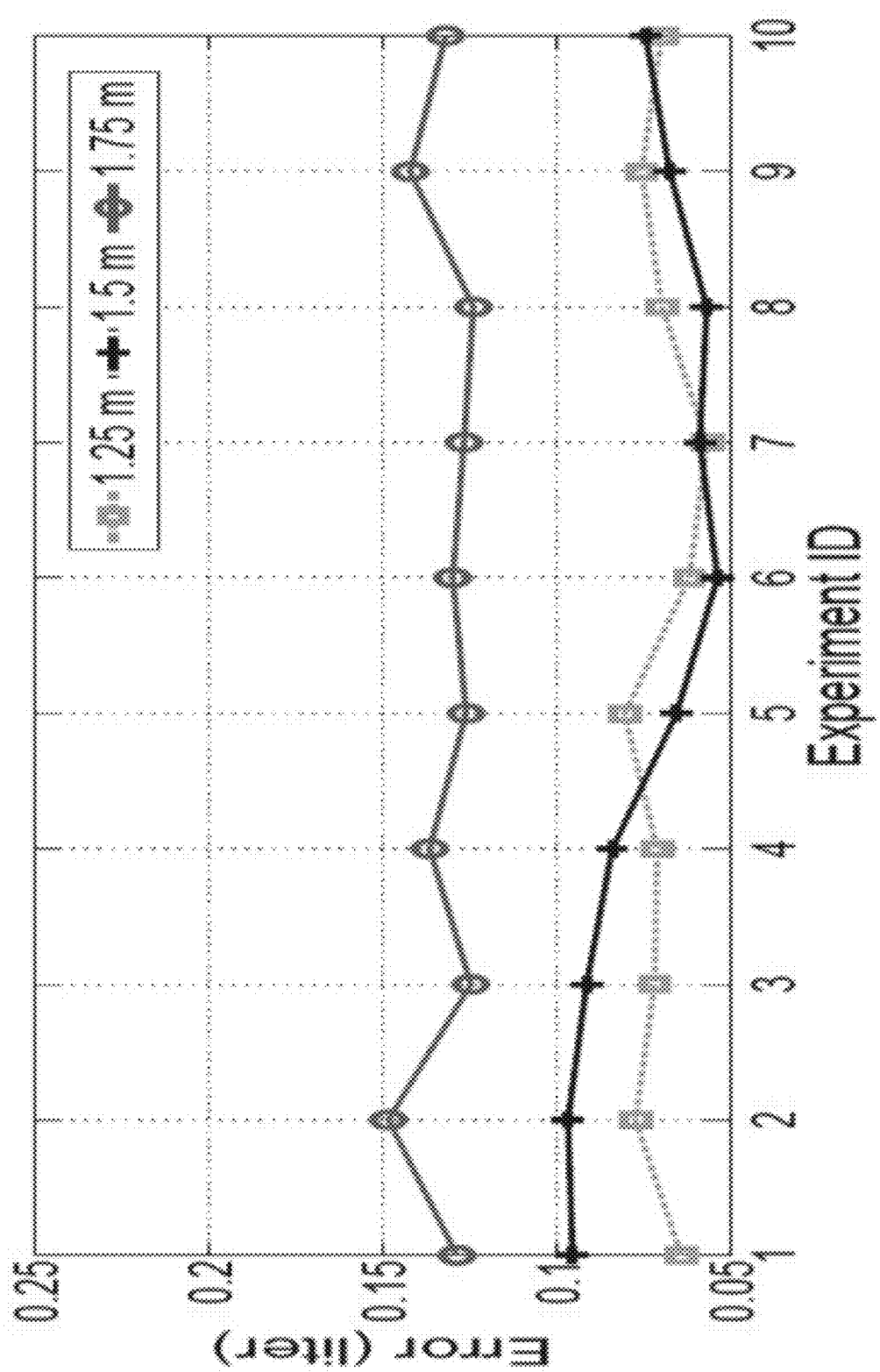
FIG. 22 is a graph of the depth measurement errors as contributed to the reconstructed surface model. Larger distances provide larger fluctuations in depth measurements, incurring the reduction in accuracy of the estimated tidal volume.

3) Distance Impact:

A critical aspect of using depth-based imaging relates to the effective distance of the monitoring device. The noise incurred due to larger distances will introduce errors and reduces the performance of the surface reconstruction process. Experiments were conducted to evaluate the performance of estimation when varying the distance from camera from 1.25 m to 1.75 m. During the process, the student is required to stand in front of the camera and breath through a spirometer when varying the distance between their chest and the camera between each experiment. FIG. 22 shows the error distribution over different distances over 10 experiments (20 s each).

As can be seen from FIG. 22, the system achieves the best performance at the distance of 1.25 m and the worst performance with the distance of 1.75 m. As illustrated within FIG. 22, the performance of estimation is reduced up to 85% (error is approximately 0.15 l) when the distance increases to 1.75 l.

Figure 23:
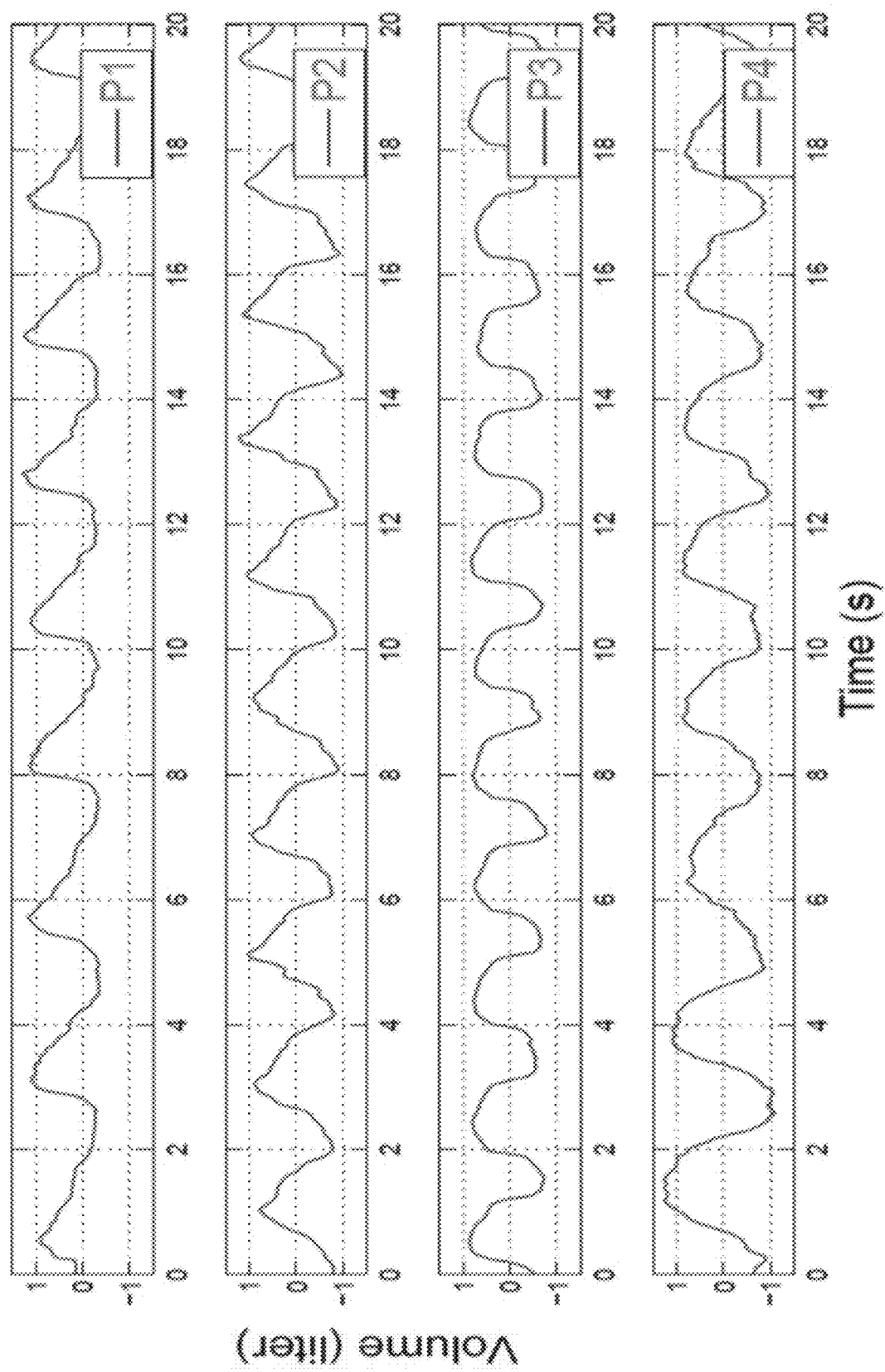
FIG. 23 is a set of graphs of the tidal volume waveforms of participants P1-P4 exhibiting breathing characteristics that uniquely identify their breathing patterns.

4) Medical Significance:

Through the performed experiments, the breathing volume waveforms was found to represent unique patterns of a participant, which can contribute to clinical analysis of the patient's condition. FIG. 23 shows the waveforms of the breathing volumes estimated for four different participants. As can be seen in the FIG. 23 the signals (of different participants) are not only different in frequency and amplitude but also represent unique breathing form characteristics.

This information is not be obtained by existing state of the art rate estimation techniques. Additionally, the results obtained above are independent of the lighting conditions of the patient's environment. Since the device operates off of laser-based depth-images, lighting does not contribute to the requirements for this proposed method.

B. Performance

Figure 24:
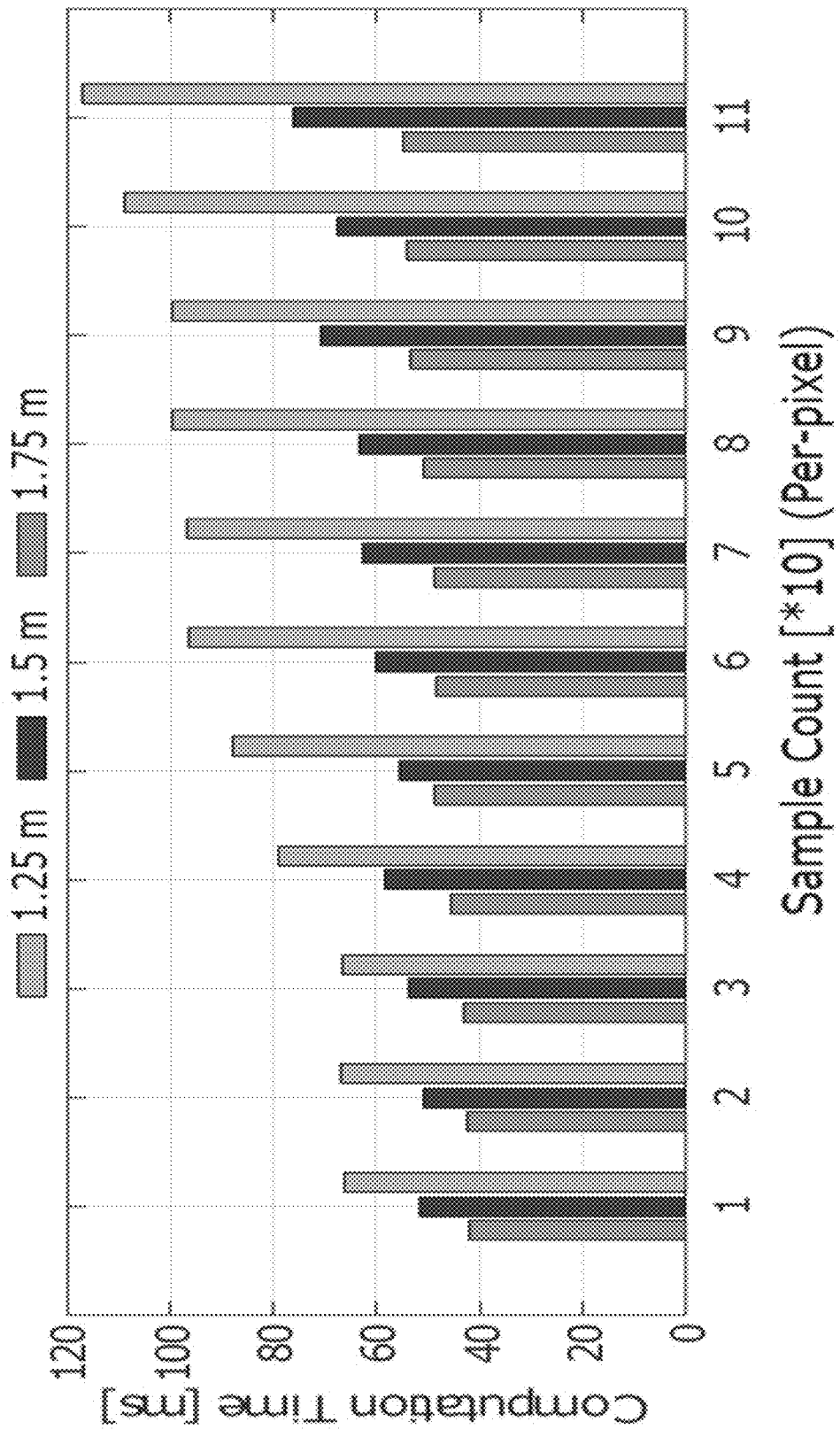
FIG. 24 is a graph showing the computation time of each frame as a function of the number of samples and distance. The experiment was performed at three distances: 1.25 m, 1.5 m, and 1.75 m. For each distance, the number of samples was increased from 1 to 100. At closer distances (1.25 m), higher sampling drastically increases frame computation time.
Figure 27A:
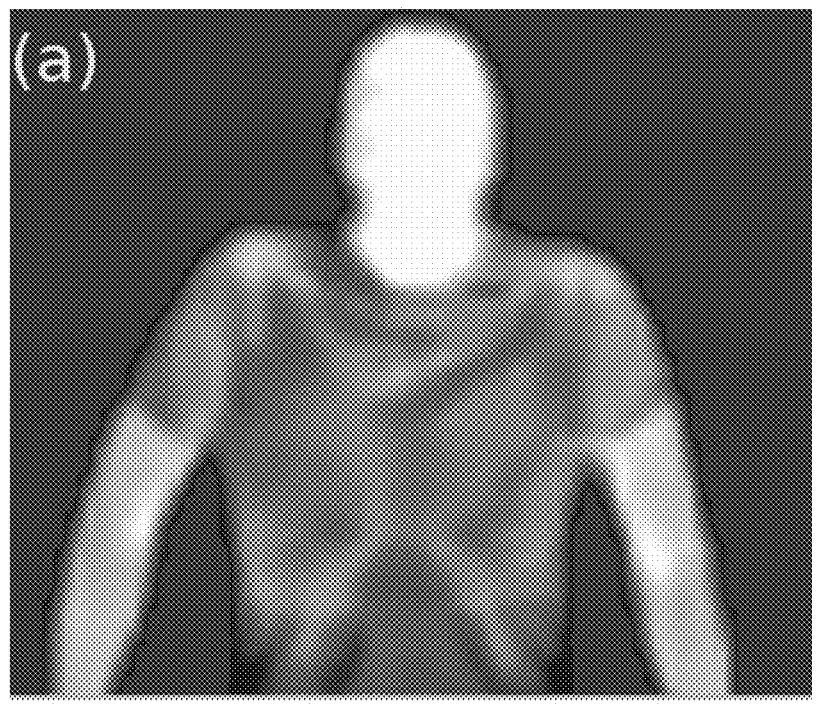
FIGS. 27A-27D are images demonstrating skeletal posture estimation challenges associated with thermal imaging.
Figure 27B:
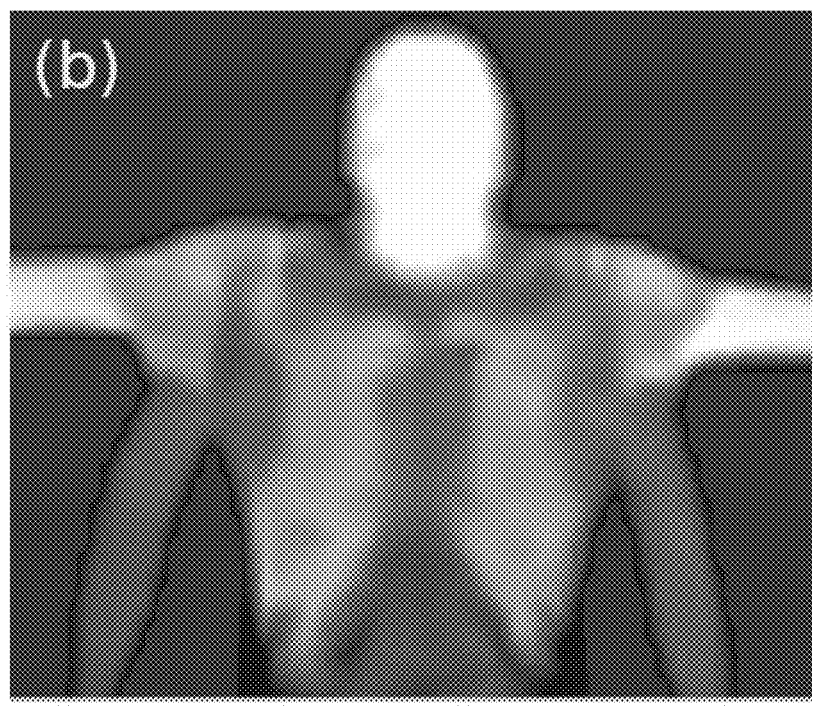
Figure 27C:
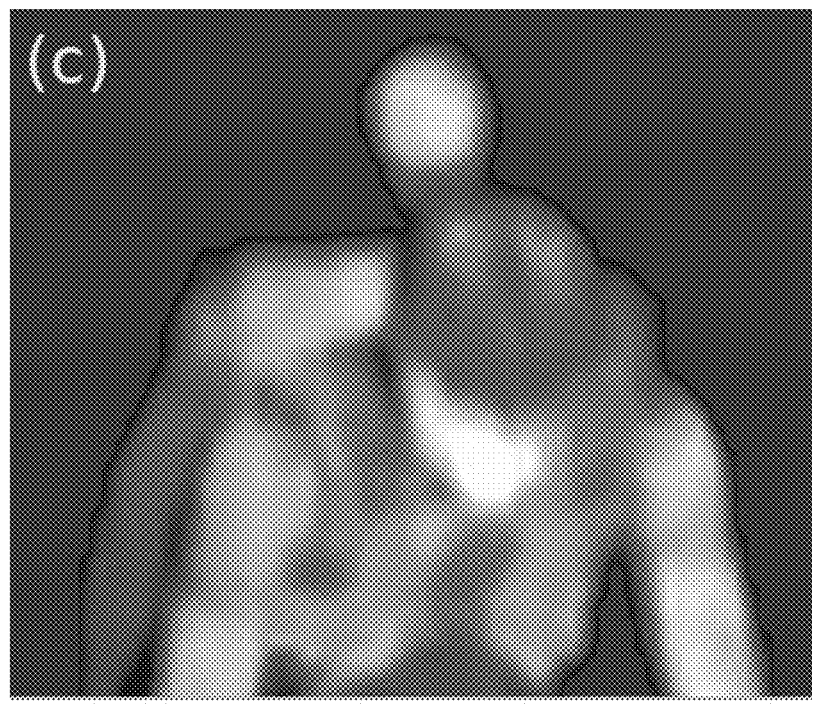
Figure 27D:
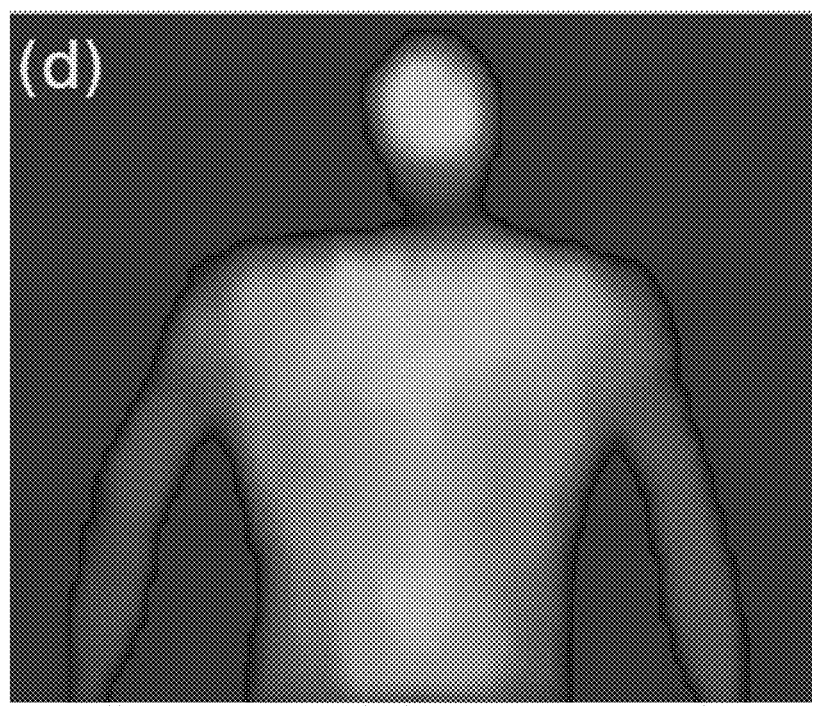

In the analysis of the present proposed tidal volume estimation technique, the computation time required to facilitate the construction of the patient's chest was incorporated along with the corresponding volume. The performance results provided in this section illustrate the results of the optimizations implemented within the present technique to make the proposed realtime monitoring process possible. This is due to the several steps that are required in the present chest surface reconstruction process that are computationally expensive within the realtime domain. Through the optimization of the present technique utilizing performance profilers, a real-time respiratory monitoring system was obtained using widely available hardware. Employing an infrared-based depth-imaging technique, the present approach is subject to the distance measurement errors and fluctuations that are naturally imposed by using this form of depth sampling. Additionally, the present approach does not use an orthogonal projection of the depth-image to generate the associated depth-cloud, thus the number of samples collected on the patient's chest varies as a function of distance. The results in FIG. 24 illustrate the computation times associated with a patient standing 1.25 m, 1.5 m, and 1.75 m away from the monitoring device. For each position the number of samples was increased from 1 to 100. When the patient is closer, depth-cloud density rises, giving a more accurate estimation of the chest surface.

The performance characteristics of the present approach are formed through the four most computationally expensive states. This includes: (1) depth-image sampling with clipping (Kinect-2 with only depth data) 47.77 ms, (2) chest surface normal estimation 9.51 ms, (3) hole filling 1.39 ms, and (4) surface reconstruction 19.73 ms. Due to the inherent inconsistencies in the depth values provided by the Kinect-2, 120 averaged samples per frame are required to effectively eliminate these natural fluctuations. Based on the minimization of these depth measurement errors obtained by averaging several samples per frame, this sampling obtains the largest portion of the frame computation time. Thus the proposed method is currently only limited by the ability to rapidly sample the patient's chest given the sampling rate of the device.

Example 19: Thermal-Depth Fusion for Body Posture Estimation

To provide a reliable means of estimating occluded skeletal postures in any vision-based technique, the proposed method must address the challenges presented by the data acquisition methods used create a solid foundation for performing accurate joint estimations. An immediate extension to current depth based skeletal estimation techniques is the integration of thermal data to both identify and refine potential joint locations by analyzing thermally intense regions of the body and limiting ambiguities within the depth image to provide better joint estimates within the occluded region. However, while this approach of combining both depth and thermal image information alleviates some of the challenges and ambiguities associated with depth-imaging, it also incurs the numerous thermal challenges. Therefore to provide a reliable posture estimation algorithm based on these imaging methods, the challenges introduced by each device were mitigated by forming a new thermal-volumetric model of the patient's body that can provide a robust foundation for thermal-based skeletal joint estimates.

A. Thermal Volumetric Posture Reconstruction

Figure 28A:
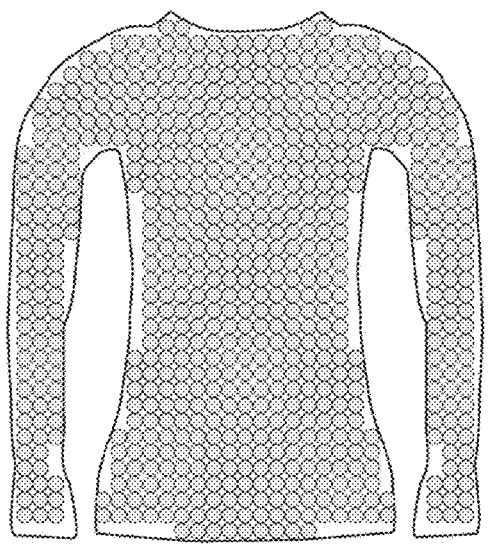
FIGS. 28A-28B are volumetric reconstructions of an ideal skeletal posture.
Figure 28B:
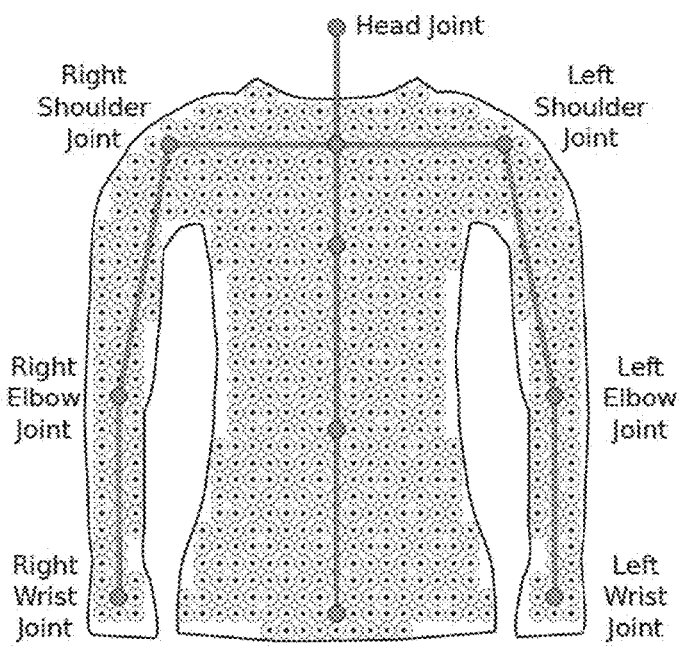

Volumetric reconstruction for posture estimation refers to the process of identifying and generating the extent and geometric characteristics of the patient's volume within the loosely defined region constrained by a depth-surface. This occluded region within the surface will be used to provide what is defined as the posture-volume of the patient. This volume is strictly defined as the continuous region under the occluding surface that contains both the patient and empty regions surrounding the patient that are visually obscured. To define a posture estimate based on this volumetric model, a fixed set of correlated skeletal joint positions was associated within the observed thermal distribution of this volume. This allows a skeletal estimate to be identified from a known (trained) thermal distribution which represents the patient's posture under the occluding medium. FIGS. 28A-28B provide an overview of this ideal posture model, the discrete volume approximation, and skeletal joint structure defined by this model.

This model shifts the foundation of the skeletal estimation from identifying isolated joints in the two-dimensional imaging domain to a three-dimensional voxel model that describes both the volume of the occluded region containing the patient and thermal distribution within this volume due to the heat radiated by the patient's skin. This form of modeling provides a complete 3D image of the patient's posture within the occluded region as an identifiable thermal distribution that can be assigned to an associated skeletal estimates that may contain visually ambiguous joint positions through training.

The development of the volumetric posture model is motivated from three primary observations based on patient thermal images: (1) the process of identifying joint positions from thermal images projected onto the depth surface is highly unreliable due to contact region ambiguities, layering, and non-uniform heat distributions, (2) intense thermal regions within the image are generated by both joints and arbitrary locations on the patient's body, and (3) joints that have a separation distance between the patient's skin and the occluding material may be visually and thermally occluded, meaning that they are not visible, but reside within this volume. Due to these commonly occurring conditions that are not well handled by existing methods, the proposed method is based on creating a correlation between the patient's volumetric thermal distribution and an associated skeletal posture. Based on this correlation, if the known skeletal joint positions are provided for the observed thermal distribution, the patient's skeletal posture can be estimated even when the subject is highly occluded, has several ambiguous joint positions, or the skeletal components are disconnected.

B. Algorithm Overview

The premise of this approach is to reconstruct the unique volumetric thermal distribution of the patient and correlate this posture signature with an associated set of joints that defines the patient's corresponding skeletal posture. The introduction of this process provides a robust method of identifying skeletal estimates on volumetric data that contains unique thermal patterns that are more reliable than depth features within a recorded point-cloud surface. Therefore, based on the present ability to reliably reconstruct this thermal distribution and associated skeletal structure, the resulting correlation is then used to populate a training model of discrete posture variants that can be used to detect a patient's subsequent postures. A high-level overview of the thermal-depth fusion process used to generate a thermal posture signature for a patient is defined below: 1) Thermal Cloud Generation (Depth+Thermal); 2) Patient Volume Reconstruction (Sphere-packing); 3) Surface Heat Propagation (Extended Gaussian Images); 4) Volumetric Heat Distribution (Thermal Voxel Grid).

Figure 29:
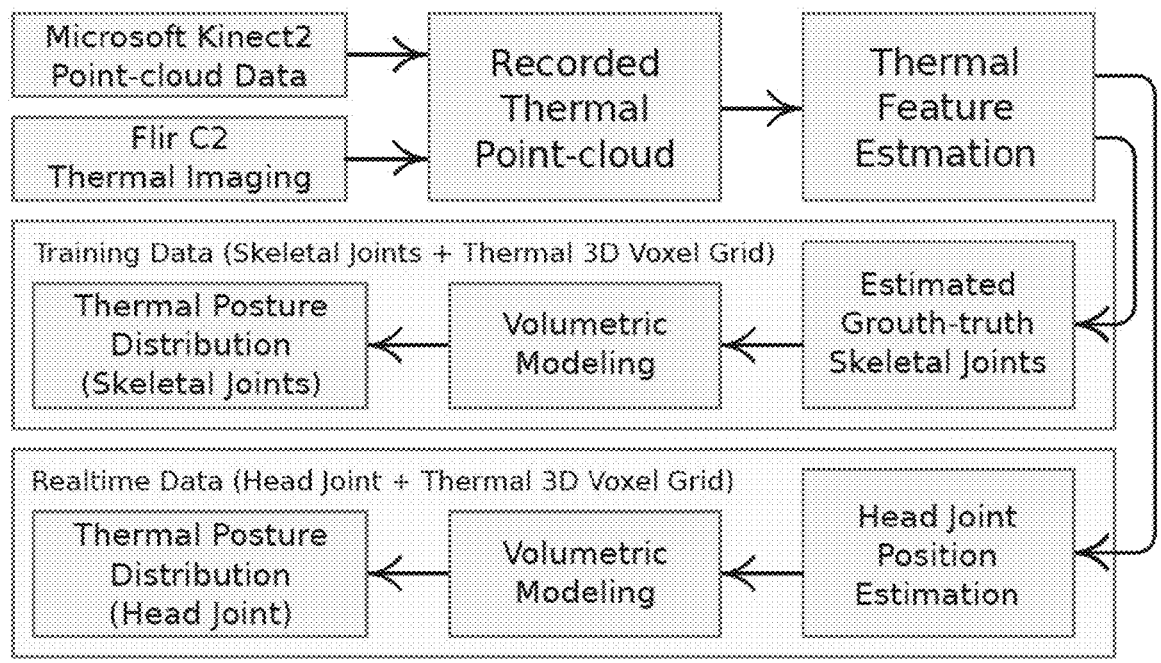
FIG. 29 is a schematic overview of the proposed approach for reconstructing the volumetric thermal data that contributes to the occluded skeletal posture estimation. This includes the generation of the volumetric data with the skeletal ground-truth for training and the real-time data with the provided head joint used during the occluded posture estimation process.
Figure 30A:
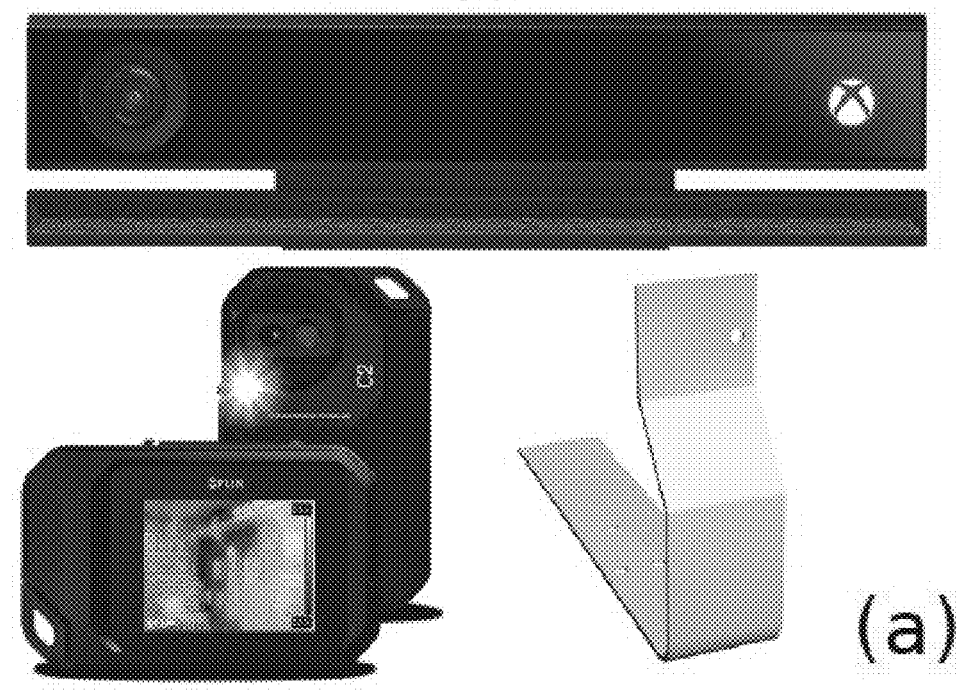
FIGS. 30A-30D are images of the thermal posture device of the invention. Two devices (Kinect2, C2) are mounted with a fixed alignment provided by the bracket shown in FIG. 30A. The images in FIGS. 30B-30D illustrate the mount attached to the bed rail with both devices.
Figure 30B:
Figure 30C:
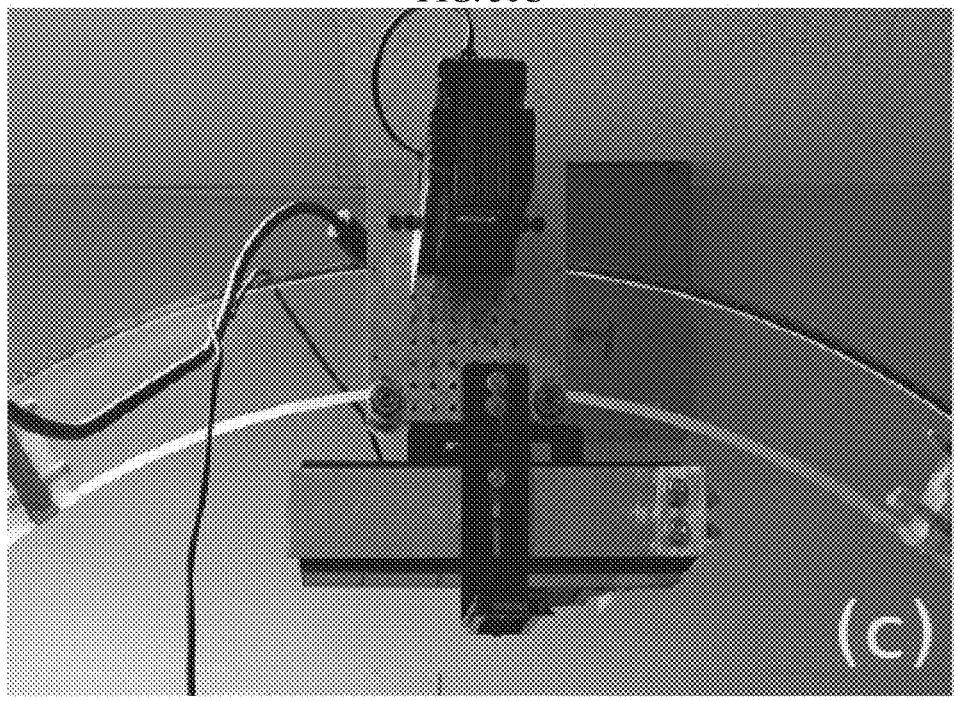
Figure 30D:
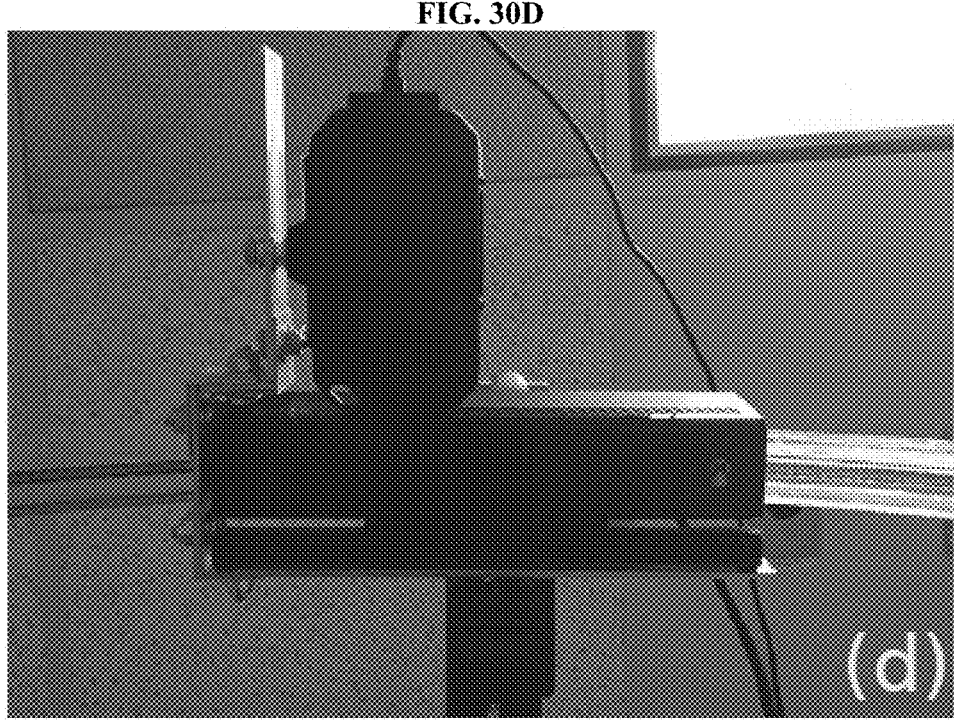

This process is then divided into two primary directions: (1) training for the correlation between the skeletal groundtruth and the associated thermal distribution and (2) the identification of input distributions to retrieve the patient's associated skeletal posture. This forms two different tracks within the core algorithm of the present approach which are defined within the data-flow of the present technique presented in FIG. 29.

Example 20: Devices and Data Acquisition for Thermal-Depth Fusion Body Posture Estimation To facilitate a practical hardware prototype that incorporates these two imaging techniques, the design incorporates two low-cost devices that provide reasonable image resolutions for sleep-based posture estimation within a controlled environment. The present prototype includes the Microsoft Kinect2 for depth imaging and the Flir C2 hand-held thermal imaging camera.

A. Thermal-Depth Fusion Prototype

The Kinect2 provides a depth-image with a resolution of 512×424 and the C2 contains an 80×60 thermal image sensor array which is up-sampled to an image size of 320×240. To configure the overlapping viewable regions provided by each device, a single aluminum bracket was developed to mount the two devices into a simple prototype as shown in FIGS. 30A-30D. Based on the point-cloud data provided from the Kinect2 depth-image, the thermal intensity at each point from the corresponding point within the up-sampled thermal image provided by the C2 was integrated to generate the thermal-cloud of the volume enclosing the patient due to the occluding material.

The alignment of the images provided by these devices requires further image processing due to the vastly different field-of-view (FOV) provided by each device. Therefore the alignment transformation of the two camera was modeled based on a simple linear transformation as a function of the distance to the bed surface. Additionally, due to the limited FOV of the C2 device, the device was rotated by 90° to provide the largest overlapping field-of-view possible.

B. Occluded Skeletal Estimation Ground Truth

Figure 31A:
FIGS. 31A-31C are images of thermal posture ground-truth and training suits, without (FIG. 31A) and with (FIG. 31B) attachable metal spheres. The suit is worn during the training process to identify the relationship between the patient's thermal volume and joint positions.
Figure 31B:
Figure 31C:

One of the prominent challenges introduced with occluded skeletal posture estimation is the inability of most vision-based techniques to provide a reliable ground-truth estimation of the patients skeletal posture while the occluding material is present. For imaging techniques, this is a direct result of the interference or complete occlusion of the patients posture due to the external surface properties of the material that are obtained through using limited regions of the electromagnetic spectrum (such as the visible or infrared wavelengths). The reflection based nature of these techniques minimizes the ability to correctly infer surface features that correctly contribute to the patient's occluded posture. While other methods utilizing these reflection-based imaging techniques have introduced interesting ground-truth workarounds for approximating the surface behavior of the occluding surface, this remains a significant challenge in occluded posture estimation methodologies and evaluation models. To address this challenge a new thermal based skeletal ground-truth derived from common motion capture systems was introduced. As with common motion capture systems, this simple thermal marker system is designed from a standard form-fitting suit equipped with 9 solid nickel spheres with an approximate diameter of 3.0 cm. These solid metal spheres are attached to the suit at various locations that correspond to the joint positions of the patient. During the training process, these markers emulate the methodology of tracking known joint positions. This provides a highly-accurate method for providing a ground-truth of the patient's posture while an occluding surface is present. The image provided in FIGS. 31A-31C illustrate the simple design of the training suit with the attached solid nickel spheres used in the training process.

Figure 33B:
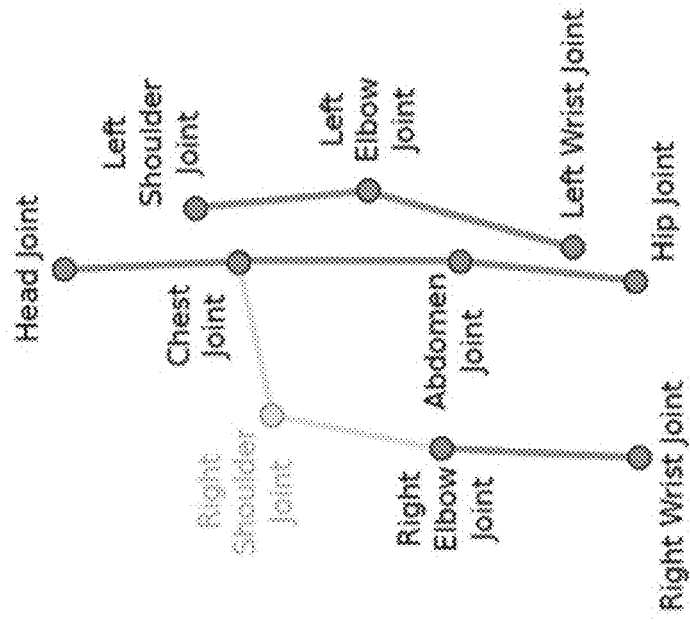
FIGS. 33A-33B are diagrams representing thermal skeleton ground-truth. The ground-truth skeleton presented in FIG. 33A illustrates a complete skeletal posture based on every supported joint being identified. The skeleton presented in FIG. 33B represents the patient in a left facing posture with the right shoulder joint completely occluded.
Figure 33A:
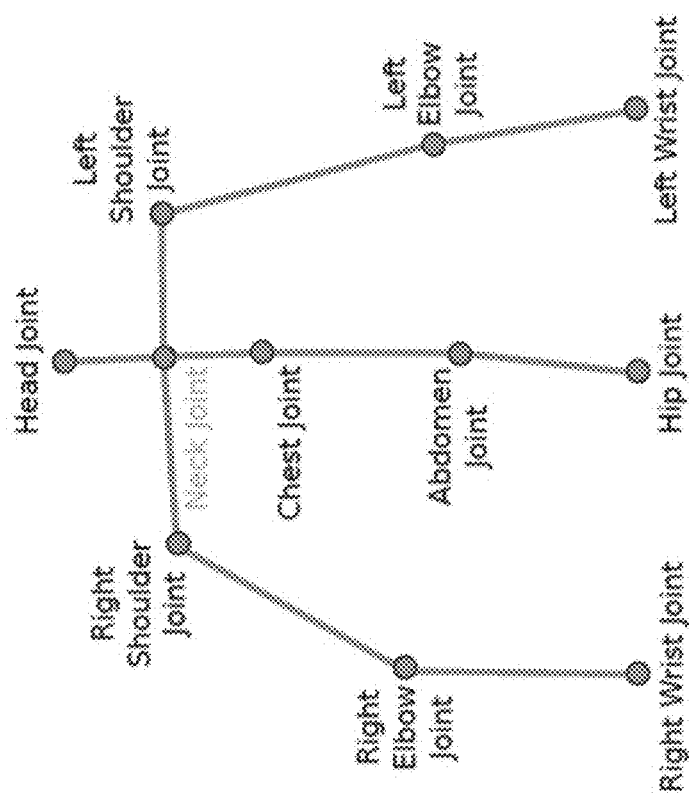

The result of the thermal skeletal ground-truth is the product of a simple adaptive thresholding and a connected-component algorithm that identifies the thermally intense regions of the spheres within the image. In the resulting thermal-cloud, the spheres appear as small white regions indicating the locations of the joint positions, as shown in FIG. 32G. For each grouping of points belonging to a joint, the unique joint position is calculated as the center of mass of this cluster. For labeling a simple semi-automated tool was employed to assist in the identification of the skeletal joints for the training data. Based on the provided adjacencies, the system will automatically generate the required skeleton. For occluded joints, a partial skeletal structure was introduced (FIGS. 33A-33B).

The disconnected skeletal structure provided presents a best-case posture estimate based on the provided thermal information within the model. This allows to provide a partial solution for instances where the occluding material may prevent several joints from being recognized in both thermal and depth images, for which no obtainable solution was obtained.

Example 21: Volumetric Thermal Modeling

Sleep-study occluded posture estimation offers a large reduction in both the degrees of freedom in both the patients movement and the volumetric region they occupy. Based on the assumption that the patient resides at rest within a limited region and the occluding surface is covering the patient, this region of interest is easy to identify and model as a continuous enclosed volume as illustrated in FIG. 32F. This is achieved through the use of several assertions about the experimental setup: the patient resides within the bounded region and is supported by a rest surface, the occluding surface is supported by the patient's body and does not penetrate through the volume of the body, the human body is contiguous, and the patient's face is visible and unobstructed. In this Example one builds on these assumptions to formulate the three-stage process of building the patient's posture volume and generating the associated volumetric model: (1) volume enclosure, (2) sphere hierarchy generation, and (3) the generation of a voxel grid that represents the thermal distribution of the patient's posture.

A. Posture Volume Enclosure

To begin the process of imposing constraints on the possible joint locations within the occluded region, the volume between the recorded depth image and the known bed surface was enclosed. Since the enclosed volume is a direct function of the occluded surface model provided by the point-cloud and the bed surface, it was assumed that the contact surface of the bed can be obtained by a simple planar model or through a preliminary scan of the bed surface taken while patient is not present.

B. Volumetric Sphere Hierarchy

To model the internal volume of the patient behind an occluded region, a simple and robust method for populating the area was introduced using discrete unit spheres through a methodology derived from simple sphere-packing. Generating this volume requires an enclosed region that is defined by the point-cloud data provided by the imaging devices included in the proposed prototype. From the enclosed region occupied by the patient defined by the beds surface and the recorded depth image, the volumetric reconstruction process used to define the occluded volume is derived from the 3D grid-based spherepacking algorithm used to generate a spherical hierarchy.

This methodology is used as the basis of the volume reconstruction algorithm due to two assertions of the cloud that encapsulates volume of the patient: (1) the volume may be concave and contain complex internal structures and (2) the internal region may contain holes or regions that further reduce the patients potential joint positions due to volumes that are too small to occupy the associated joint.

Figure 34A:
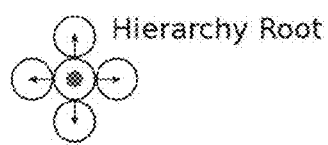
FIGS. 34A-34B are images showing two-dimensional variants of the volumetric reconstruction algorithm.
Figure 34B:
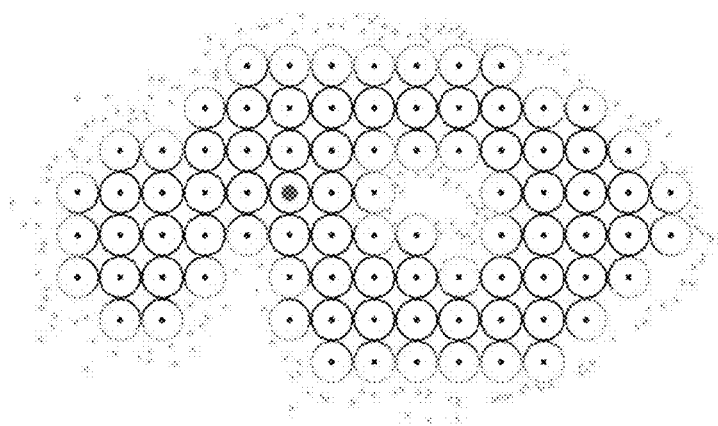

Sphere-packing is a simple algorithm that propagates unit spheres through a hollow region until some boundary conditions are met. This is based on three primary components commonly defined for sphere-packing: (1) the start position of the propagation, (2) the method of propagation, and (3) the boundary conditions must be defined for each sphere added to the volume. For (1), the starting position of the propagation is defined as the center of mass of the patients head. From the present assertion that the patients head will always be uncovered, one can easily segment and identify the patients head within the thermal image due to the heat intensity of the patients face. The method of propagation (2) is derived from a bread-first search pattern. For the boundary conditions (3) of the propagation, two primary boundaries were considered: the pointcloud that encloses the region and regions that have very limited thermal intensities. This limits the propagation of the volume to regions that contribute to the patient's posture. The images in FIGS. 34A-34B illustrate this thermal 2D sphere-packing algorithm. For the present three-dimensional skeletal posture data, the root position resides within the head of the patient.

C. Thermal Extended Gaussian Images (TEGI)

Extended Gaussian Images (EGIs) represent a mapping of surface normals of an object onto a unit sphere through a simple projection. This formulation provides an alternative form of representing complex geometric structures using a simplified form while maintaining the original geometric representation. To reduce the resolution of the volumetric data provided by the thermal-cloud, the use of Thermal Extended Gaussian Images (TEGIs) was introduced to represent a projection of localized thermal intensities from the recorded thermal images onto the surfaces of the unit spheres within the sphere hierarchy.

TEGIs are introduced to establish a transfer function between the known recorded surface temperatures and the volumetric data represented by the sphere hierarchy within the occluded region. This function represents a conversion of the 2D thermal data residing within the surface lattice to a volumetric representation of the transferred heat and an estimate of the source direction. This allows the thermal data of the recorded surface point-cloud to be transferred to the newly generated internal volume that represents the patients potential posture constraints. Based on this model, TEGIs are used to represent both thermal intensity and directionality of the observed thermal distribution.

Each surface sphere within the hierarchy contains an TEGI that is parametrized by two characteristic features based on the on the sample points residing within the local neighborhood (2r) of the sphere: (1) the thermal intensity t and (2) the Euclidean distance d between the contributing point and the sphere. This provides a parameterized distribution that models the local heat distribution across the surface of the recorded thermal cloud as a 2D Gaussian function TEGI(t, d):

$$TEGI(t,d) = \alpha t e^{[-x^2/2(\beta d)] + [-y^2/2(\beta d)]}$$

Where the parametrization of the standard Gaussian distribution is defined by the thermal contribution t and scaled by a scalar thermal multiplier $\alpha$ provided by the thermal image. The distribution of the function is then modified by modeling $\sigma^2$ as the Euclidean distance between the point d and the center of the sphere with a distance scalar multiplier $\beta$ where the value for the scalar multiplier $\beta$ is defined by the device distance to the surface of the patient.

Figure 35A:
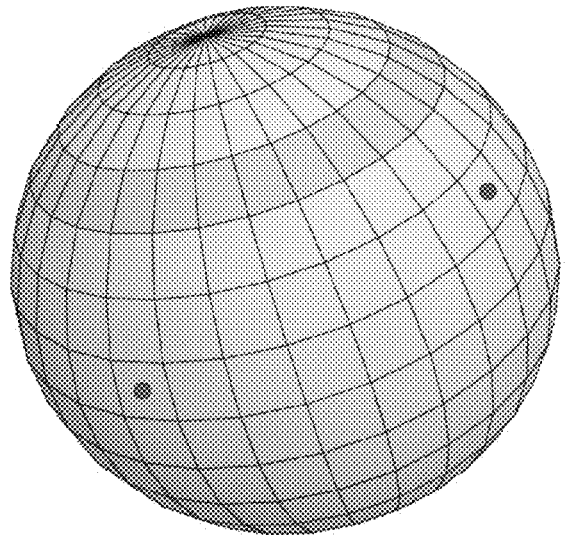
FIGS. 35A-35B are images showing Extended Gaussian Image (EGI) spherical mapping. For each thermal point within the recorded thermal point-cloud, the projection of the point will produce a location on the unit sphere that will reside within a bounded surface region. These surface regions are defined by the height and width of the EGI map in FIG. 35B. The corresponding surface regions in FIG. 35A are displayed in the two-dimensional representation in FIG. 35B.
Figure 35B:
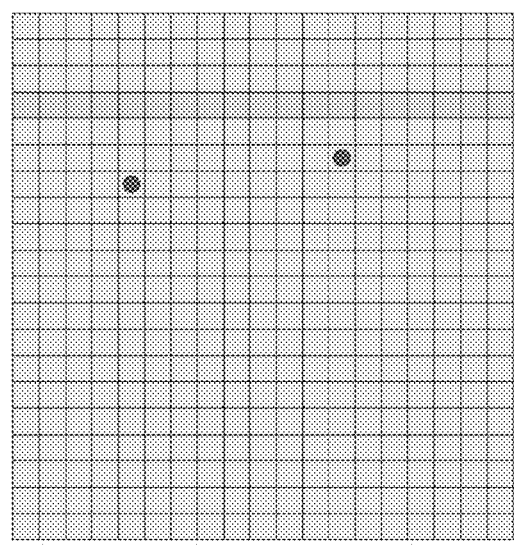
Figure 37A:
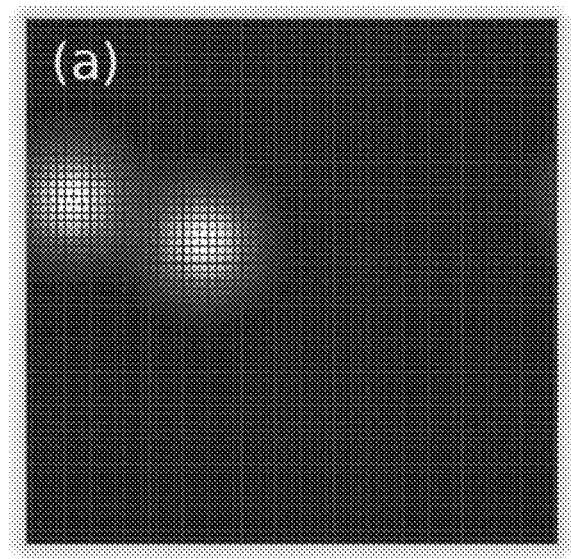
FIGS. 37A-37C are Thermal Extended Gaussian Images for the distribution of heat due to surrounding thermal points.
Figure 37B:
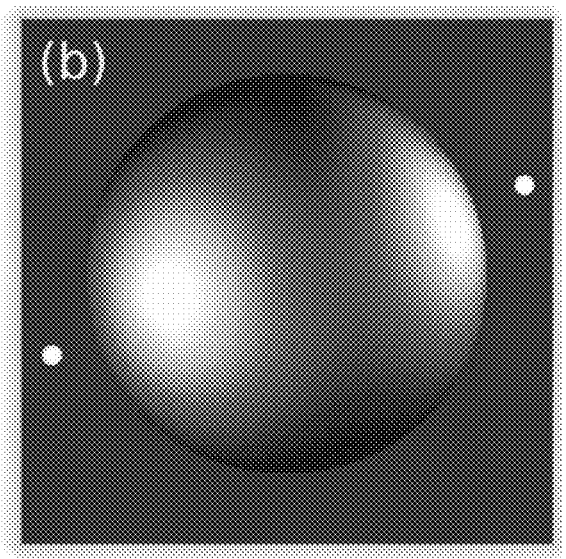
Figure 37C:
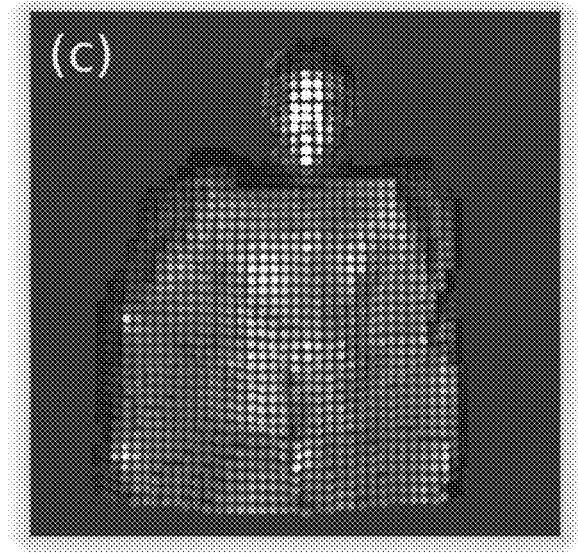

The primary requirement of generating a TEGI is a procedure for projecting and mapping thermal points from the thermal cloud onto the surface of a unit sphere. To achieve this, a discrete form of the unit sphere is divided into discrete regions for automated point-cloud alignment. Then for each point within the local neighborhood, the point is projected onto the surface of the sphere and then assigned a 2D region index within the TEGI. This index will be used to identify the peak of the Gaussian distribution that will be added to the discrete surface representation of the sphere. Since the resolution of the Gaussian is discretized on the surface of the sphere, the continuous parameterized Gaussian function was sampled at a fixed interval and the distributions were allowed to wrap around the surface of the sphere. The images in FIGS. 35A-35B provide an illustration of how points are projected to the surface of a unit sphere and then used to generate the positions of the Gaussian distributions within the surface image of the sphere.

The contribution of multiple points within the same local neighborhood is accounted for through the addition of several different Gaussian distributions to the surface of the sphere, each with its own parameterization derived from its relative position to the sphere and its thermal intensity. The resulting TEGI is then defined as the sum of the contributions from all local points within the defined search radius. This defines the total thermal contribution of sphere S to the volume for the set of points within the spheres local neighborhood N:

$$S(p) = \sum_{i=0}^{n} \sum_{j=0}^{n} \alpha p_t e^{-x_i^2/2(\beta d) + -y_j^2/2(\beta d)}, \forall p \in N$$

Geometrically, the contribution of each points thermal intensity to the surface of the sphere also incorporates the directionality of the thermal intensity of the point in the direction of the sphere. This provides a rough estimate as to the direction of the source of the thermal reading identified at the surface point. While this approximation of the heat transfer function does not provide an accurate model of the inverse heat transfer problem, it provides an effective means for estimating the inverse propagation of the heat measured at the recorded depth-surface to define the thermal signature of the volume.

These TEGIs are then evaluated for each sphere in the spherical hierarchy that reside within the surface of the thermal cloud. The resulting thermal intensity of each sphere is then used as the seed for propagating the observed heat through the patient's posture volume. These thermal values are then used generate a three-dimensional voxel model of the patients heat distribution.

D. Thermal Voxel Grids

Figure 38A:
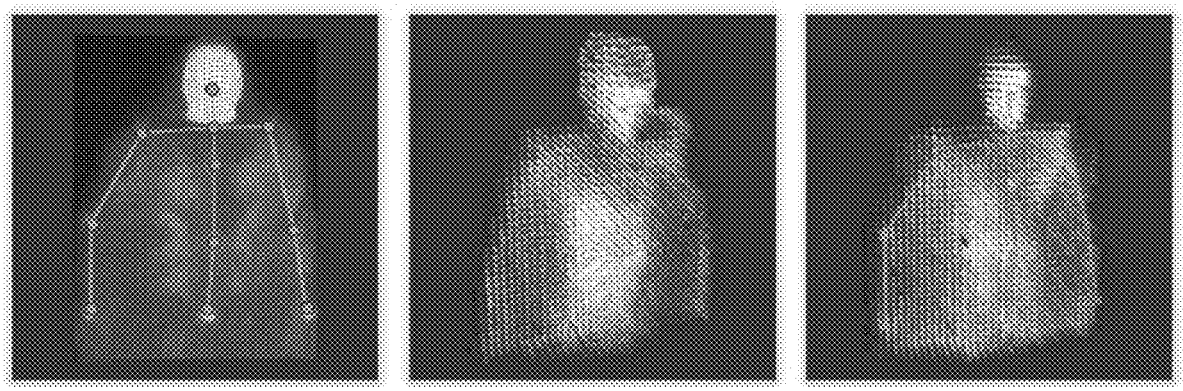
FIGS. 38A-38F are images showing skeletal posture estimation results for six standard sleeping postures. The first image in each sequence provides the ground-truth skeletal posture, followed by the middle image that illustrates the thermal distribution used to obtain the trained skeletal posture rendered in the last image of each sequence.
Figure 38B:
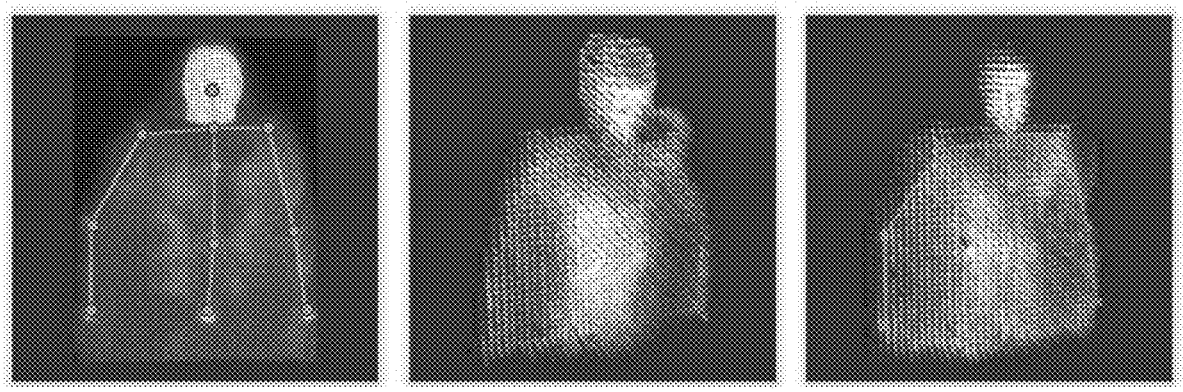
Figure 38C:
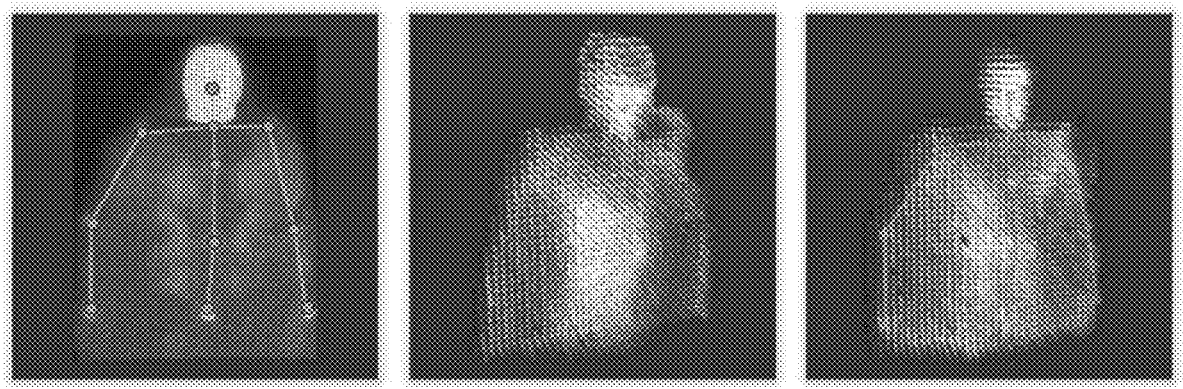
Figure 38D:
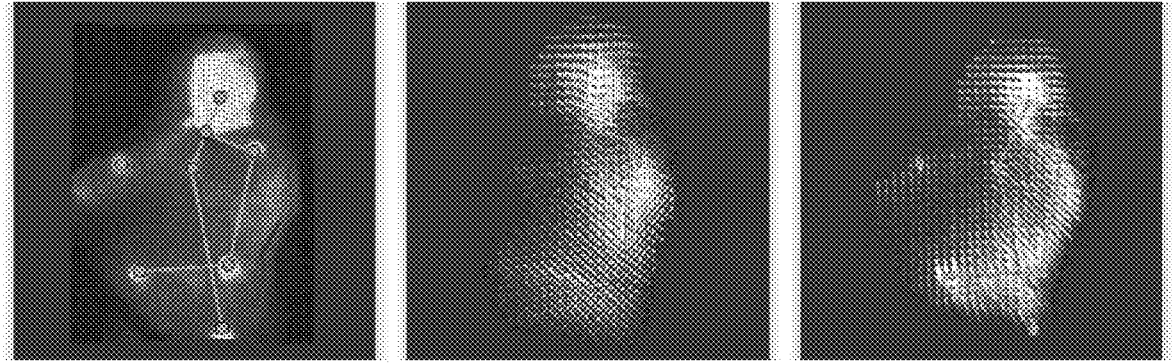
Figure 38E:
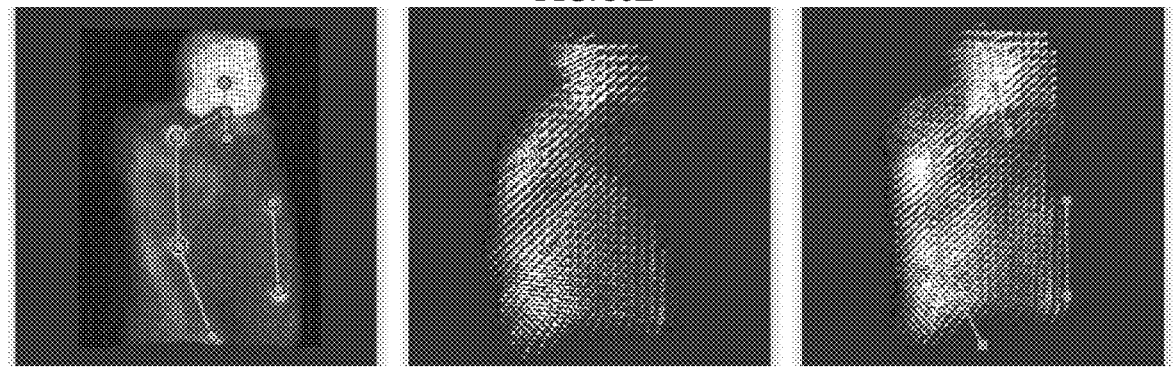
Figure 38F:
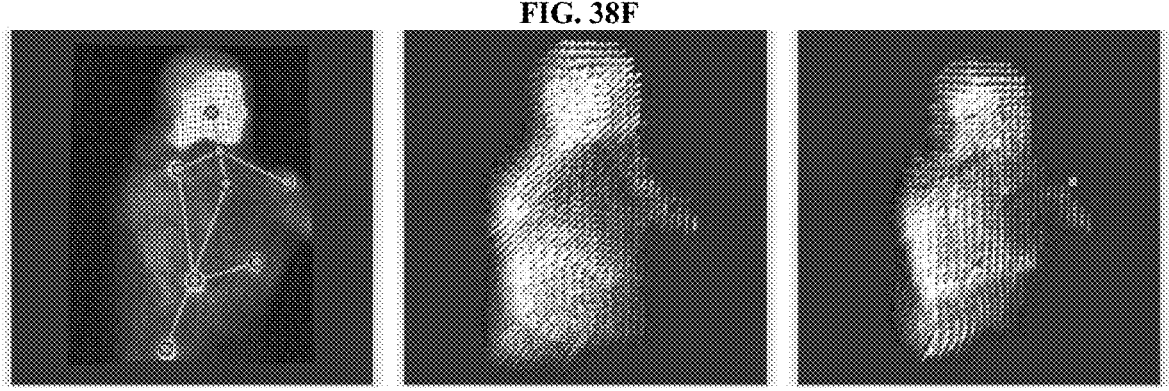

To integrate the thermal contribution of each TEGI within the constructed sphere hierarchy, the grid-based nature of the propagation algorithm used to generate the volume is used to populate a scalar field of the thermal values into a voxel grid. This fixed-dimension voxel grid provides the thermal distribution of the internal volume of the patient used to represent the thermal distribution of a unique posture. The thermal distribution residing within the voxel grid is then used to represent the patient's posture as a 3D image that can be classified based on a pre-trained set of postures. An example of the resulting 3D image illustrating the patient's posture within the voxel grid is illustrated in FIG. 38D.

Example 22: Thermal Skeletal Volumetric Training

The underlying correlation between volumetric thermal distributions and skeletal joint positions used to formulate the present posture estimation is defined by two primary factors: (1) the skeletal ground-truth of a patients posture and (2) the thermal distribution of the patients volume within the occluded region. Together, these two components form the training and identification data used to estimate the occluded skeletal posture of the patient within an occluded region.

Neural Network Structure

There are several types of training methodologies and models that have been designed for three-dimensional medical image classification. Of these methods, Convolutional Neural Network (CNNs) and Deep Neural Networks (DNNs) are most commonly used methods for identifying complex structures within 3D images. In the proposed method, a feedforward CNN-based network structure was selected to handle the higher dimensionality of the 3D thermal voxel grid generated within Example 21. This is due to the dense representation of the patient's thermal distribution rather than a feature-based estimation which would better suit a DNN-based method. Therefore the CNN was allowed to generate features through sequential filters that identify thermal-specific classification metrics. In the present method CNN was implemented with 4 fully connected layers with rectified linear units (ReLUs) which obtain results faster than traditional tanh units. Additionally, since there is no analytical method to determine the optimal number of convolutional layers for a given application, the present network structure is determined empirically based on the correct identification of posture states. Training Model. CNNs were trained to detect 6 postures of the patient based on the present generated thermal voxel grid images. The classification label (one of six postures) is assigned for each thermal distribution. 60 thermal voxel grid images are used for training while 180 other distributions have been used for testing. Overfitting was avoided through two common methods: First, Dropout was applied to randomly drop units (along with their connections) from the neural network during training, which prevents neurons from co-adapting. Second, cross-correlation is applied to stop the training when the cross-validation error starts to increase, leading to the present termination condition. Additional convolutional layers generally yield better performance but as the performance gain is reduced, diminishing returns were see in the training process. Therefore the number of connected layers required to avoid overfitting is commonly defined as two.

Example 23: Experimental Validation of Thermal-Depth Fusion Body Posture Estimation Driving the experimental results of the proposed volumetric model for skeletal posture estimation, several common sleep postures were identified that exhibit a wide variety of skeletal joint positions that form both partial and complete posture estimates due to the visual occlusions introduced by the use of a standard blanket. Based on these common postures, the present objective is to collect the skeletal ground-truth, generate the associated thermal distribution, and then correlate this distribution with the recorded skeletal joint positions for the patient's training set. From the generated training set, the patient's approximate skeletal posture can then be estimated solely based on their current thermal distribution.

Standard Posture Estimation.

The primary qualitative metric for both identifying a patient's posture and associated skeletal structure in occluded regions is based on the ability to recognize the posture and the accuracy of the generated skeletal joints used to represent the patient. In these experimental results, a quantitative analysis was perform for the accuracy of this method with respect to identifying the correct posture based on the generated thermal distribution. The image sequences in FIGS. 38A-38F illustrate six common postures along with their associated ground-truth skeletal measurements as the first image within each sequence. The posture sequence for these experiments is defined as: (a) face up+arms at the side, (b) face up+hands on chest, (c) face left+straight arms, (d) face left+bent arms, (e) face right+straight arms, and (f) face right+bent arms. The second image within each sequence provides the rendered thermal distribution of the patient based on the voxel data generated from the volumetric model. This data is then used to identify the associated skeletal structure, as presented in the last image of each sequence.

Individualized Posture Estimation.

Figure 39:
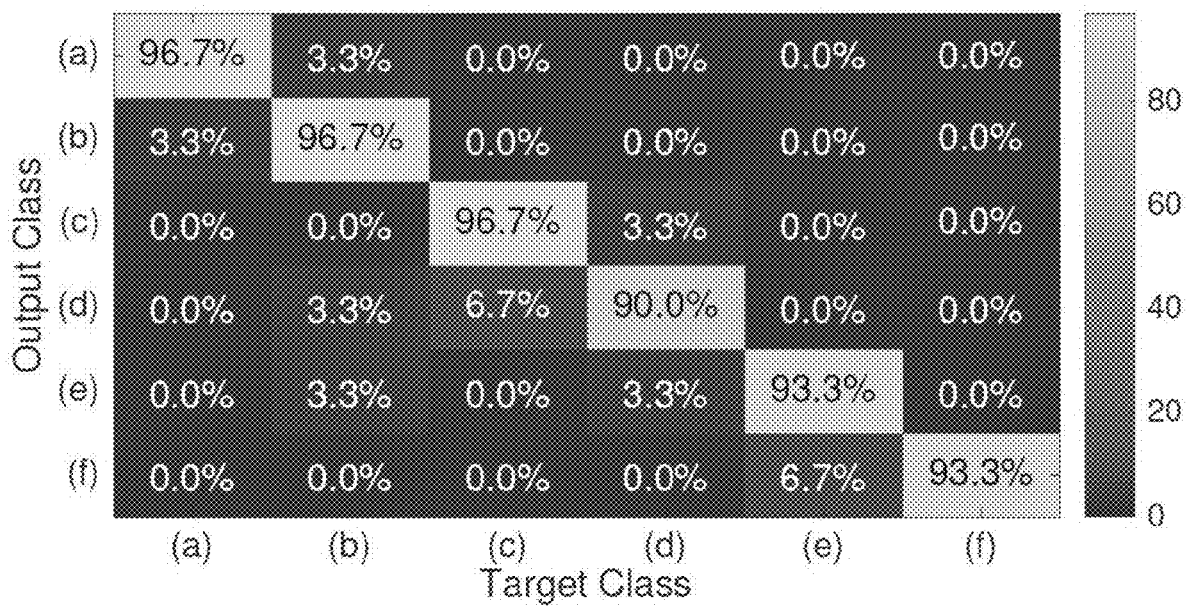
FIG. 39 is an individualized confusion matrix for the six postures depicted in FIGS. 38A-38F. The correlation between the postures, illustrates a ≈90% classification accuracy. Similar postures incur misclassification due to changes in the patient's joint locations (such as the wrists or elbows).

As the primary quantitative metric of the volumetric distribution method, the accuracy of the classification of the patients posture was measured based on the present six standard postures. For each posture, the ground-truth and 40 variants (with subtle movements) were collected to provide a sufficient training set applicable to the limited posture set. This results in 240 data sets in total, with 60 used for training and 180 data sets utilized for testing. The confusion matrix illustrated in FIG. 39 shows the performance of the classification rate for the trained system, resulting in an average ~94.45% classification accuracy.

Cross-Patient Posture Estimation.

Figure 40:
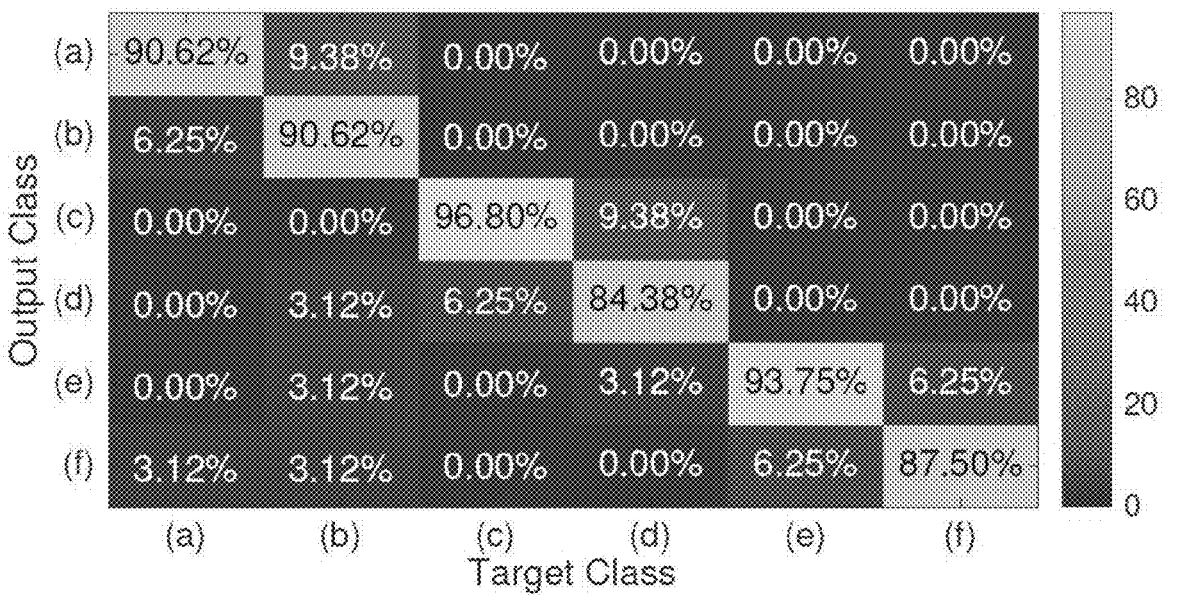
FIG. 40 is a confusion matrix illustrating the accuracy of the posture estimation tested against a set of 3 patients that did not contribute to the training of the CNN used to perform the classification.

Individual body structure plays a significant role within posture estimation algorithms that do not use features, however based on the generalized volumetric model of the body used to classify the identified skeletal posture, this method can also be applied across several patients with similar body shapes and sizes, obtaining reasonable results. The confusion matrix in FIG. 40 shows the classification results of the postures provided by three individuals based on a pre-trained posture set formed from a single individual, with avg. accuracy ~90.62%.

Impact of Training Network Structure.

The introduction of additional layers within the CNN improves the performance of classification in both experiments, but diminishing returns were still observed. The CNN from 1 to 4 convolutional layers was tested, and the corresponding classification accuracies of the individualized experiment are illustrated within Table 2.

TABLE 2

CNN Posture Classification Performance

| | # of convolutional layers | | | |
|---|---|---|---|---|
| | 1 | 2 | 3 | 4 |
| Accuracy (%) | 76.67 | 88.33 | 91.67 | 94.45 |
| # of weights (millions) | 1.2 | 2 | 2.8 | 3.11 |
| Training time (minutes) | 4.5 | 8.5 | 15 | 20.5 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An apparatus for measuring and monitoring breathing volume of a subject, comprising:
   a directional radio wave emitter;
   a directional radio wave receiver, wherein the emitter and the receiver are positionable such that the emitter emits a continuous radio wave to a plurality of areas of a chest of the subject and the receiver monitors the radio wave that is reflected by the plurality of areas of the chest of the subject to generate chest movement information associated with the plurality of areas of the chest of the subject; and at least one computing device coupled to: the emitter, the receiver, and a spirometer, the computing device configured to:

during a training session:

train a plurality of neural networks, wherein each neural network of the plurality of neural networks is associated with an area of the plurality areas of the subject's chest, and wherein the plurality of neural networks implement non-linear correlation functions that relate the chest movement information associated with corresponding areas of the chest of the subject to breathing volume information from the spirometer; and during a monitoring session:

identify the area of the chest of the subject to which the emitter points the radio wave; and select, based on the identified area, one of the plurality of neural networks to be used to generate a breathing volume estimation.

2. The apparatus of claim 1, wherein the radio wave emitter emits a single tone continuous radio wave at about 2.4 GHz.

3. The apparatus of claim 1, wherein the at least one computing device is further configured to:

decode the reflected radio wave to extract interfering signals due to at least one of: respiration, heartbeat, and random body movements, of the subject;

detect a change in a body posture of the subject based on a change in the interfering signals; and upon detecting the change in the body posture, reposition at least one of the emitter, and the receiver, to a position sufficient to extract the interfering signals.

4. The apparatus of claim 3, wherein the at least one computing device is further configured to identify ne of a plurality of mapping relationships for calculating the breathing volume for the subject in the changed body posture.

5. The apparatus of claim 1, wherein the radio wave receiver collects and outputs data at a sampling rate of about 1 kHz to about 100 kHz.

6. The apparatus of claim 1, wherein the at least one computing device is further configured to detect large- and small-scale body movement and radar occlusion in the subject.

7. The apparatus of claim 1, wherein the emitter and receiver are mounted on a mechanical motion control system, the apparatus further comprising a controller to control the mechanical motion control system.

8. The apparatus of claim 7, wherein the mechanical motion control system is capable of rotating the radio wave emitter and radio wave detector with 360° of freedom on three axes.

9. The apparatus of claim 7, wherein the mechanical motion control system is mounted on a track.

10. The apparatus of claim 9, wherein the mechanical motion control system is capable of motion across the chest of the subject.

11. The apparatus of claim 9, wherein the mechanical motion control system is capable of motion along the length of the subject.

12. The apparatus of claim 7, wherein the mechanical motion control system is mounted on a bed or another horizontal platform on which a subject lies.

13. The apparatus of claim 1, wherein the spirometer is capable of measuring the subject's breathing volume of the subject.

14. A kit comprising the apparatus of claim 1 and instructions for the operation of the apparatus.

15. The kit of claim 14, further comprising a software program product including program instructions that, when executed by the at least one computing device, facilitate processing of data collected by the apparatus.

16. A method for measuring and monitoring breathing volume of a subject, the method comprising:

positioning: a directional radio wave emitter, and a directional radio wave receiver, in view of a chest of the subject;

emitting, using the emitter, a continuous radio wave to a plurality of areas of the chest of the subject;

monitoring, by the receiver, the radio wave that is reflected by the plurality of areas of the chest of the subject;

generating, by a computing device coupled to: the emitter, the receiver, and a spirometer, chest movement information associated with the plurality of areas of the chest of the subject;

during a training session:

training, by the computing device, a plurality of neural networks to implement non-linear correlation functions that relate the chest movement information associated with corresponding areas of the chest of the subject to breathing volume information from the spirometer, wherein each neural network of the plurality of neural networks is associated with an area of the plurality areas of the chest of the subject; and during a monitoring session:

identifying, by the computing device, the area of the chest of the subject to which the emitter points the radio wave; and selecting, by the computing device, and based on the identified area, one of the plurality of neural networks to be used to generate a breathing volume estimation.

17. The method of claim 16 further comprising generating, by the computing device, the breathing volume estimation using the selected one of the plurality of neural networks.

18. The method of claim 16, wherein emitting a continuous radio wave comprises emitting a single tone continuous radio wave at about 2.4 GHz.

19. The method of claim 16 further comprising decoding, by the computing device, the reflected radio wave to extract interfering signals due to at least one of: respiration, heartbeat, and random body movements, of the subject.

20. The method of claim 19 further comprising:

detecting, by the computing device, a change in a body posture of the subject based on a change in the interfering signals; and upon detecting the change in the body posture, repositioning at least one of the emitter, and the receiver to a position sufficient to extract the interfering signals.

21. The method of claim 20 further comprising identifying, by the computing device, one of a plurality of mapping relationships to apply for calculating the breathing volume of the subject in the changed body posture.

22. The method of claim 16, wherein monitoring the radio wave comprises collecting and outputting data at a sampling rate of about 1 kHz to about 100 kHz.

23. The method of claim 16 further comprising detecting, by the computing device, large- and small-scale body movement and radar occlusion in the subject.

24. The method of claim 16, wherein the emitter and the receiver are mounted on a mechanical motion control system, the method further comprising controlling, by a controller, the mechanical motion control system.

25. The method of claim 24, wherein controlling the mechanical motion control system comprises rotating the radio wave emitter and radio wave detector with 360° of freedom on three axes.

26. The method of claim 24 further comprising mounting the mechanical motion control system on a track.

27. The method of claim 24, wherein controlling the mechanical motion system comprises causing the mechanical motion control system to move across the chest of the subject.

28. The method of claim 24, wherein controlling the mechanical motion system comprises causing the mechanical motion control system to move along the length of the subject.

29. The method of claim 24 further comprising mounting the mechanical motion control system on a bed or another horizontal platform.

30. The method of claim 16 further comprising measuring the breathing volume of the subject using the spirometer.

\* \* \* \* \*

UNITED STATES PATENT AND TRADEMARK OFFICE
CERTIFICATE OF CORRECTION

PATENT NO. : 11,241,167 B2
APPLICATION NO. : 15/679282
DATED : February 8, 2022
INVENTOR(S) : Tam Vu et al.

It is certified that error appears in the above-identified patent and that said Letters Patent is hereby corrected as shown below:

In the Specification

Column 28, Line 21, equation, after "S(t)" delete "S(t)"

In the Claims

Column 46, Line 2, Claim 13, delete "subject's"

Signed and Sealed this
Fifteenth Day of November, 2022

Katherine Kelly Vidal
*Director of the United States Patent and Trademark Office*